(12) United States Patent
Cernak et al.

(10) Patent No.: US 9,511,052 B2
(45) Date of Patent: *Dec. 6, 2016

(54) MINERALOCORTICOID RECEPTOR ANTAGONISTS

(71) Applicant: Merck Sharp & Dohme Corp., Rahway, NJ (US)

(72) Inventors: Timothy A. Cernak, Boston, MA (US); Kevin D. Dykstra, West Milford, NJ (US); Dong-Ming Shen, Edison, NJ (US); Kun Liu, Needham, MA (US); Andrew Stamford, Chatham, NJ (US); John Qiang Tan, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/415,210

(22) PCT Filed: Jul. 15, 2013

(86) PCT No.: PCT/US2013/050427
§ 371 (c)(1),
(2) Date: Jan. 16, 2015

(87) PCT Pub. No.: WO2014/014794
PCT Pub. Date: Jan. 23, 2014

(65) Prior Publication Data
US 2015/0182503 A1 Jul. 2, 2015

Related U.S. Application Data

(60) Provisional application No. 61/673,615, filed on Jul. 19, 2012, provisional application No. 61/673,592, filed on Jul. 19, 2012.

(51) Int. Cl.
*C07D 231/56* (2006.01)
*A61K 31/416* (2006.01)
*A61K 45/06* (2006.01)

(52) U.S. Cl.
CPC ............ *A61K 31/416* (2013.01); *A61K 45/06* (2013.01); *C07D 231/56* (2013.01)

(58) Field of Classification Search
CPC ... C07D 231/56; C07D 401/14; C07D 405/04; A61K 31/416; A61K 49/0002
USPC ............................ 548/361.1, 362.5; 514/403
See application file for complete search history.

(56) References Cited

U.S. PATENT DOCUMENTS

| | | | |
|---|---|---|---|
| 8,933,113 B2 * | 1/2015 | Crespo | A61K 31/404 514/406 |
| 2006/0025459 A1 | 2/2006 | Demont et al. | |
| 2006/0235222 A1 | 10/2006 | Bell et al. | |
| 2008/0167345 A1 | 7/2008 | Jones et al. | |
| 2008/0312270 A1 | 12/2008 | Brown et al. | |
| 2009/0069400 A1 | 3/2009 | Bleisch et al. | |
| 2010/0105679 A1 | 4/2010 | Guzzo et al. | |
| 2014/0336224 A1 * | 11/2014 | Lan | C07D 413/06 514/338 |

FOREIGN PATENT DOCUMENTS

| | | | |
|---|---|---|---|
| WO | WO 2006109933 A1 * | 10/2006 | ........... C07D 401/14 |
| WO | WO2012097744 | 7/2012 | |
| WO | WO2012139495 | 10/2012 | |

OTHER PUBLICATIONS

Abbassi, N., et. al., "Studies on the reduction of the nitro group in 4-nitroindazoles by anhydrous SnCl2 in different alcohols", Synthetic Communications, vol. 41, No. 7, pp. 999-1005, 2011.
Corsi, G., et. al., "1-Halobenzyl-1 H-indazole-3-carboxylic acids. A new class of Antispermatogenic Agents", Journal of Medicinal Chemistry, vol. 19, No. 6, pp. 778-783, 1976.
International Search Report for PCT/US2013/050427, mailed on Dec. 9, 2013; 2 pages.

* cited by examiner

*Primary Examiner* — Alicia L Otton
*Assistant Examiner* — Sagar Patel
(74) *Attorney, Agent, or Firm* — Patricia A. Shatynski; Catherine D. Fitch

(57) ABSTRACT

The present invention is directed to compounds of the Formula I: as well as pharmaceutically acceptable salts thereof, that may be useful for treating aldosterone-mediated diseases. The invention furthermore relates to specific diastereomers and enantiomers of the compounds, to processes for preparing compounds of the Formula I, to their potential use for the therapy and prophylaxis of the above-mentioned diseases and for preparing pharmaceuticals for this purpose, and to pharmaceutical compositions which comprise compounds of the Formula I.

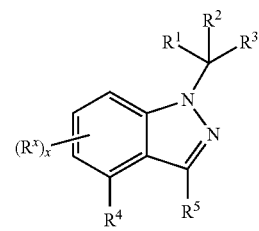

14 Claims, No Drawings

MINERALOCORTICOID RECEPTOR ANTAGONISTS

RELATED APPLICATIONS

This application is a §371 National Stage Application of PCT/US2013/050427, filed on 15 Jul. 2013, which claims benefit of provisional application U.S. Ser. No. 61/673,615, filed 19 Jul. 2012, and provisional application U.S. Ser. No. 61/673,592, filed 19 Jul. 2012, both herein incorporated by reference.

BACKGROUND OF THE INVENTION

The Mineralocorticoid Receptor (MR) is a nuclear hormone receptor that is activated by aldosterone and regulates the expression of many genes involved in electrolyte homeostasis and cardiovascular disease. Increased circulating aldosterone increases blood pressure through its effects on natriuresis, with potentially additional effects on the brain, heart and vasculature. In addition, hyperaldosteronism has been linked to many pathophysiological processes resulting in renal and cardiovascular disease. While hyperaldosteronism is commonly caused by aldosterone-producing adenomas, resistant hypertensive patients frequently suffer from increased aldosterone levels often termed as "Aldosterone Breakthrough" as a result of increases in serum potassium or residual AT1R activity. Hyperaldosteronism and aldosterone breakthrough typically results in increased MR activity and MR antagonists have been shown to be effective as anti-hypertensive agents and also in the treatment of heart failure and primary hyperaldosteronism.

In addition, in visceral tissues, such as the kidney and the gut, MR regulates sodium retention, potassium excretion and water balance in response to aldosterone. MR expression in the brain also appears to play a role in the control of neuronal excitability, in the negative feedback regulation of the hypothalamic-pituitary-adrenal axis, and in the cognitive aspects of behavioral performance (Castren et al., J. of Neuroendocrinology, 3, 461-66 (1993)).

Eplerenone and spironolactone are two MR antagonists that have been shown to be efficacious in treating cardiovascular disease, particularly hypertension and heart failure (RALES Investigators (1999) The Effect of Spironolactone on Morbidity and Mortality in Patients with Severe Heart Failure, N. Engl. J. Med., 1999, 341(10):709-717; Pitt B, et al., EPHESUS investigator (2003) Eplerenone, a Selective Aldosterone Blocker, in Patients with Left Ventricular Dysfunction After Myocardial Infarction, N. Engl. J. Med., 348(14):1309-1321; Funder J W., (2010) Eplerenone in Chronic Renal Disease: the EVALUATE trial, Hypertens. Res., 33(6):539-40.). Moreover, multiple studies have shown that treatment with spironolactone or eplerenone significantly lower systolic blood pressure in mild-moderate, obese, systolic, PHA, and resistant hypertensive patients (Calhoun D A, et al., (2008) Effectiveness of the Selective Aldosterone Blocker, Eplerenone, in Patients with Resistant Hypertension, J. Am. Soc. Hypertens., 2008 November-December; 2(6):462-8; Huang B S, et al., (2010) Central Neuronal Activation and Pressor Responses Induced by Circulating ANG II: role of the brain aldosterone-"ouabain" pathway, Am. J. Physiol. Heart. Circ. Physiol., (2)::H422-30; The RALES Investigators. (1996) Effectiveness of Spironolactone added to an Angiotensin-converting enzyme Inhibitor and a Loop Diuretic for Severe Chronic Congestive Heart Failure, (The Randomized Aldactone Evaluation Study [RALES]), Am. J. Cardiol., 1996; 78:902-907; Pitt B, et al., EPHESUS Investigators, Serum potassium and clinical outcomes in the Eplerenone Post-Acute Myocardial Infarction Heart Failure Efficacy and Survival Study (EPHESUS), Circulation, 2008 Oct. 14; 118(16):1643-50; Bomback A S et al., (2009), Low-dose spironolactone, added to long-term ACE inhibitor therapy, reduces blood pressure and urinary albumin excretion in obese patients with hypertensive target organ damage, Clin. Nephrol., 72(6):449-56; Williams J S, Hypertension: spironolactone and resistant hypertension, Nat. Rev. Endocrinol., 2010 May; 6(5):248-50; Nishizaka M K, et al., The role of aldosterone antagonists in the management of resistant hypertension. Curr Hypertens Rep. 2005 October; 7(5):343-7. Review; Gaddam K, et al., (2010) Rapid reversal of left ventricular hypertrophy and intracardiac volume overload in patients with resistant hypertension and hyperaldosteronism: a prospective clinical study, Hypertension, 55(5):1137-42; Zannad F, et al., (2010) Rationale and design of the Eplerenone in Mild Patients Hospitalization And Survival Study in Heart Failure (EMPHASIS-HF), Eur. J. Heart Fail., 12(6):617-22).

Evidence in preclinical models also suggest that MR antagonists would be efficacious in treating the metabolic syndrome and atherosclerosis (Takai, S. et al, (2005) Eplerenone inhibits atherosclerosis in nonhuman primates. Hypertension. 46(5):1135-9; Tirosh, A. et al., G K. (2010) Mineralocorticoid receptor antagonists and the metabolic syndrome. Curr Hypertens Rep. 2010 August; 12(4):252-7).

There is also evidence that MR antagonists may be efficacious in treating retinopathy. (Zhao et. al, (2012) Mineralocorticoid receptor is involved in rat and human ocular chorioretinopathy; The Journal of Clinical Investigation, Vol. 122(7): 2672).

There is also evidence that MR antagonists may be efficacious in treating obstructive sleep apnea, which is usually associated with cardiac disease. (Clark, D., et al., Resistant Hypertension an Aldosterone: An Update; Canadian Journal of Cardiology, (2012) Vol 28, pp 318-325).

Also, published PCT application WO 2002/17895 disclosed that aldosterone antagonists may be useful in the treatment of subjects suffering from one or more cognitive dysfunctions including, but not limited to psychoses, cognitive disorders (such as memory disturbances), mood disorders (such as depression and bipolar disorder), anxiety disorders and personality disorders.

Elevation in aldosterone levels, or excess stimulation of mineralocorticoid receptors, is linked to several physiological disorders or pathologic disease states, including Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels. (Hadley, M. E., ENDOCRINOLOGY, $2^{nd}$ Ed., pp. 366-81, (1988); and Brilla et al., Journal of Molecular and Cellular Cardiology, 25 (5), pp. 563-75 (1993)). Compounds and/or pharmaceutical compositions which act as MR antagonists may be of value in the treatment of any of the above conditions.

Despite significant therapeutic advances in the treatment of hypertension and heart failure, the current standard of care is suboptimal and there is a clear unmet medical need for additional therapeutic/pharmacological interventions. This invention addresses those needs by providing compounds and compositions which may be useful for the treatment or prevention of hypertension, heart failure, other cardiovascular disorders and other aldosterone disorders.

SUMMARY OF THE INVENTION

The present invention relates to compounds which have Mineralocorticoid Receptor (MR) antagonist activity, which may be valuable pharmaceutically active compounds for the therapy and prophylaxis of diseases, for example for treating aldosterone-mediated disorders, including cardiovascular disease. The present invention is directed to compounds of the Formula I:

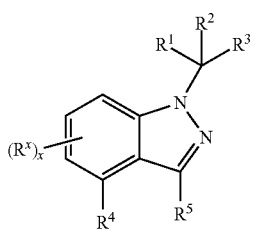

or a pharmaceutically acceptable salt thereof. The invention furthermore relates to specific diastereomers and enantiomers, methods of treating and preventing the above mentioned diseases and to processes for preparing compounds of the Formula I and for pharmaceutical preparations which comprise compounds of Formula I.

DETAILED DESCRIPTION OF THE INVENTION

The invention concerns compounds of Formula I:

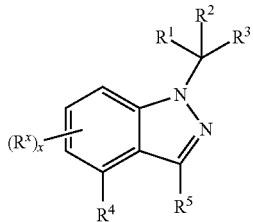

or a pharmaceutically acceptable salt thereof, wherein
Each $R^x$ is independently H, halo, or $C_1$-$C_6$ alkyl, said alkyl is optionally substituted with 1 to 3 substituents selected from halo, OR and $C_1$-$C_6$ alkyl;
Each R is independently H or $C_1$-$C_6$ alkyl, said alkyl is optionally substituted with 1 to 4 halo substituents;
$R^1$ is $C_1$-$C_6$ alkyl, or $C(O)NRR^6$;
wherein said alkyl is optionally substituted with one to three $CF_3$, OR, CN, or halo substituents;
$R^2$ is $C_1$-$C_6$ alkyl, said alkyl is optionally substituted with one to three OR, CN or halo substituents;
$R^3$ is aryl-$X_t$;
$R^4$ is —$NR^6S(O)_2R^8$,
$R^5$ is H, $C_1$-$C_6$ alkyl, CN, or OR;
Each $R^6$ is independently H, $C_1$-$C_6$ alkyl, $C_3$-$C_{10}$ cycloalkyl, heteroaryl or aryl, said alkyl, cycloalkyl, or heteroaryl may be optionally substituted with aryl, heteroaryl or heterocyclyl;
Each $R^8$ is independently $C_1$-$C_6$ alkyl, $C_3$-$C_{10}$ cycloalkyl or aryl, said alkyl, cycloalkyl and aryl are optionally substituted with one to three $C_3$-$C_{10}$ cycloalkyl or halo substituents;

Each X is independently halo, CN, $CF_3$, or $SF_5$;
t is 1, 2 or 3;
x is 0, 1, 2 or 3.
In another embodiment of the compounds of Formula I, $R^3$ is

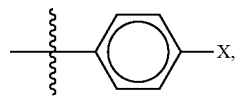

and all other variables are as previously defined above for Formula I.
In another embodiment of the compounds of Formula I,
$R^4$ is $NHS(O)_2R^8$,
$R^5$ is H,
and all other variables are as previously defined above for Formula I.
In an embodiment, the invention concerns a compound which is:

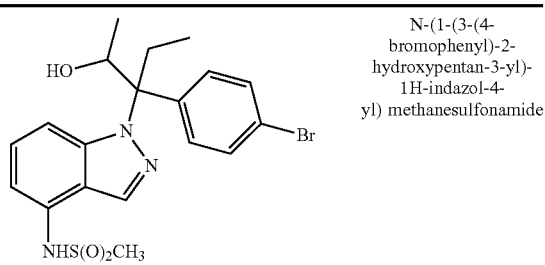

N-(1-(3-(4-bromophenyl)-2-hydroxypentan-3-yl)-1H-indazol-4-yl) methanesulfonamide

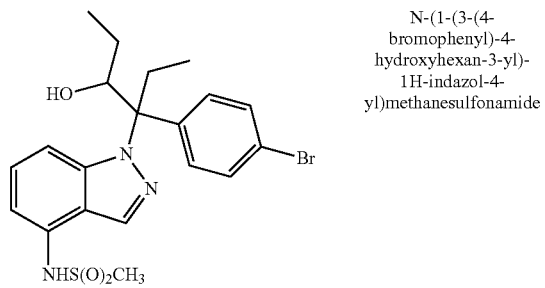

N-(1-(3-(4-bromophenyl)-4-hydroxyhexan-3-yl)-1H-indazol-4-yl)methanesulfonamide

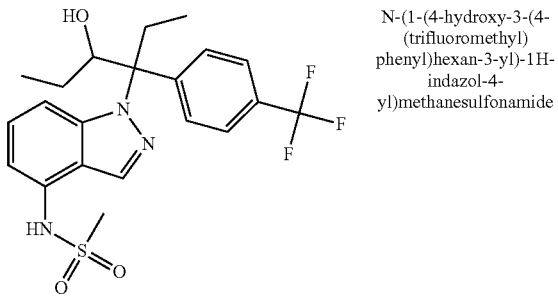

N-(1-(4-hydroxy-3-(4-(trifluoromethyl)phenyl)hexan-3-yl)-1H-indazol-4-yl)methanesulfonamide

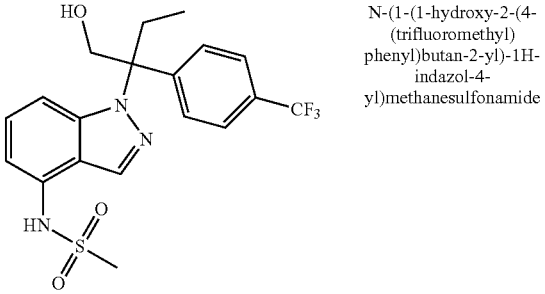

N-(1-(1-hydroxy-2-(4-(trifluoromethyl)phenyl)butan-2-yl)-1H-indazol-4-yl)methanesulfonamide

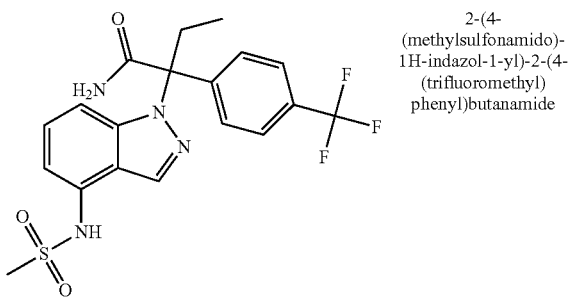 2-(4-(methylsulfonamido)-1H-indazol-1-yl)-2-(4-(trifluoromethyl)phenyl)butanamide

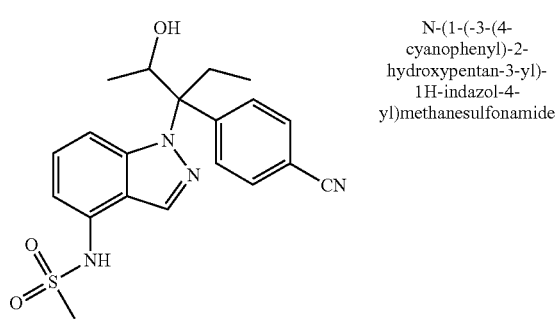 N-(1-(-3-(4-cyanophenyl)-2-hydroxypentan-3-yl)-1H-indazol-4-yl)methanesulfonamide

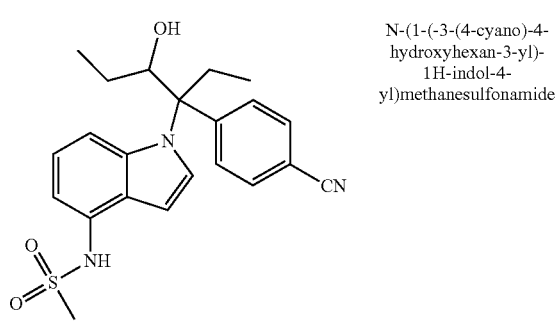 N-(1-(-3-(4-cyano)-4-hydroxyhexan-3-yl)-1H-indol-4-yl)methanesulfonamide

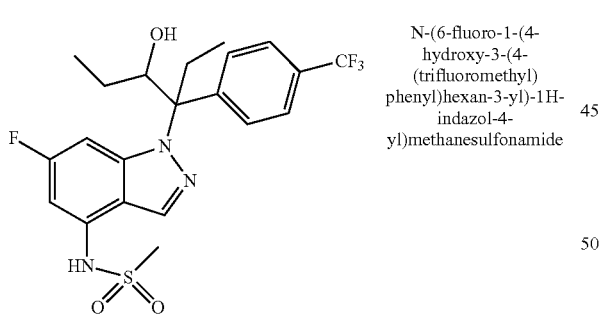 N-(6-fluoro-1-(4-hydroxy-3-(4-(trifluoromethyl)phenyl)hexan-3-yl)-1H-indazol-4-yl)methanesulfonamide

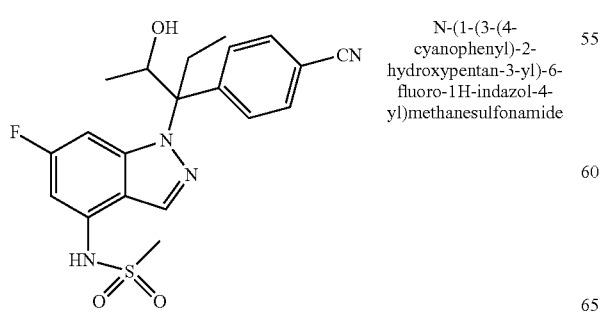 N-(1-(3-(4-cyanophenyl)-2-hydroxypentan-3-yl)-6-fluoro-1H-indazol-4-yl)methanesulfonamide

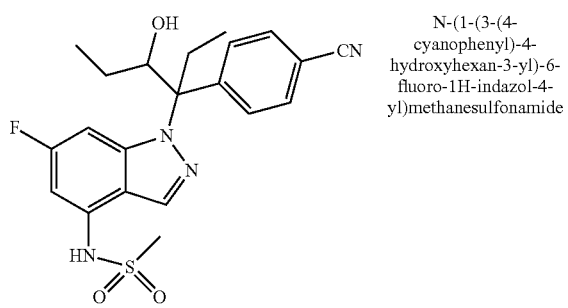 N-(1-(3-(4-cyanophenyl)-4-hydroxyhexan-3-yl)-6-fluoro-1H-indazol-4-yl)methanesulfonamide

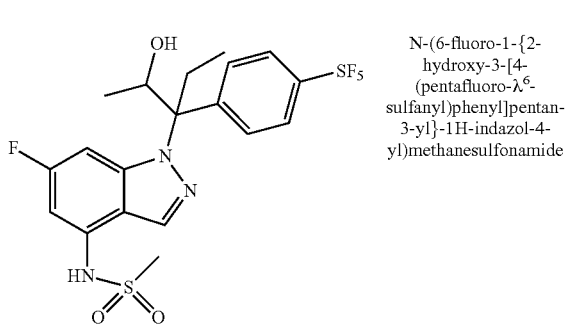 N-(6-fluoro-1-{2-hydroxy-3-[4-(pentafluoro-λ⁶-sulfanyl)phenyl]pentan-3-yl}-1H-indazol-4-yl)methanesulfonamide

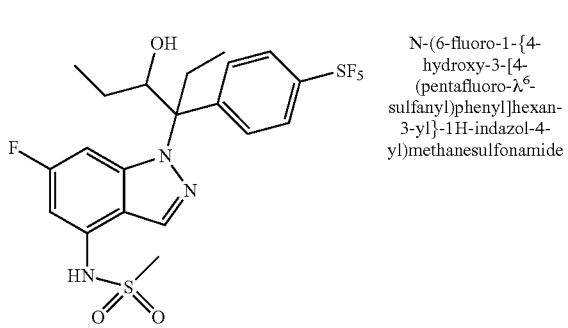 N-(6-fluoro-1-{4-hydroxy-3-[4-(pentafluoro-λ⁶-sulfanyl)phenyl]hexan-3-yl}-1H-indazol-4-yl)methanesulfonamide

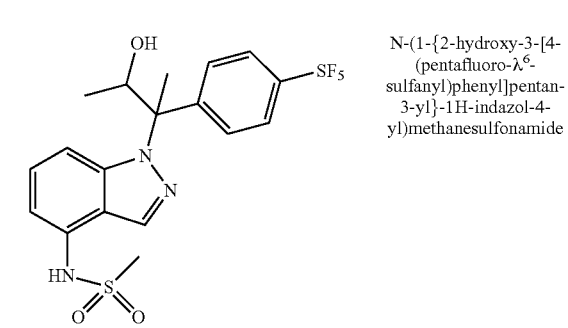 N-(1-{2-hydroxy-3-[4-(pentafluoro-λ⁶-sulfanyl)phenyl]pentan-3-yl}-1H-indazol-4-yl)methanesulfonamide

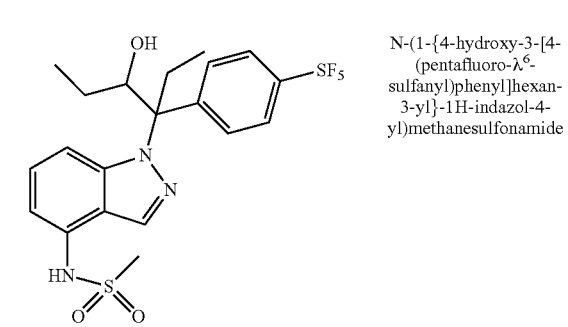 N-(1-{4-hydroxy-3-[4-(pentafluoro-λ⁶-sulfanyl)phenyl]hexan-3-yl}-1H-indazol-4-yl)methanesulfonamide

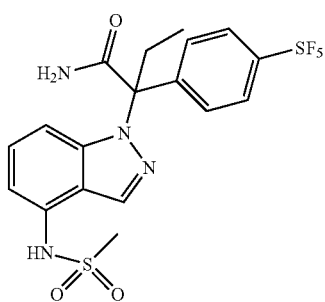

2-{4-[(methylsulfonyl)amino]-1H-indazol-1-yl}-2-[4-(pentafluoro-λ⁶-sulfanyl)phenyl]butanamide

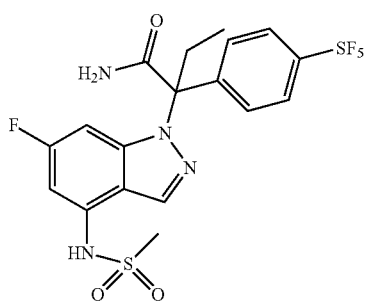

2-{6-fluoro-4-[(methylsulfonyl)amino]-1H-indazol-1-yl}-2-[4-(pentafluoro-λ⁶-sulfanyl)phenyl]butanamide or a pharmaceutically acceptable salt thereof.

In another embodiment, a compound which is

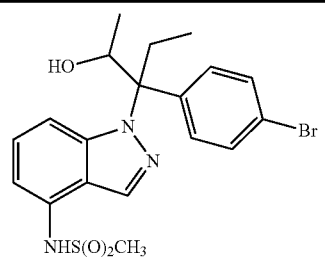

N-(1-(3-(4-bromophenyl)-2-hydroxypentan-3-yl)-1H-indazol-4-yl) methanesulfonamide

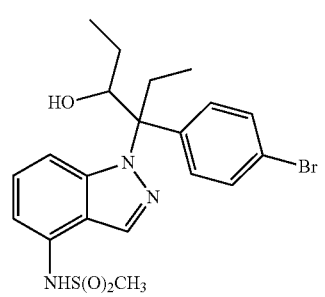

N-(1-(3-(4-bromophenyl)-4-hydroxyhexan-3-yl)-1H-indazol-4-yl)methanesulfonamide

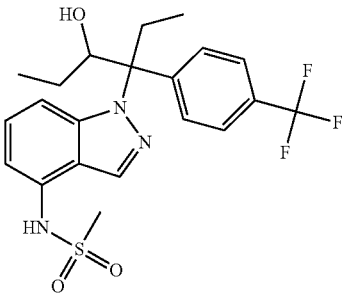 [SMILES: CCC(O)C(CC)(c1ccc(C(F)(F)F)cc1)n1ncc2c(NS(C)(=O)=O)cccc21]

N-(1-(4-hydroxy-3-(4-(trifluoromethyl)phenyl)hexan-3-yl)-1H-indazol-4-yl)methanesulfonamide

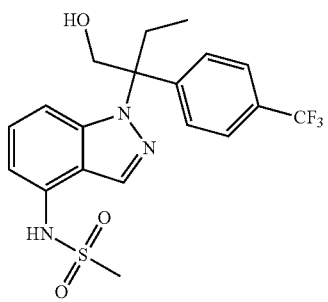 [SMILES: CCC(CO)(c1ccc(C(F)(F)F)cc1)n1ncc2c(NS(C)(=O)=O)cccc21]

N-(1-(1-hydroxy-2-(4-(trifluoromethyl)phenyl)butan-2-yl)-1H-indazol-4-yl)methanesulfonamide

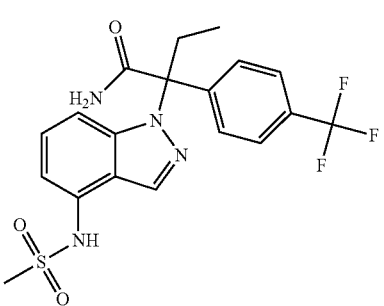 [SMILES: CCC(C(N)=O)(c1ccc(C(F)(F)F)cc1)n1ncc2c(NS(C)(=O)=O)cccc21]

2-(4-(methylsulfonamido)-1H-indazol-1-yl)-2-(4-(trifluoromethyl)phenyl)butanamide

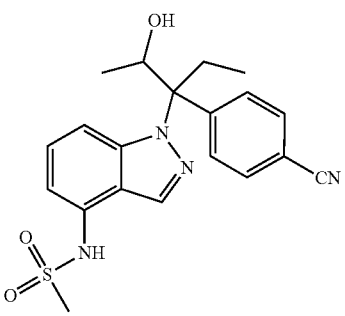 [SMILES: CCC(c1ccc(C#N)cc1)(C(C)O)n1ncc2c(NS(C)(=O)=O)cccc21]

N-(1-(3-(4-cyanophenyl)-2-hydroxypentan-3-yl)-1H-indazol-4-yl)methanesulfonamide

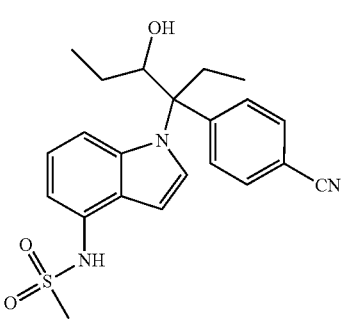 [SMILES: CCC(O)C(CC)(c1ccc(C#N)cc1)n1ccc2c(NS(C)(=O)=O)cccc21]

N-(1-(3-(4-cyano)-4-hydroxyhexan-3-yl)-1H-indol-4-yl)methanesulfonamide or a pharmaceutically acceptable salt thereof.

In a further embodiment, a compound which is

| | | |
|---|---|---|
| 1 | 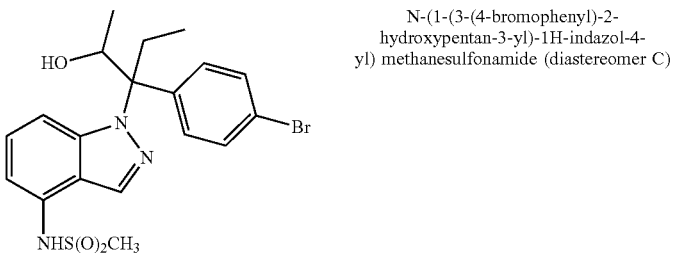 | N-(1-(3-(4-bromophenyl)-2-hydroxypentan-3-yl)-1H-indazol-4-yl) methanesulfonamide (diastereomer C) |
| 2 | 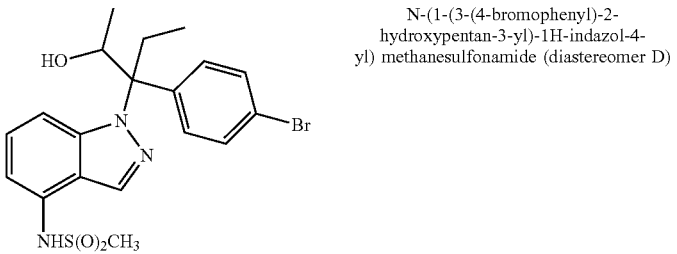 | N-(1-(3-(4-bromophenyl)-2-hydroxypentan-3-yl)-1H-indazol-4-yl) methanesulfonamide (diastereomer D) |
| 3 | 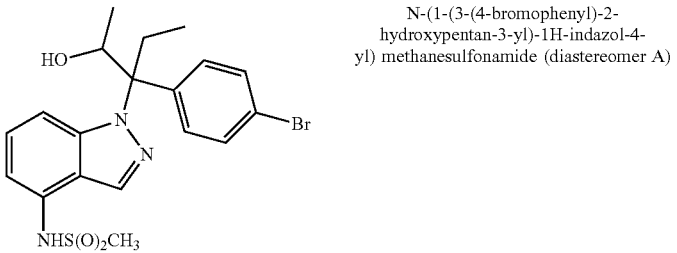 | N-(1-(3-(4-bromophenyl)-2-hydroxypentan-3-yl)-1H-indazol-4-yl) methanesulfonamide (diastereomer A) |
| 4 | 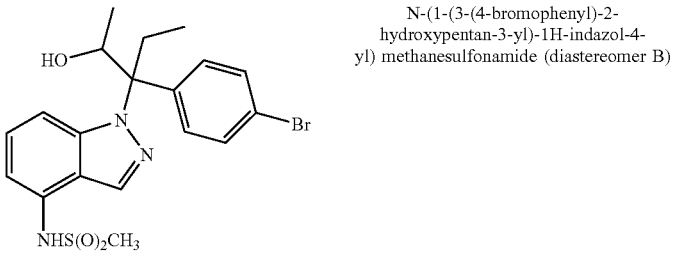 | N-(1-(3-(4-bromophenyl)-2-hydroxypentan-3-yl)-1H-indazol-4-yl) methanesulfonamide (diastereomer B) |
| 5 | 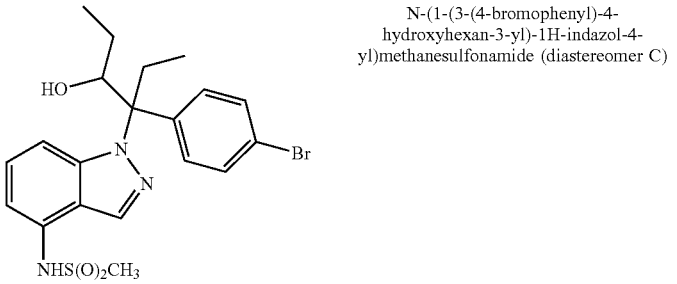 | N-(1-(3-(4-bromophenyl)-4-hydroxyhexan-3-yl)-1H-indazol-4-yl)methanesulfonamide (diastereomer C) |
| 6 | 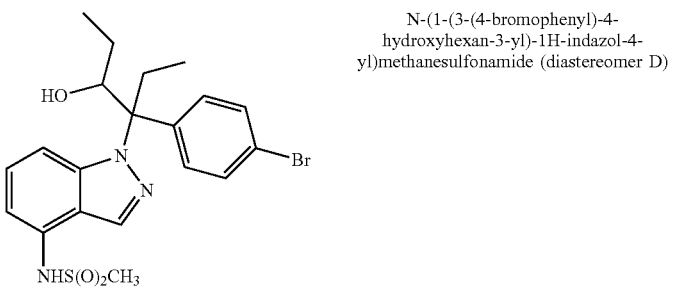 | N-(1-(3-(4-bromophenyl)-4-hydroxyhexan-3-yl)-1H-indazol-4-yl)methanesulfonamide (diastereomer D) |

| | | |
|---|---|---|
| 7 | 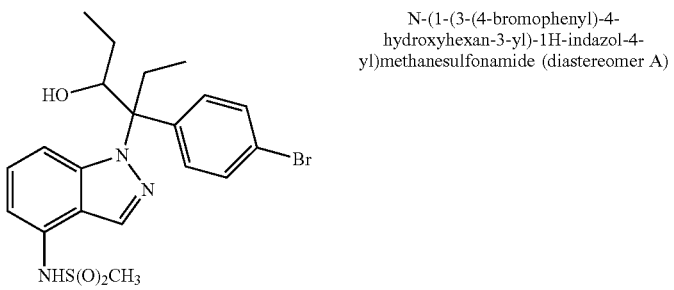 | N-(1-(3-(4-bromophenyl)-4-hydroxyhexan-3-yl)-1H-indazol-4-yl)methanesulfonamide (diastereomer A) |
| 8 | 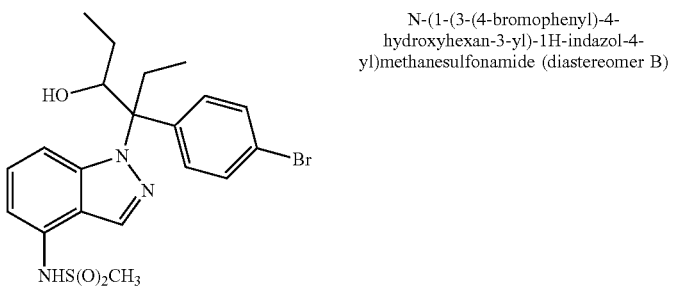 | N-(1-(3-(4-bromophenyl)-4-hydroxyhexan-3-yl)-1H-indazol-4-yl)methanesulfonamide (diastereomer B) |
| 9 | 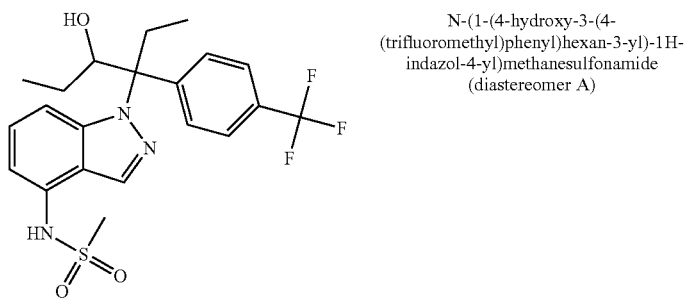 | N-(1-(4-hydroxy-3-(4-(trifluoromethyl)phenyl)hexan-3-yl)-1H-indazol-4-yl)methanesulfonamide (diastereomer A) |
| 10 | 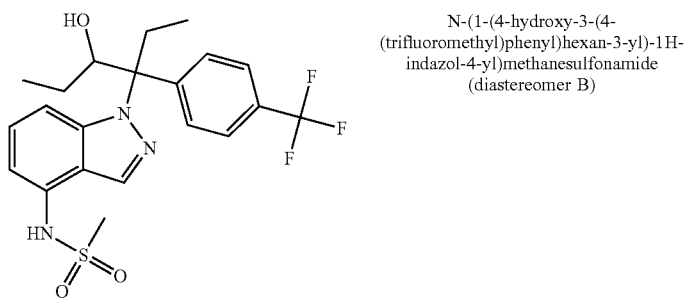 | N-(1-(4-hydroxy-3-(4-(trifluoromethyl)phenyl)hexan-3-yl)-1H-indazol-4-yl)methanesulfonamide (diastereomer B) |
| 11 | 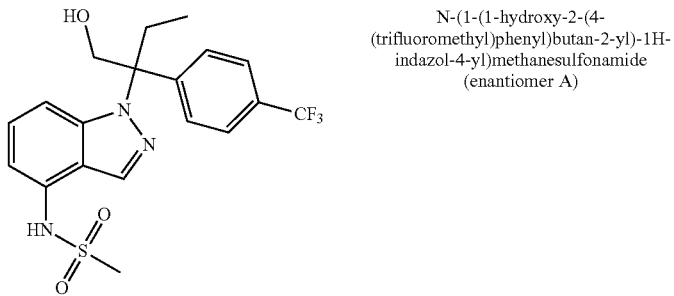 | N-(1-(1-hydroxy-2-(4-(trifluoromethyl)phenyl)butan-2-yl)-1H-indazol-4-yl)methanesulfonamide (enantiomer A) |

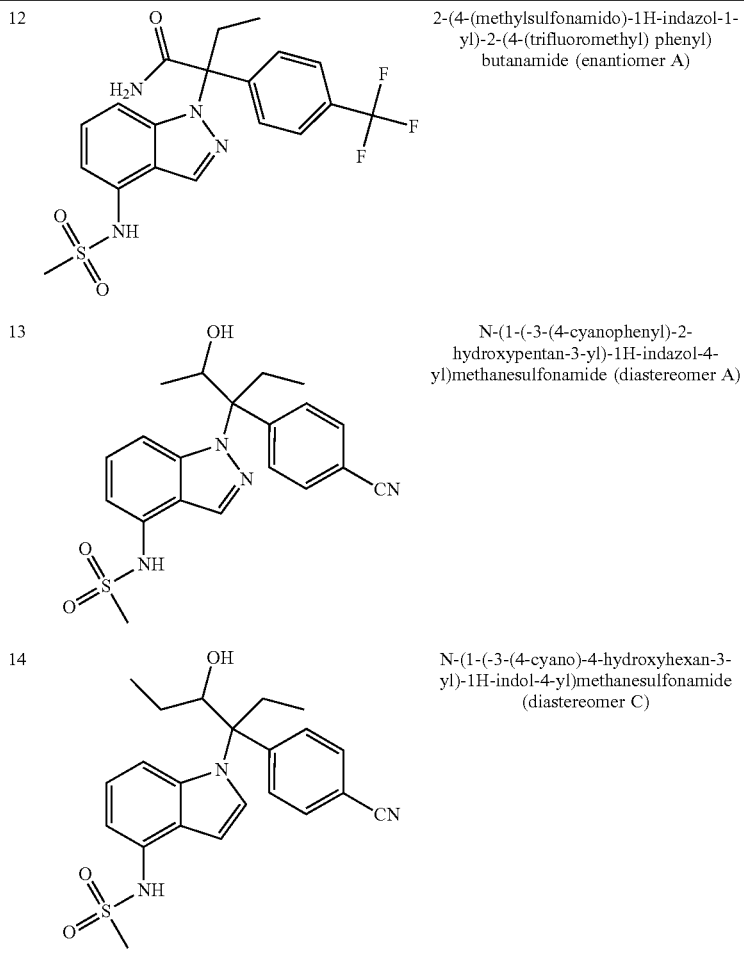
or a pharmaceutically acceptable salt thereof.
In a further embodiment, a compound which is
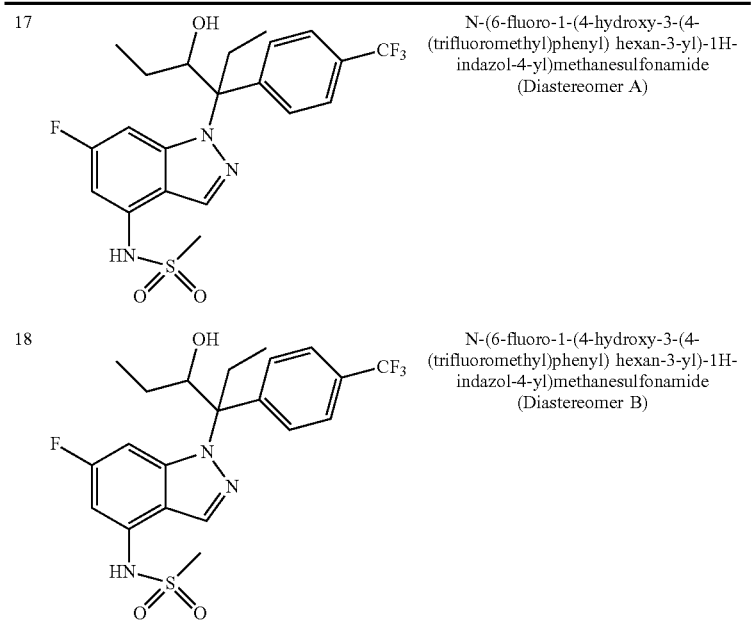

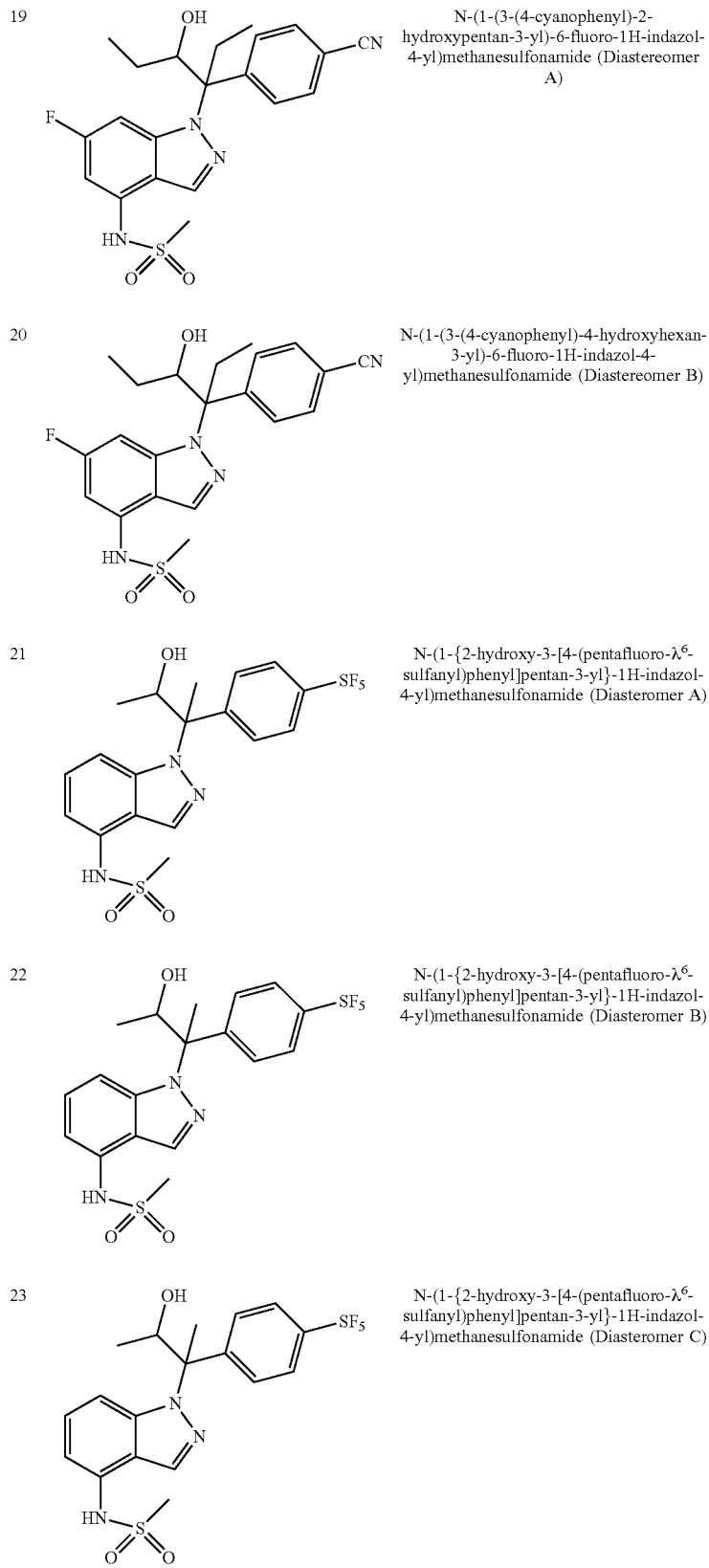

| | | |
|---|---|---|
| 19 | | N-(1-(3-(4-cyanophenyl)-2-hydroxypentan-3-yl)-6-fluoro-1H-indazol-4-yl)methanesulfonamide (Diastereomer A) |
| 20 | | N-(1-(3-(4-cyanophenyl)-4-hydroxyhexan-3-yl)-6-fluoro-1H-indazol-4-yl)methanesulfonamide (Diastereomer B) |
| 21 | | N-(1-{2-hydroxy-3-[4-(pentafluoro-$\lambda^6$-sulfanyl)phenyl]pentan-3-yl}-1H-indazol-4-yl)methanesulfonamide (Diasteromer A) |
| 22 | | N-(1-{2-hydroxy-3-[4-(pentafluoro-$\lambda^6$-sulfanyl)phenyl]pentan-3-yl}-1H-indazol-4-yl)methanesulfonamide (Diastereomer B) |
| 23 | | N-(1-{2-hydroxy-3-[4-(pentafluoro-$\lambda^6$-sulfanyl)phenyl]pentan-3-yl}-1H-indazol-4-yl)methanesulfonamide (Diasteromer C) |

-continued

| | | |
|---|---|---|
| 24 | 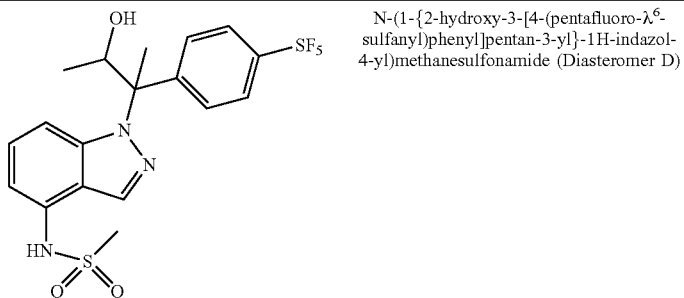 | N-(1-{2-hydroxy-3-[4-(pentafluoro-$\lambda^6$-sulfanyl)phenyl]pentan-3-yl}-1H-indazol-4-yl)methanesulfonamide (Diasteromer D) |
| 25 | 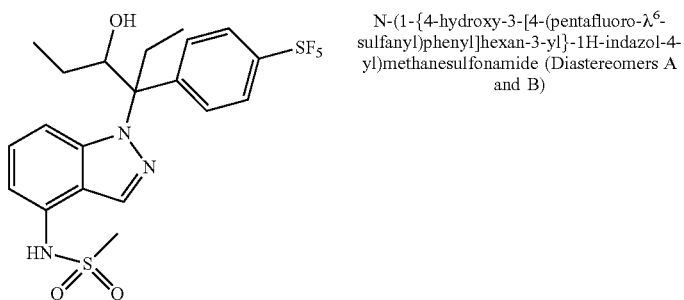 | N-(1-{4-hydroxy-3-[4-(pentafluoro-$\lambda^6$-sulfanyl)phenyl]hexan-3-yl}-1H-indazol-4-yl)methanesulfonamide (Diastereomers A and B) |
| 26 | 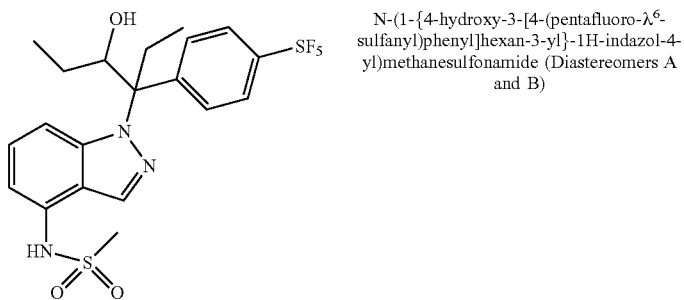 | N-(1-{4-hydroxy-3-[4-(pentafluoro-$\lambda^6$-sulfanyl)phenyl]hexan-3-yl}-1H-indazol-4-yl)methanesulfonamide (Diastereomers A and B) |
| 27 | 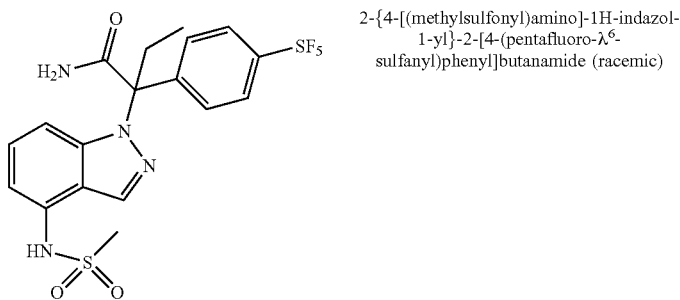 | 2-{4-[(methylsulfonyl)amino]-1H-indazol-1-yl}-2-[4-(pentafluoro-$\lambda^6$-sulfanyl)phenyl]butanamide (racemic) | or a pharmaceutically acceptable salt thereof.

Another embodiment of the invention concerns compounds of Formula II:

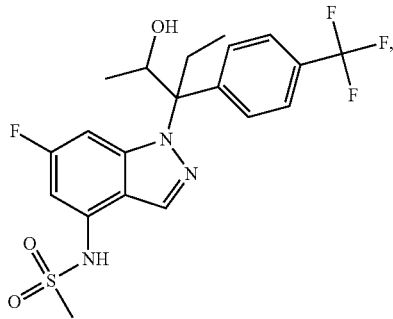 [SMILES: CCC(c1ccc(C(F)(F)F)cc1)(C(C)O)n1ncc2c(NS(C)(=O)=O)cc(F)cc21]

which is racemic N-(6-fluoro-1-(2-hydroxy-3-(4-(trifluoromethyl)phenyl)pentan-3-yl)-1H-indazol-4-yl)methanesulfonamide or a pharmaceutically acceptable salt thereof.

In a further embodiment, the invention concerns a compound which is

| COMPOUND NO. | Chemical Name |
| --- | --- |
| 31 | N-(6-fluoro-1-(2-hydroxy-3-(4-(trifluoromethyl)phenyl)pentan-3-yl)-1H-indazol-4-yl)methanesulfonamide (diastereomer A) |
| 32 | N-(6-fluoro-1-(2-hydroxy-3-(4-(trifluoromethyl)phenyl)pentan-3-yl)-1H-indazol-4-yl)methanesulfonamide (diastereomer B) |
| 33 | N-(6-fluoro-1-(2-hydroxy-3-(4-(trifluoromethyl)phenyl)pentan-3-yl)-1H-indazol-4-yl)methanesulfonamide (diastereomer C) |
| 34 | N-(6-fluoro-1-(2-hydroxy-3-(4-(trifluoromethyl)phenyl)pentan-3-yl)-1H-indazol-4-yl)methanesulfonamide (diastereomer D) | or a pharmaceutically acceptable salt thereof

Another embodiment, is a compound which is

| Compound No. | Structure | IUPAC Name |
| --- | --- | --- |
| 35 | 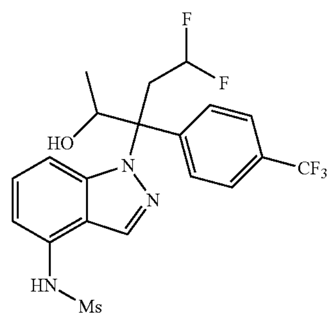 [SMILES: CC(O)C(CC(F)F)(c1ccc(C(F)(F)F)cc1)n1ncc2c(NS(C)(=O)=O)cccc21] | N-(1-(1,1-difluoro-4-hydroxy-3-(4-(trifluoromethyl)phenyl)pentan-3-yl)-1H-indazol-4-yl)methanesulfonamide (Diastereomer C) |
| 36 | 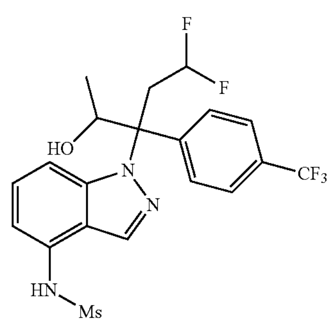 [SMILES: CC(O)C(CC(F)F)(c1ccc(C(F)(F)F)cc1)n1ncc2c(NS(C)(=O)=O)cccc21] | N-(1-(1,1-difluoro-4-hydroxy-3-(4-(trifluoromethyl)phenyl)pentan-3-yl)-1H-indazol-4-yl)methanesulfonamide (Diastereomer D) |
| 37 | 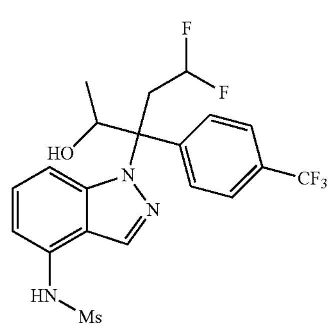 [SMILES: CC(O)C(CC(F)F)(c1ccc(C(F)(F)F)cc1)n1ncc2c(NS(C)(=O)=O)cccc21] | N-(1-(1,1-difluoro-4-hydroxy-3-(4-(trifluoromethyl)phenyl)pentan-3-yl)-1H-indazol-4-yl)methanesulfonamide (Diastereomer A) |

-continued

| Compound No. | Structure | IUPAC Name |
| --- | --- | --- |
| 38 | 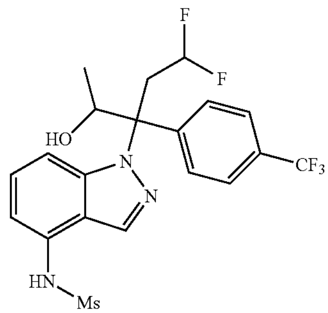 [SMILES: CC(O)C(CC(F)F)(c1ccc(C(F)(F)F)cc1)n1ncc2c(NS(C)(=O)=O)cccc21] | N-(1-(1,1-difluoro-4-hydroxy-3-(4-(trifluoromethyl)phenyl)pentan-3-yl)-1H-indazol-4-yl)methanesulfonamide (Diastereomer B) |
| 39 | 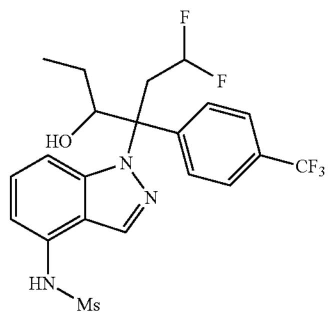 [SMILES: CCC(O)C(CC(F)F)(c1ccc(C(F)(F)F)cc1)n1ncc2c(NS(C)(=O)=O)cccc21] | N-(1-(1,1-difluoro-4-hydroxy-3-(4-(trifluoromethyl)phenyl)hexan-3-yl)-1H-indazol-4-yl)methanesulfonamide (Diastereomer C) |
| 40 | 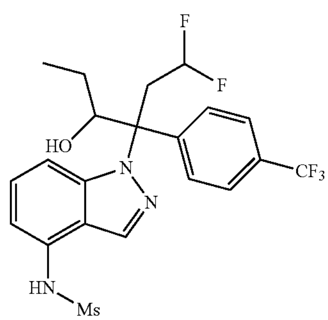 [SMILES: CCC(O)C(CC(F)F)(c1ccc(C(F)(F)F)cc1)n1ncc2c(NS(C)(=O)=O)cccc21] | N-(1-(1,1-difluoro-4-hydroxy-3-(4-(trifluoromethyl)phenyl)hexan-3-yl)-1H-indazol-4-yl)methanesulfonamide (Diastereomer D) |
| 41 | 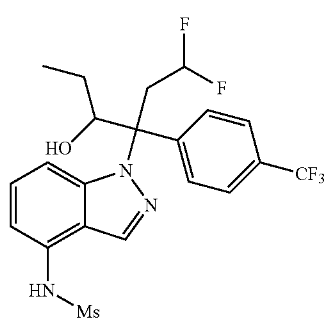 [SMILES: CCC(O)C(CC(F)F)(c1ccc(C(F)(F)F)cc1)n1ncc2c(NS(C)(=O)=O)cccc21] | N-(1-(1,1-difluoro-4-hydroxy-3-(4-(trifluoromethyl)phenyl)hexan-3-yl)-1H-indazol-4-yl)methanesulfonamide (Diastereomer A) |

-continued

| Compound No. | Structure | IUPAC Name |
|---|---|---|
| 42 | | N-(1-(1,1-difluoro-4-hydroxy-3-(4-(trifluoromethyl)phenyl)hexan-3-yl)-1H-indazol-4-yl)methanesulfonamide (Diastereomer B) | or a pharmaceutically acceptable salt thereof.

Another embodiments is a compound according which is

43

N-(1-(4,4-difluoro-1-hydroxy-2-(4-(trifluoromethyl)phenyl)butan-2-yl)-1H-indazol-4-yl)methanesulfonamide (Enantiomer A)

44

N-(1-(4,4-difluoro-1-hydroxy-2-(4-(trifluoromethyl)phenyl)butan-2-yl)-1H-indazol-4-yl)methanesulfonamide (Enantiomer B)

45

4,4-difluoro-2-(4-methylsulfonamido)-1H-indazol-1-yl)-2-(4-trifluoromethyl)phenyl) butanamide (Enantiomer A)

46

4,4-difluoro-2-(4-methylsulfonamido)-1H-indazol-1-yl)-2-(4-trifluoromethyl)phenyl) butanamide (Enantiomer B)

or a pharmaceutically acceptable salt thereof

Another embodiment is a compound according which is

| Compound Number | Structure | IUPAC Name |
| --- | --- | --- |
| 47 | 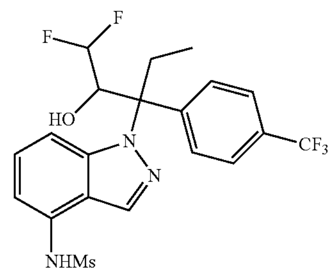 | N-(1-(1,1-difluoro-2-hydroxy-3-(4-(trifluoromethyl)phenyl)pentan-3-yl)-1H-indazol-4-yl)methanesulfonamide (Diastereomer A) |
| 48 | 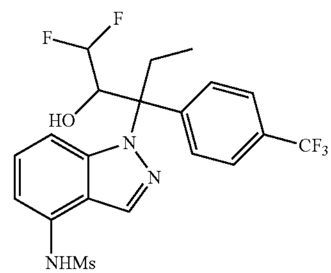 | N-(1-(1,1-difluoro-2-hydroxy-3-(4-(trifluoromethyl)phenyl)pentan-3-yl)-1H-indazol-4-yl)methanesulfonamide (Diastereomer B) |
| 49 | 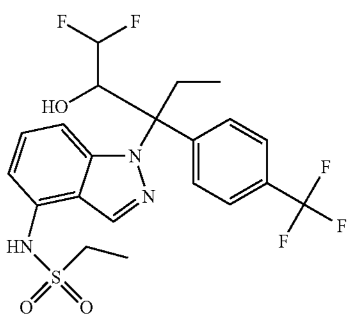 [SMILES: CCC(c1ccc(C(F)(F)F)cc1)(C(O)C(F)F)n1ncc2c(NS(=O)(=O)CC)cccc21] | N-(1-(1,1-difluoro-2-hydroxy-3-(4-(trifluoromethyl)phenyl)pentan-3-yl)-1H-indazol-4-yl)ethanesulfonamide (Diastereomer A) |
| 50 | 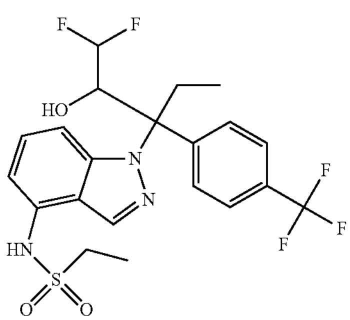 [SMILES: CCC(c1ccc(C(F)(F)F)cc1)(C(O)C(F)F)n1ncc2c(NS(=O)(=O)CC)cccc21] | N-(1-(1,1-difluoro-2-hydroxy-3-(4-(trifluoromethyl)phenyl)pentan-3-yl)-1H-indazol-4-yl)ethanesulfonamide (Diastereomer B) |
| 51 | 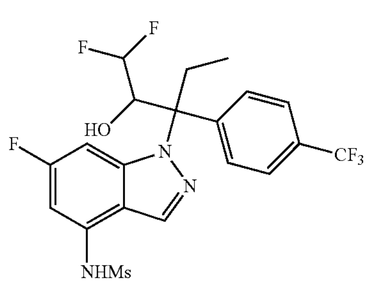 | N-(1-(1,1-difluoro-2-hydroxy-3-(4-(trifluoromethyl)phenyl)pentan-3-yl)-6-fluoro-1H-indazol-4-yl)methanesulfonamide (diastereomer A) |

-continued

| Compound Number | Structure | IUPAC Name |
|---|---|---|
| 52 | 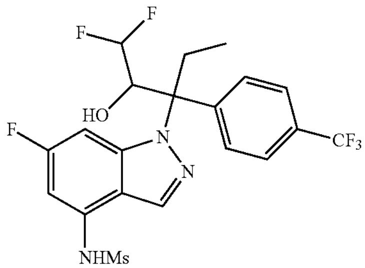 | N-(1-(1,1-difluoro-2-hydroxy-3-(4-(trifluoromethyl) phenyl) pentan-3-yl)-6-fluoro-1H-indazol-4-l) methanesulfonamide (diastereomer B) |
| 53 | 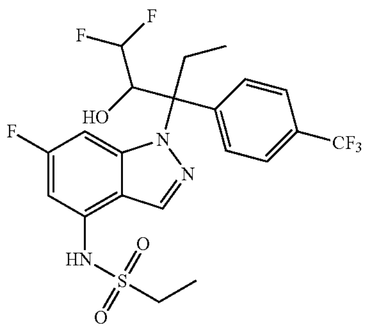 [SMILES: CCC(c1ccc(C(F)(F)F)cc1)(C(O)C(F)F)n1ncc2c(NS(=O)(=O)CC)cc(F)cc21] | N-(1-(1,1-difluoro-2-hydroxy-3-(4-(trifluoromethyl)phenyl) pentan-3-yl)-6-fluoro-1H-indazol-4-yl)ethanesulfonamide (diastereomer A) |
| 54 | | N-(1-(1,1-difluoro-2-hydroxy-3-(4-(trifluoromethyl)phenyl) pentan-3-yl)-6-fluoro-1H-indazol-4-l)ethanesulfonamide (diastereomer B) | or a pharmaceutically acceptable salt thereof.

Another embodiment is a compound according which is

| Compound Number | Structure | IUPAC Name | Exact Mass [M + H]+ |
|---|---|---|---|
| 55 | 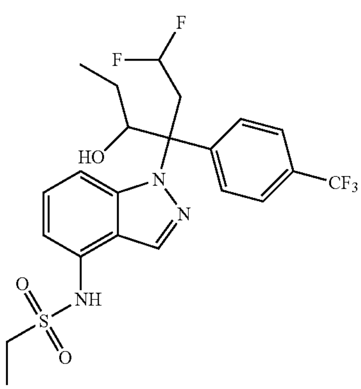 [SMILES: CCC(O)C(CC(F)F)(c1ccc(C(F)(F)F)cc1)n1ncc2c(NS(=O)(=O)CC)cccc21] | N-(1-(1,1-difluoro-4-hydroxy-3-(4-(trifluoromethyl)phenyl) hexan-3-yl)-1H-indazol-4-yl)ethanesulfonamide (Diastereomer C) | 506.1 |

| Compound Number | Structure | IUPAC Name | Exact Mass [M + H]+ |
|---|---|---|---|
| 56 | 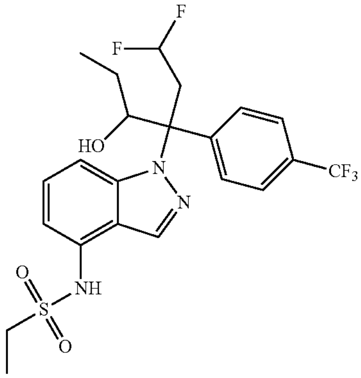 [SMILES: CCC(O)C(CC(F)F)(c1ccc(C(F)(F)F)cc1)n1ncc2c(NS(=O)(=O)CC)cccc21] | N-(1-(1,1-difluoro-4-hydroxy-3-(4-(trifluoromethyl)phenyl)hexan-3-yl)-1H-indazol-4-yl)ethanesulfonamide (Diastereomer D) | 506.1 |
| 57 | 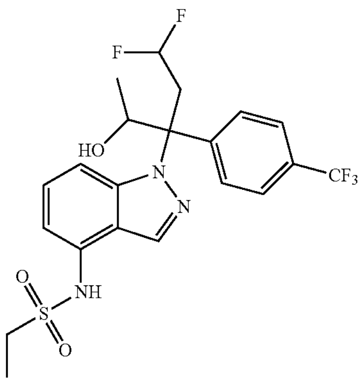 [SMILES: CCS(=O)(=O)Nc1cccc2c1cnn2C(CC(F)F)(c1ccc(C(F)(F)F)cc1)C(C)O] | N-(1-(1,1-difluoro-4-hydroxy-3-(4-(trifluoromethyl)phenyl)pentan-3-yl)-1H-indazol-4-yl)ethanesulfonamide (Diastereomer C) | 492.1 |
| 58 | | N-(1-(1,1-difluoro-4-hydroxy-3-(4-(trifluoromethyl)phenyl)pentan-3-yl)-1H-indazol-4-yl)ethanesulfonamide (Diastereomer D) | 492.1 | or a pharmaceutically acceptable salt thereof.

As used herein except where noted, "alkyl" is intended to include both branched- and straight-chain saturated aliphatic hydrocarbon groups having the specified number of carbon atoms. The term "cycloalkyl" means carbocycles containing no heteroatoms. Examples of cycloalkyl include cyclopropyl, cyclobutyl, cyclopentyl, cyclohexyl, cycloheptyl, decahydronaphthyl and the like. Commonly used abbreviations for alkyl groups are used throughout the specification, e.g. methyl may be represented by conventional abbreviations including "Me" or $CH_3$ or a symbol that is an extended bond without defined terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, secand t-butyl, n- and isopropyl, ethyl and methyl. "$C_{1-4}$ alkyl" means n-, iso-, sec- and t-butyl, n- and isopropyl, ethyl and methyl. If no number is specified, 1-10 carbon atoms are intended for linear or branched alkyl groups. The phrase "$C_{1-6}$ alkyl, wherein the alkyl group may be unsubstituted or substituted with 1-3 fluorine atoms" refers to alkyl groups having 0, 1, 2 or 3 fluorine atoms attached to one or more carbon atoms. The group "$CF_3$", for example, is a methyl group having three fluorine atoms attached the same carbon atom.

"Alkenyl" unless otherwise indicated, means carbon chains which contain at least one carbon-carbon double bond, and which may be linear or branched or combinations thereof. Examples of alkenyl include, but are not limited to, vinyl, allyl, isopropenyl, pentenyl, hexenyl, heptenyl, 1-propenyl, 2-butenyl, 2-methyl-2-butenyl, and the like. The term "cycloalkenyl" means carbocycles containing no heteroatoms having at least one carbon-carbon double bond.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

"Aryl" unless otherwise indicated, means mono- and bicyclic aromatic rings containing 6-12 carbon atoms. Examples of aryl include, but are not limited to, phenyl, naphthyl, indenyl and the like. "Aryl" also includes monocyclic rings fused to an aryl group. Examples include tetrahydronaphthyl, indanyl and the like. The preferred aryl is phenyl.

"Heteroaryl" unless otherwise indicated, means a mono- or bicyclic aromatic ring or ring system having 5 to 10 atoms and containing at least one heteroatom selected from O, S and N. Examples include, but are not limited to, pyrrolyl, isoxazolyl, isothiazolyl, pyrazolyl, pyridyl, pyridinyl, oxazolyl, oxadiazolyl, thiadiazolyl, thiazolyl, imidazolyl, triazolyl, tetrazolyl, furanyl, triazinyl, thienyl, pyrimidyl, pyrimidinyl, pyridazinyl, pyrazinyl, and the like. Heteroaryl also includes aromatic heterocyclic groups fused to heterocycles that are non-aromatic or partially aromatic, and aromatic heterocyclic groups fused to cycloalkyl rings. Additional examples of heteroaryls include, but are not limited to, indazolyl, thienopyrazolyl, imidazopyridazinyl, pyrazolopyrazolyl, pyrazolopyridinyl, imidazopyridinyl and imidazothiazolyl. Heteroaryl also includes such groups in charged form, e.g., pyridinium. In an embodiment, heteroaryl is oxadiazolyl, pyrazolyl, oxazolyl, pyridinyl and imidazolyl "Heterocyclyl", unless otherwise indicated, means a 4-, 5- or 6-membered monocyclic saturated ring containing at least one heteroatom selected from N, S and O, in which the point of attachment may be carbon or nitrogen. Examples of "heterocyclyl" include, but are not limited to, azetidinyl, pyrrolidinyl, piperidinyl, piperazinyl, morpholinyl, oxazolidinyl, imidazolidinyl, 2,3-dihydrofuro(2,3-b)pyridyl, benzoxazinyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils). Heterocyclyl moreover includes such moieties in charged form, e.g., piperidinium. In an embodiment, heterocyclyl is pyrrolidinyl, piperidinyl, piperazinyl, morpholinyl and oxazolidinyl.

"Halogen (or halo)" unless otherwise indicated, includes fluorine (fluoro), chlorine (chloro), bromine (bromo) and iodine (iodo). In one embodiment, halo is fluorine or chlorine.

By "oxo" is meant the functional group "=O" which is an oxygen atom connected to the molecule via a double bond, such as, for example, (1) "C=(O)", that is a carbonyl group; (2) "S=(O)", that is, a sulfoxide group; and (3) "N=(O)", that is, an N-oxide group, such as pyridyl-N-oxide.

Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

When any variable (e.g., R, $R^x$, etc.) occurs more than one time in any constituent or in Formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

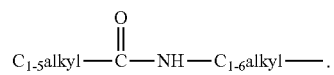

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Where a substituent or variable has multiple definitions, it is understood that the substituent or variable is defined as being selected from the group consisting of the indicated definitions.

Optical Isomers—Diastereoisomers—Geometric Isomers—Tautomers—Atropisomers:

Compounds of structural Formula I may contain one or more asymmetric centers and can thus occur as racemates and racemic mixtures, single enantiomers, diastereoisomeric mixtures and individual diastereoisomers. The present invention is meant to comprise all such isomeric forms of the compounds of structural Formula I.

Compounds of structural Formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer or isomers of a compound of the general structural Formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of structural Formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural Formula I. For example, different isotopic forms of hydrogen (H) include protium ($^1H$) and deuterium ($^2H$, also denoted as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formula I, can be prepared without undue experimentation by conventional techniques well known to those skilled in the art or by processes analogous to those described in the Schemes and Examples herein using appropriate isotopically-enriched reagents and/or intermediates. Thus, the present invention covers isotopically-enriched compounds, including deuterated compounds.

The present invention includes all stereoisomeric forms of the compounds of the Formula I. Centers of asymmetry that are present in the compounds of Formula I can all independently of one another have S configuration or R configuration. The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the Formula I or at the stage of an intermediate during the synthesis. The present invention also includes all tautomeric forms of the compounds of Formula I.

The present invention includes all atropisomer forms of the compounds of Formula I. Atropisomers are stereoisomers resulting from hindered rotation about single bonds where the steric strain barrier to rotation is high enough to allow for the isolation of the conformers. Atropisomers display axial chirality. Separation of atropisomers is possibly by chiral resolution methods such as selective crystallization.

Salts:

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates and the hydrates of the compounds of structural Formula I are included in the present invention as well.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts. The terms "pharmaceutically acceptable salt(s)" and "physiologically acceptable salt(s)" are intended to have the same meaning and are used interchangeably herein.

In an embodiment, the invention concerns compounds of Formula I:

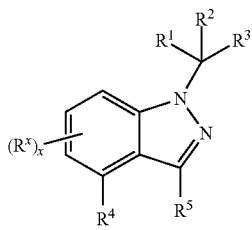

or a pharmaceutically acceptable salt thereof, wherein
Each $R^x$ is independently H or halo;
Each R is independently H or $C_1$-$C_6$ alkyl;
$R^1$ is $C_1$-$C_6$ alkyl, or $C(O)NRR^6$;
  wherein said alkyl is optionally substituted with one to three $CF_3$, OR, CN or halo substituents;
$R^2$ is $C_1$-$C_6$ alkyl, said alkyl is optionally substituted with one to three OR, CN or halo substituents;
$R^3$ is aryl-$X_t$;
$R^4$ is —$NR^6S(O)_2R^8$;
$R^5$ is H or $C_1$-$C_6$ alkyl;
Each $R^6$ is independently H, $C_1$-$C_6$ alkyl, said alkyl may be optionally substituted with aryl, heteroaryl or heterocyclyl;

Each $R^8$ is independently $C_1$-$C_6$ alkyl, $C_3$-$C_{10}$ cycloalkyl or aryl, said alkyl, cycloalkyl and aryl are optionally substituted with 1 to 3 $C_3$-$C_{10}$ cycloalkyl or halo substituents;
Each X is independently halo, CN, $CF_3$, or $SF_5$;
t is 1, 2 or 3;
x is 0, 1, 2 or 3.

In an embodiment, $R^x$ is H or halo.

In an embodiment, $R^1$ is $C_1$-$C_6$ alkyl or $C(O)NH_2$, said alkyl is optionally substituted with one to three $CF_3$, OR, CN, or halo substituents. In an embodiment, $R^1$ is $C_1$-$C_6$ alkyl or $C(O)NH_2$, said alkyl is optionally substituted with one to three OR, or halo substituents. In an embodiment, $R^1$ is $C_1$-$C_6$ alkyl, said alkyl is optionally substituted with one to three OR, or halo substituents.

In an embodiment, $R^2$ is $C_1$-$C_6$ alkyl, said alkyl is optionally substituted with one to three halo substituents. In an embodiment, $R^2$ is ethyl substituted with one to three halo atoms at the terminal carbon. In a further embodiment, $R^2$ is ethyl, $CH_2CF_2H$ or $CH_2CF_3$. In another embodiment, $R^2$ is ethyl.

In an embodiment, $R^3$ is aryl —$X_t$. In an embodiment, $R^3$ is phenyl-$X_t$. In an embodiment, t is the integer 1. In an embodiment, $R^3$ is

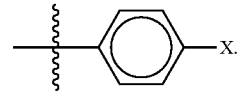

In an embodiment, $R^4$ is $NR^6S(O)_2R^8$. In an embodiment, $R^4$ is $NHS(O)_2R^8$. In another embodiment, $R^4$ is $NHS(O)_2R^8$ and $R^8$ is $C_1$-$C_6$ alkyl.

In an embodiment, $R^5$ is H or $C_1$-$C_6$ alkyl.

In an embodiment, $R^6$ is H or $C_1$-$C_6$ alkyl.

In an embodiment, $R^8$ is $C_1$-$C_6$ alkyl or $C_3$-$C_{10}$ cycloalkyl, said alkyl and cycloalkyl may be optionally substituted with one to three $C_3$-$C_{10}$ cycloalkyl or halo substituents. In an embodiment, $R^8$ is $C_1$-$C_6$ alkyl, said alkyl may be optionally substituted with one to three $C_3$-$C_{10}$ cycloalkyl or halo substituents.

In an embodiment, the invention concerns compounds of Formula II:

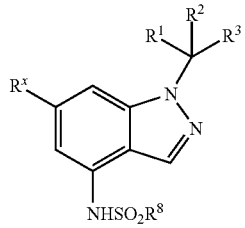

or a pharmaceutically acceptable salt thereof, wherein
Each $R^x$ is H or halo;
Each R is independently H or $C_1$-$C_6$ alkyl;
$R^1$ is $C_1$-$C_6$ alkyl, or $C(O)NRR^6$;
  wherein said alkyl is optionally substituted with one to three $CF_3$, OR, CN, or halo substituents;
$R^2$ is $C_1$-$C_6$ alkyl, said alkyl is optionally substituted with one to three OR, CN or halo substituents;
$R^3$ is phenyl-$X_t$;
Each $R^6$ is independently H, $C_1$-$C_6$ alkyl, said alkyl may be optionally substituted with aryl, heteroaryl or heterocyclyl;

Each $R^8$ is independently $C_1$-$C_6$ alkyl, said alkyl is optionally substituted with one to three $C_3$-$C_{10}$ cycloalkyl or halo substituents;

Each X is independently halo, CN, $CF_3$, or $SF_5$;

t is 1 or 2.

Another embodiment is a compound of Formula I or II or a pharmaceutically acceptable salt thereof wherein $R^x$ is H or halo; R is H or $C_1$-$C_6$ alkyl; $R^1$ is $C_1$-$C_6$ alkyl, which is optionally substituted by —OH, or C(O)NR$R^6$; $R^2$ is $C_1$-$C_6$ alkyl, which is optionally substituted by halo; $R^3$ is phenyl-$CF_3$; $R^6$ is independently H, $C_1$-$C_6$ alkyl; and $R^8$ is independently $C_1$-$C_6$ alkyl.

The present invention also relates to processes for the preparation of the compounds of Formula I which are described in the following and by which the compounds of the invention are obtainable.

The compounds of the Formula I according to the invention competitively antagonize the aldosterone receptor (MR) and they may be therefore useful agents for the therapy and prophylaxis of disorders related to increased aldosterone levels. The ability for the compounds of Formula I to antagonize MR can be examined, for example, in the activity assay described herein below.

Although other aldosterone antagonists have been previously disclosed, the instant invention is directed to compounds that have shown some unexpected properties, such as improved photo stability, increased potency, improved selectivity towards other nuclear hormone receptors, reduced inhibition of cytochrome P450 enzymes, improved PXR selectivity and/or good metabolic stability and PK profiles. For example, Compound 31, which has a fluorine to the indazole ring, had excellent metabolic stability in liver microsome and hepatocytes of multiple animal species. Moreover, Compound 31 exhibited a good PK profile in rats One aspect of the invention that is of interest relates to a compound in accordance with Formula I or a pharmaceutically acceptable salt thereof for the possible use in a method of treatment of the human or animal body by therapy.

Another aspect of the invention that is of interest relates to a compound in accordance with Formula I or a pharmaceutically acceptable salt thereof for the possible use as an anti-hypertensive agent in a human or animal.

Another aspect of the invention that is of interest is a possible method of treating cardiovascular disease, heart failure, hypertension, atherosclerosis, primary hyperaldosteronism or a related condition in a human or animal in need of such treatment comprising administering a therapeutically effective amount of a compound of Formula I or a pharmaceutically acceptable salt thereof.

Another aspect of the invention that is of interest relates to a possible method of treating metabolic syndrome in a mammal in need of such treatment, comprising administering a therapeutically effective amount of a compound of Formula I or a pharmaceutically acceptable salt thereof.

Another aspect of the invention that is of interest is a possible method of treating retinopathy in a patient in need of such treatment comprising administering a therapeutically effective amount of a compound of Formula I or a pharmaceutically acceptable salt thereof.

Another aspect of the invention that is of interest is a possible method of treating obstructive sleep apnea in a patient in need of such treatment comprising administering a therapeutically effective amount of a compound of Formula I or a pharmaceutically acceptable salt thereof. Another aspect of the invention that is of interest is a method of treating obstructive sleep apnea, which is associated with cardiac diseases, in a patient in need of such treatment comprising administering a therapeutically effective amount of a compound of Formula I or a pharmaceutically acceptable salt thereof.

Another aspect of the invention that is of interest relates to a possible method of treating a physiological or pathologic disease, selected from including Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels in a human patient in need of such treatment comprising administering to the patient a therapeutically effective amount of a compound of Formula I or a pharmaceutically acceptable salt thereof Another aspect of the invention that is of interest is a possible method of treating chronic kidney disease, diabetic nephropathy or renal failure in a patient in need of such treatment comprising administering a therapeutically effective amount of a compound of Formula I or a pharmaceutically acceptable salt thereof.

Compounds of the invention may be useful for treating both primary (essential) and secondary hypertension. Hypertensive conditions include, but are not limited to, systolic hypertension, isolated systolic hypertension, diastolic hypertension, isolated diastolic hypertension, renovascular hypertension, endocrine disorder hypertension (including hyperaldosteronism and pheochromocytoma), malignant hypertension, resistant hypertension, pulmonary hypertension, hypertension in obesity/diabetes/metabolic syndrome, hypertension in heart failure, hypertension in pregnancy, and accelerated hypertension, and prehypertension associated with any of these conditions.

Additionally, another aspect of the invention is a possible method of treating hypertension in an obese animal or human.

Additionally, another aspect of the invention is a possible method of treating hypertension in a diabetic animal or human.

Additionally, another aspect of this invention is a possible use of a compound of Formula I or a pharmaceutically acceptable salt thereof for the preparation of a medicament useful for the treatment or prevention of one or more conditions selected form the group consisting of cardiovascular disease, heart failure, hypertension, atherosclerosis, primary hyperaldosteronism, metabolic syndrome, renal failure, Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels.

The compounds of the Formula I and their pharmaceutically acceptable salts can be administered to animals, preferably to mammals, and in particular to humans, as pharmaceuticals by themselves, in mixtures with one another or in the form of pharmaceutical preparations. As used herein, "animals" also includes companion animals such as cats and dogs. In an embodiment of the invention, the compounds of Formula I and their pharmaceutically acceptable salts can be administered to humans or companion animals, such as cats and dogs, for the prevention or treatment of a medical condition or disease. The term "patient" includes animals, preferably mammals and especially humans, as well as companion animals such as cats and dogs, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

A subject of the present invention therefore also are the compounds of the Formula I and their pharmaceutically acceptable salts for use as pharmaceuticals, their use for antagonizing mineralocorticoid receptors and in particular their use in the therapy and prophylaxis of the abovementioned syndromes as well as their use for preparing medicaments for these purposes.

A therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention of myocardial infarction.

Furthermore, a subject of the present invention are pharmaceutical preparations (or pharmaceutical compositions) which comprise as active component an effective dose of at least one compound of the Formula I and/or a pharmaceutically acceptable salt thereof and a customary pharmaceutically acceptable carrier, i.e., one or more pharmaceutically acceptable carrier substances and/or additives.

Thus, subjects of the invention are, for example, said compound and its pharmaceutically or pharmaceutically acceptable salts for use as a pharmaceutical, pharmaceutical preparations which comprise as an active component a therapeutically effective dose of said compound and/or a pharmaceutically acceptable salt thereof and a customary pharmaceutically acceptable carrier, and the uses of said compound and/or a pharmaceutically acceptable salt thereof in the therapy or prophylaxis of the abovementioned syndromes as well as their use for preparing medicaments for these purposes.

The pharmaceutical compositions according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of the Formula I and/or its pharmaceutically acceptable salts in the pharmaceutical preparations normally is from 0.2 to 700 mg, preferably from 1 to 500 mg, per dose, but depending on the type of the pharmaceutical preparation it can also be higher. The pharmaceutical preparations usually comprise 0.5 to 90 percent by weight of the compounds of the Formula I and/or their pharmaceutically acceptable salts. The preparation of the pharmaceutical preparations can be carried out in a manner known per se. For this purpose, one or more compounds of the Formula I and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the Formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of the Formula I to be administered and/or of a pharmaceutically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of the Formula I. In general, a daily dose of approximately 0.01 to 100 mg/kg, preferably 0.01 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose.

The compounds of the Formula I bind to the mineralocorticoid receptor and antagonize the biological effects of aldosterone and cortisol. On account of this property, apart from use as pharmaceutically active compounds in human medicine and veterinary medicine, they can also be employed as a scientific tool or as aid for biochemical investigations in which such an effect on the mineralocorticoid receptor is intended, and also for diagnostic purposes, for example in the in vitro diagnosis of cell samples or tissue samples. The compounds of the Formula I and salts thereof can furthermore be employed, as already mentioned above, as intermediates for the preparation of other pharmaceutically active compounds.

The above-mentioned compounds are also of use in combination with other (i.e., a second) pharmacologically active compounds. Additional (or second) active compounds that may be used in combination with the compounds of the instant invention, either co-administered or in a fixed combination, include, but are not limited to, angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan, valsartan, candesartan, olmesartan, telmesartan), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S), 5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (including loop diuretics (e.g., furosemide, torsemide), thiazides diuretics (e.g., chlorothiazide, chlorothalidone, hydrochlorothiazide), sulfonamides (e.g, Indapemide, Xipemide), Carbonic anhydrase inhibitors (e.g., acetazolamide, methazolamide), arginine vasopressin receptor antagonists, and Na—H exchanger inhibitors), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., niacin, HMG Co-A reductase inhibitors), metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, LY-818, and compounds disclosed in WO02/08188, WO2004/020408, and WO2004/020409.

(b) biguanides, such as metformin and phenformin;

(c) protein tyrosine phosphatase-1B (PTP-1B) inhibitors;

(d) dipeptidyl peptidase-IV (DPP-4) inhibitors, such as sitagliptin, saxagliptin, vildagliptin, linagliptin, dutogliptin, gemigliptin and alogliptin;

(e) insulin or insulin mimetics;

(f) sulfonylureas such as tolbutamide, glimepiride, glipizide, and related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPARa agonists, such as fenofibric acid derivatives (gemfibrozil, clofibrate, fenofibrate and bezafibrate), (v) cholesterol absorption inhibitors, such as ezetimibe, (vi) acyl CoA:cholesterol acyltransferase (ACAT) inhibitors, such as avasimibe, (vii) CETP inhibitors, such as torcetrapib, anacetrapib, and dalcetrapib, and (viii) phenolic antioxidants, such as probucol;

(i) PPARα/γ dual agonists, such as muraglitazar, tesaglitazar, farglitazar, and JT-501;

(j) PPARδ agonists, such as those disclosed in WO97/28149;

(k) anti-obesity compounds, such as fenfluramine, dexfenfluramine, phentiramine, subitramine, orlistat, neuropeptide YY5 inhibitors, MC4R agonists, cannabinoid receptor 1 (CB-1) antagonists/inverse agonists (e.g., rimonabant and taranabant), and $\beta_3$ adrenergic receptor agonists;

(l) ileal bile acid transporter inhibitors;

(m) agents intended for use in inflammatory conditions, such as aspirin, non-steroidal anti-inflammatory drugs, glucocorticoids, azulfidine, and cyclooxygenase-2 (Cox-2) selective inhibitors;

(n) glucagon receptor antagonists;

(o) GLP-1;

(p) GIP-1;

(q) GLP-1 analogs and derivatives, such as exendins, (e.g., exenatide and liruglatide), and (r) 11β-hydroxysteroid dehydrogenase-1 (HSD-1) inhibitors.

One or more additional active agents may be administered with the compounds described herein. The additional active agent or agents can be lipid modifying compounds or agents having other pharmaceutical activities, or agents that have both lipid-modifying effects and other pharmaceutical activities. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (see U.S. Pat. No. 4,342,767), simvastatin (see U.S. Pat. No. 4,444,784), dihydroxy open-acid simvastatin, particularly the ammonium or calcium salts thereof, pravastatin, particularly the sodium salt thereof (see U.S. Pat. No. 4,346,227), fluvastatin particularly the sodium salt thereof (see U.S. Pat. No. 5,354,772), atorvastatin, particularly the calcium salt thereof (see U.S. Pat. No. 5,273,995), pitavastatin also referred to as NK-104 (see PCT international publication number WO 97/23200) and rosuvastatin, also known as CRESTOR®; see U.S. Pat. No. 5,260,440); HMG-CoA synthase inhibitors; squalene epoxidase inhibitors; squalene synthetase inhibitors (also known as squalene synthase inhibitors), acyl-coenzyme A: cholesterol acyl-transferase (ACAT) inhibitors including selective inhibitors of ACAT-1 or ACAT-2 as well as dual inhibitors of ACAT-1 and -2; microsomal triglyceride transfer protein (MTP) inhibitors; endothelial lipase inhibitors; bile acid sequestrants; LDL receptor inducers; platelet aggregation inhibitors, for example glycoprotein IIb/IIIa fibrinogen receptor antagonists and aspirin; human peroxisome proliferator activated receptor gamma (PPAR-gamma) agonists including the compounds commonly referred to as glitazones for example pioglitazone and rosiglitazone and, including those compounds included within the structural class known as thiazolidine diones as well as those PPAR-gamma agonists outside the thiazolidine dione structural class; PPAR-alpha agonists such as clofibrate, fenofibrate including micronized fenofibrate, and gemfibrozil; dipeptidyl peptidase-IV (DPP-4) inhibitors, such as sitagliptin, saxagliptin, vildagliptin, linagliptin, dutogliptin, gemigliptin and alogliptin; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; diuretics (including Loop diuretics (e.g., furosemide, torsemide), thiazides diuretics (e.g., chlorothiazide, chlorothalidone, hydrochlorothiazide), sulfonamides (e.g, indapemide, xipemide), carbonic anhydrase inhibitors (e.g., acetazolamide, methazolamide), arginine vasopressin receptor antagonists, and Na—H exchanger inhibitors), sympatholitics, endothelin antagonists; agents that enhance ABCA1 gene expression; cholesteryl ester transfer protein (CETP) inhibiting compounds, including anacetrapib; 5-lipoxygenase activating protein (FLAP) inhibiting compounds, 5-lipoxygenase (5-LO) inhibiting compounds, farnesoid X receptor (FXR) ligands including both antagonists and agonists; liver X Receptor (LXR)-alpha ligands, LXR-beta ligands, bisphosphonate compounds such as alendronate sodium; cyclooxygenase-2 inhibitors such as rofecoxib and celecoxib; and compounds that attenuate vascular inflammation.

The compounds of Formula I can be synthesized in accordance with the general schemes provided below where $R^1$, $R^2$, and $R^9$ are defined as above (unless otherwise indicated), taking into account the specific examples that are provided. Throughout the synthetic schemes and examples, abbreviations are used with the following meanings unless otherwise indicated:
ABCA1=adenosyltriphosphate-binding cassette-family A1
Ac=acetate, acetyl;
ACN is acetonitrile
AIBN is 2,2'-Azobis(2-methylpropionitrile)
aq. is aqueous;
Ar is Aryl;
Bn is benzyl;
Boc is tertbutylcarbamoyl;
br is broad;
Bu is butyl;
CDI is carbonyl diimidazole;
celite is Celite® diatomaceous earth;
CHO is Chinese hamster ovary
cpm is counts per minute;
° C. is degrees Celsius δ is chemical shift;
$^cPr$ is cyclopropyl;
DCM is dichloromethane;
DEA is diethylamine
DIBALH is diisobutylaluminium hydride;
DMA is dimethylacetamide
DMF is N,N-dimethylformamide;
DMSO is dimethyl sulfoxide;
EA is ethyl acetate;
EDC or EDCI is N-(3-dimethylaminopropyl)-N'-ethylcarbodiimide hydrochloride;
EDTA is ethylendiamine tetraacetic acid;
ES-MS is electrospray ion-mass spectroscopy;
Et is ethyl;
$Et_2O$ is diethyl ether;
EtOH is ethanol,
EtOAc is ethyl acetate;
FBS is fetal bovine serum
FXR is farnesoid X receptor;
halo is a halogen (preferably fluorine or chlorine),
HATU is O-(7-azabenzotriazol-1-yl)-N,N,N',N'-tetramethyluronium hexafluorophosphate;
HetAr or HAR is Heteroaryl;
HMG-CoA is 3-hydroxy-3-methyl-glutaryl coenzyme A;
HMPA is hexamethylphosphoramide
$^1$HNMR is proton nuclear magnetic resonance;
HOBt or HOBT is 1-hydroxybenzotriazole
HPLC is high performance liquid chromatography;
Hz is hertz;
i is Iso;
IP is the inflection point for a given dose-response titration curve;
kg is kilogram;
LC/MS is Liquid chromatography/Mass Spectroscopy;
LiHMDS is lithium bis(trimethylsilyl)amide;
$LTB_4$ is leukotriene $B_4$;
LXR is liver X receptor;
M is molar;
Me is methyl;
μg is microgram;
MeCN is acetonitrile;
MeOH is methanol;
MHz is megahertz;
mm is millimeter;
μL is microliter;
mM is milimolar;
μM is micromolar;
mmol is milimoles;
Ms is methanesulfonyl
MS is mass spectrum, and a mass spectrum obtained by ES-MS may be denoted herein by "ES";
MsCl is methanesulfonyl chloride
mw is microwave;
m/z is mass to charge ratio;
n is normal;
NaHMDS is sodium hexamethyldisilazide;
NBS is N-bromosuccinimide
nm is nanometer;
NMM is N-methylmorpholine;
nPr is n-propyl;
p is para;
$PdCl_2(PPh_3)_2$ is bis(trisphenylphosphine)palladium(II) dichloride;
$Pd_2(dba)_3$ is tris(dibenzylideneacetone)dipalladium;
$Pd(PPh_3)_4$ is palladium tetrakis(triphenylphosphine);

PE/EA is petroleum ether/ethyl acetate;
Ph is phenyl;
PPARα is peroxisome proliferator activated receptor alpha;
Pr is propyl;
Prep HPLC is preparative HPLC;
Pt/C is platinum carbon;
PXR is Pregnane X receptor;
RP HPLC is Reverse Phase High Performance Liquid Chromatography;
rt is room temperature;
Rt is Retention time;
SCF chromatography is Super-Critical Fluid Chromatography;
sec is secondary;
$^t$Bu is tert-butyl;
$^t$BuOH is tert-butanol;
TEA is triethyl amine;
tert is tertiary;
TFA is trifluoroacetic acid;
THF is tetrahydrofuran;
TLC is thin layer chromatography;
TMSCN is trimethylsilyl cyanide;
U is units
UV is ultraviolet.

SCHEMES

Reaction Schemes 1-9 illustrate the methods employed in the synthesis of the compounds of Formula I. All abbreviations are as defined above unless indicated otherwise. In the Schemes, all substituents are as defined above in Formula I unless indicated otherwise.

Synthetic methods for preparing the compounds of the present invention are illustrated in the following Schemes and Examples. Starting materials are commercially available or may be made according to procedures known in the art or as illustrated herein.

SCHEME 1

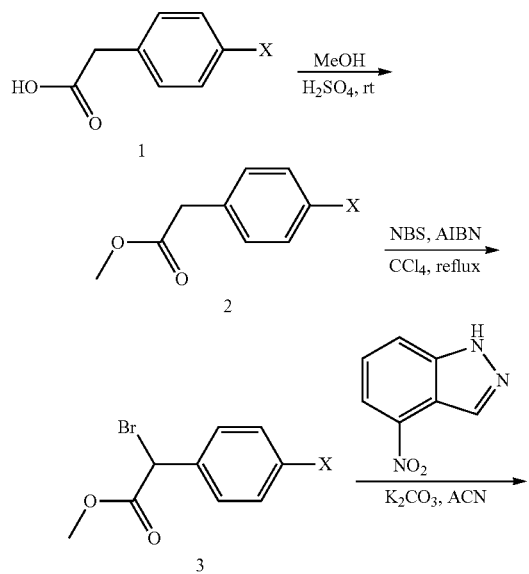

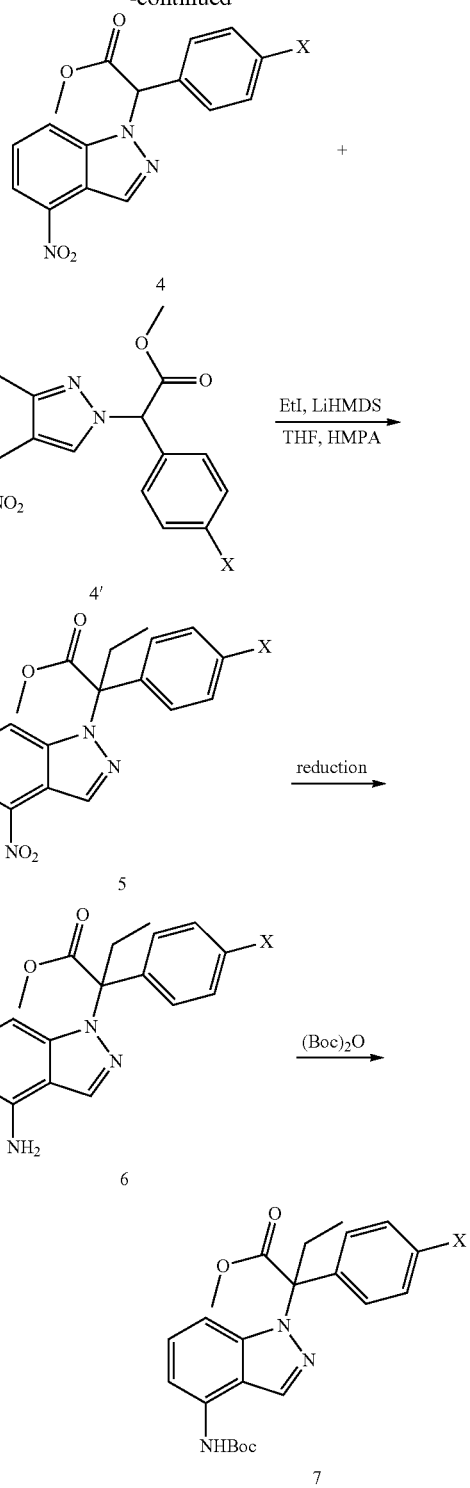

As shown in SCHEME 1, the phenylacetic acid starting material (X=Cl, CF$_3$, Br, etc.) can be converted to ester 2 using standard conditions and subsequently brominated at the alpha position to give bromide 3. Reaction of 3 with 1H-indazole or its 6-F analog afforded a mixture of alkylated products 4 and 4'. Alkylation of the resulting anion intermediate from 4 gave compound 5, which is reduced and protected to give Boc intermediate 7.

SCHEME 2

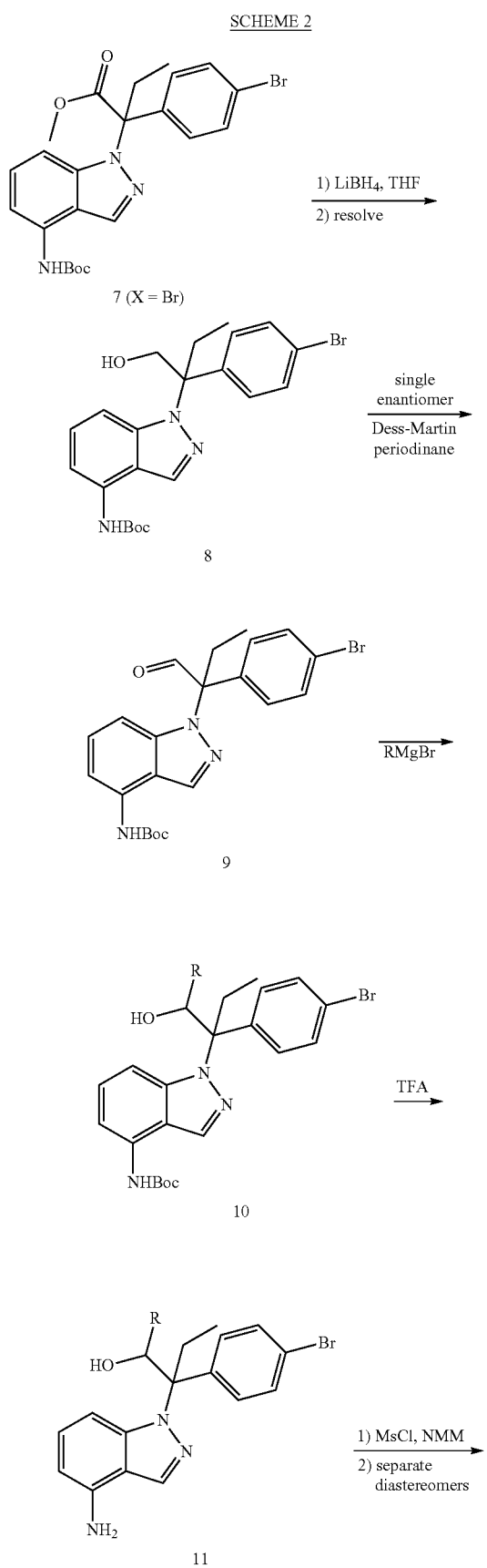

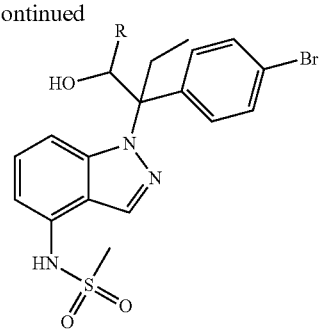

As shown in SCHEME 2, reduction of ester 7 (X=Br) afforded racemic alcohol 8, which was resolved to give two enantiomers using chiral column chromatography. Each enantiomer of 8 was carried forward using the same procedure individually. Oxidation of 8 gave aldehyde 9, which was treated with Grignard reagent to give secondary alcohol 10 (R=$C_1$-$C_5$ alkyl or $C_3$-$C_{10}$ cycloalkyl, which may be optionally substituted with halo, OR and $C_1$-$C_6$ alkyl). Subsequent deprotection of Boc and formation of sulfonamide afforded 12 as a diastereomeric mixture from each enantiomers of 8. Separation using chiral SCF chromatography provided pure individual diastereomers of 12.

SCHEME 3

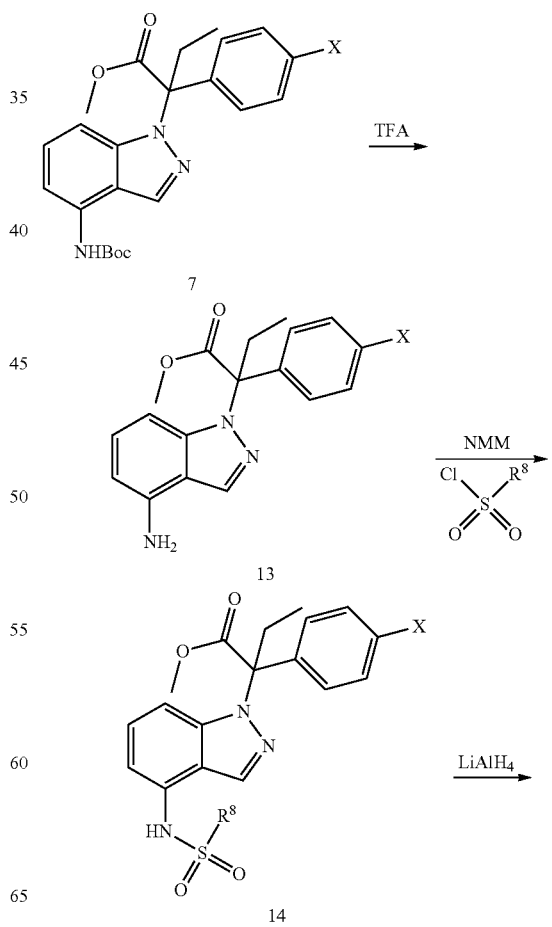

-continued

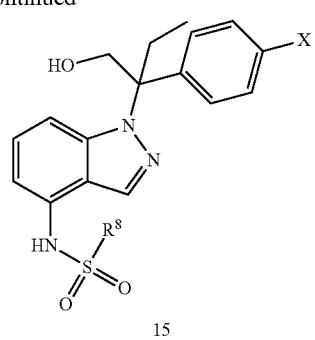

As shown in SCHEME 3, for enantiomerically pure 7, deprotection of the Boc produced 13. Subsequent sulfonlyation and reduction of ester to alcohol gave the enantiomerically pure primary alcohol 15. Starting with racemic compound 6 and following the procedures of SCHEME 3, racemic 15 was obtained.

As shown in SCHEME 4, the ester 14 (X=CF₃, halo, etc.) was hydrolyzed to give acid 16. Amide formation reaction, such as standard peptide coupling conditions, produced the primary amide 17.

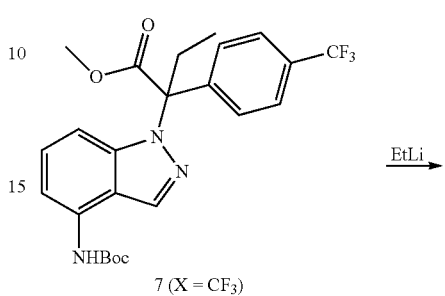

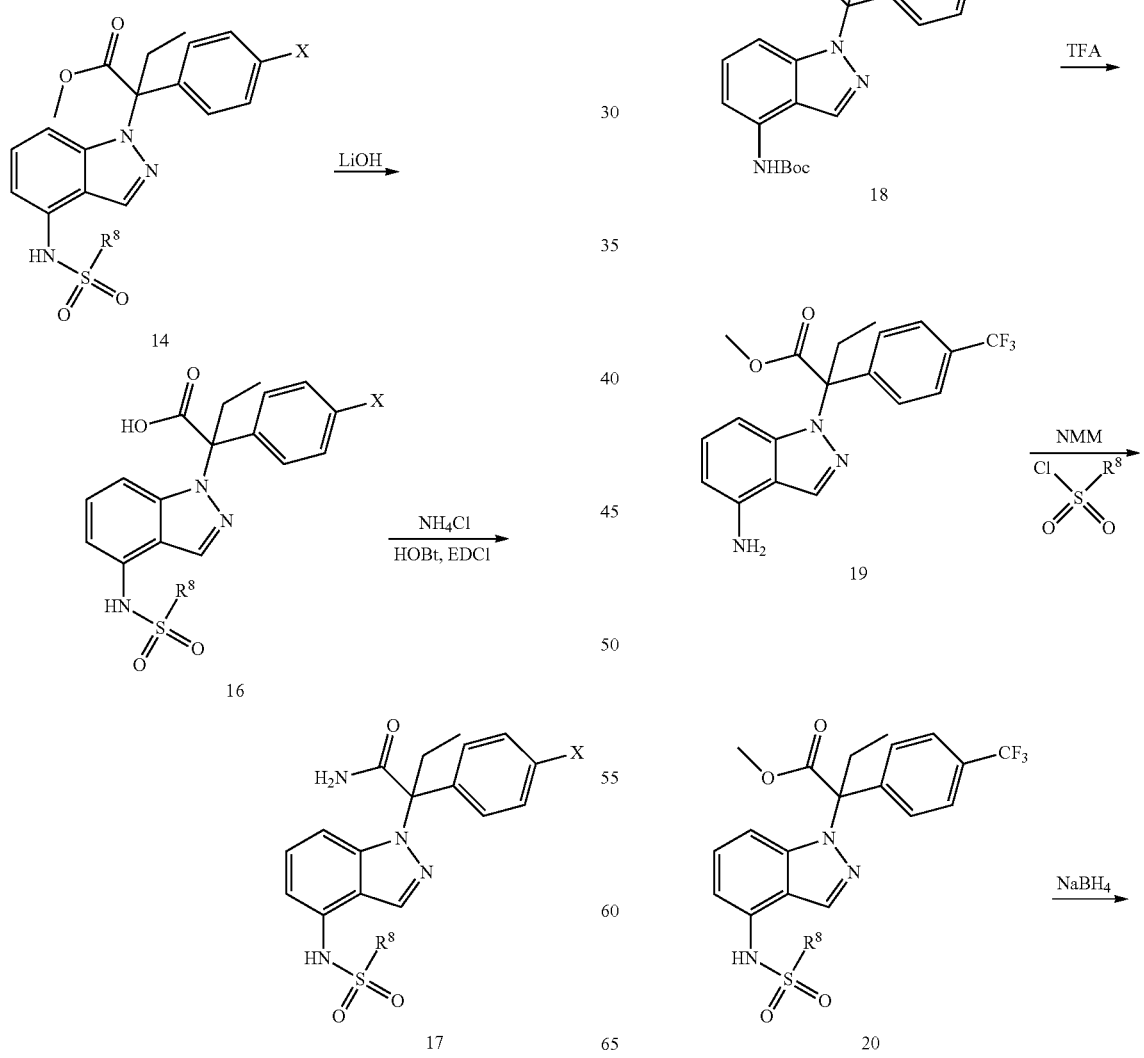

-continued

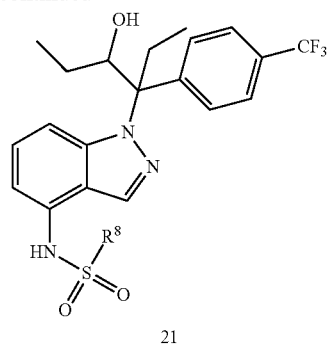

21

In SCHEME 5, the ester 7 can be converted to ethyl ketone 18 using ethyl lithium. Deprotection of Boc afforded aniline 19, which was sulfonylated to give 20. Reduction of ketone 20 to alcohol produced secondary alcohol 21. The diastereomeric mixture of 4 isomers of 21 could be separated by chiral column chromatography into individual diastereomers. If each enantiomer of 7 was individually carried through the method of SCHEME 5, the resulting two separate mixtures of diastereomers 21 could be separated to give enantiomerically pure diastereomers of 21.

SCHEME 6

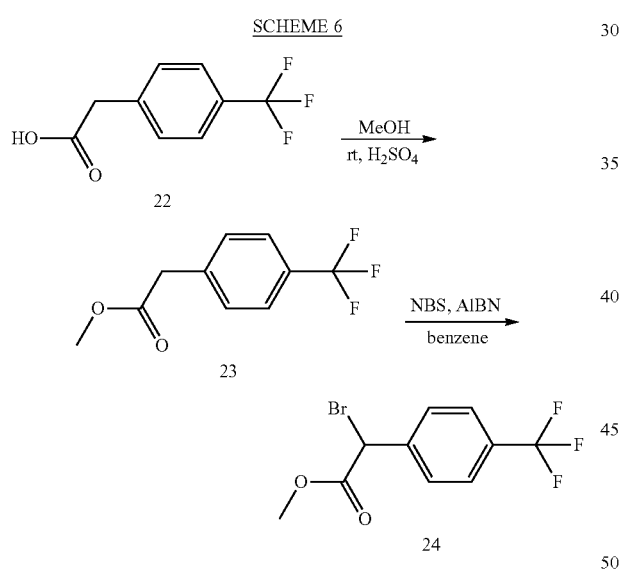

As shown in SCHEME 6, the phenylacetic acid starting material 22 was converted to ester 23 using standard conditions and subsequently brominated at the alpha position to give bromide 24.

SCHEME 7

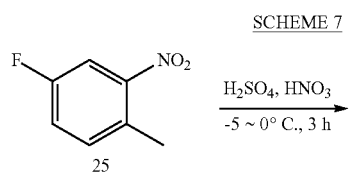

-continued

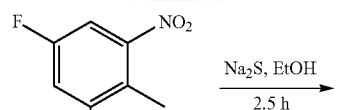

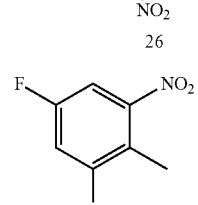

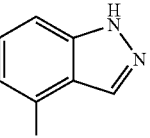

As shown in SCHEME 7, nitrotoluene 25 was nitrated to give dinitrotoluene 26, which was reduced to afford nitroaniline 27. The latter was cyclized to indazole 28 using sodium nitrite.

SCHEME 8

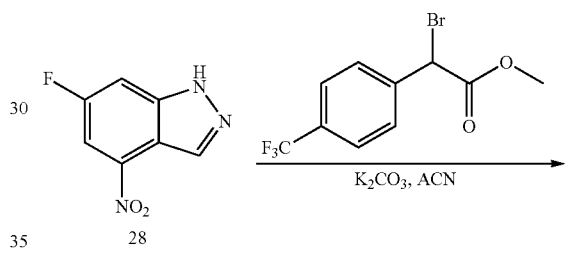

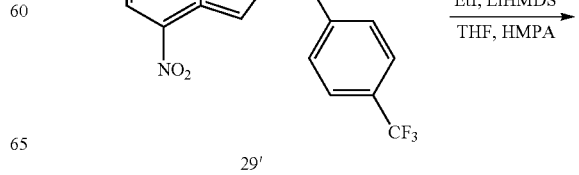

29'

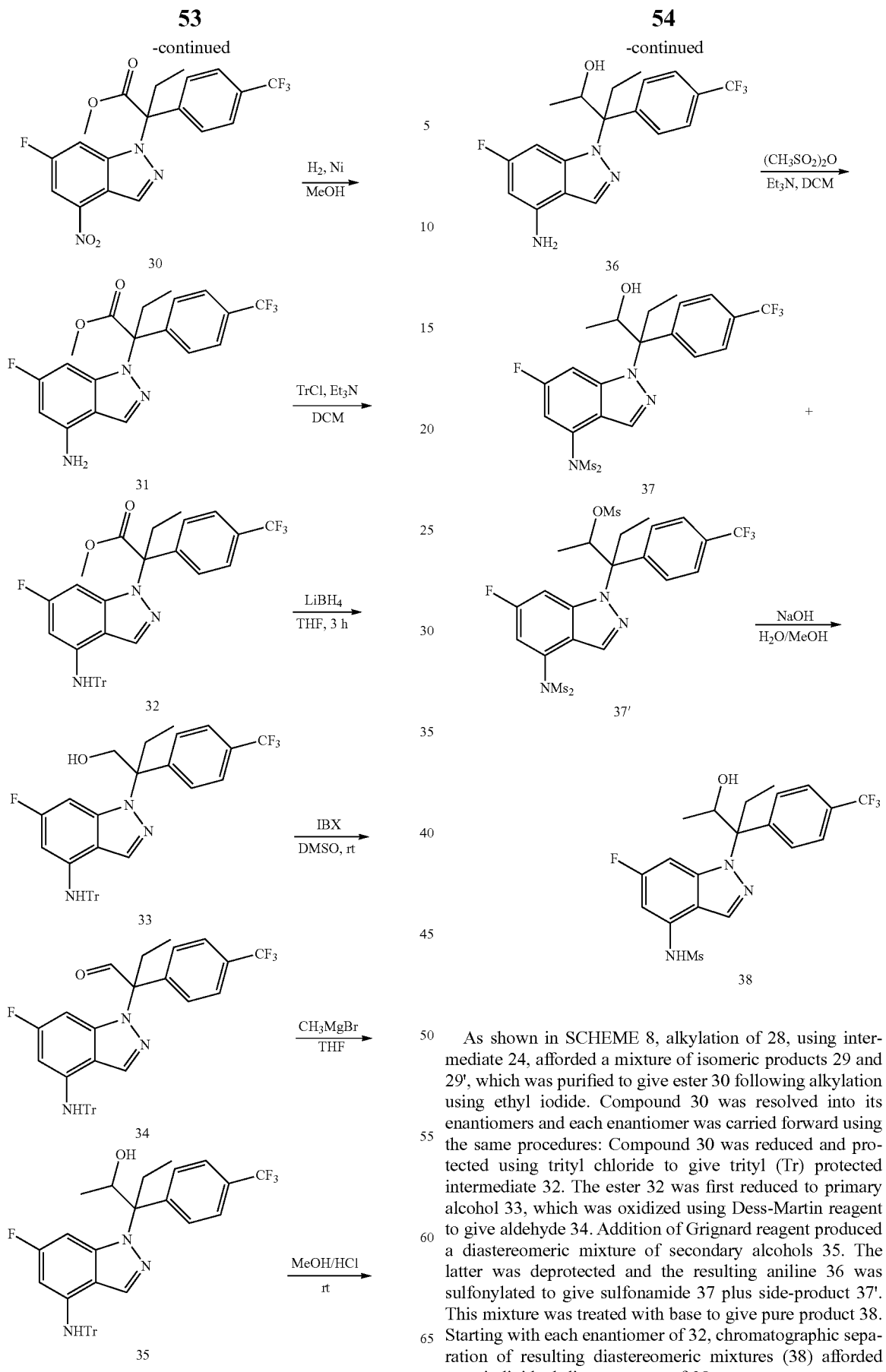

As shown in SCHEME 8, alkylation of 28, using intermediate 24, afforded a mixture of isomeric products 29 and 29', which was purified to give ester 30 following alkylation using ethyl iodide. Compound 30 was resolved into its enantiomers and each enantiomer was carried forward using the same procedures: Compound 30 was reduced and protected using trityl chloride to give trityl (Tr) protected intermediate 32. The ester 32 was first reduced to primary alcohol 33, which was oxidized using Dess-Martin reagent to give aldehyde 34. Addition of Grignard reagent produced a diastereomeric mixture of secondary alcohols 35. The latter was deprotected and the resulting aniline 36 was sulfonylated to give sulfonamide 37 plus side-product 37'. This mixture was treated with base to give pure product 38. Starting with each enantiomer of 32, chromatographic separation of resulting diastereomeric mixtures (38) afforded pure individual diastereomers of 38.

SCHEME 9

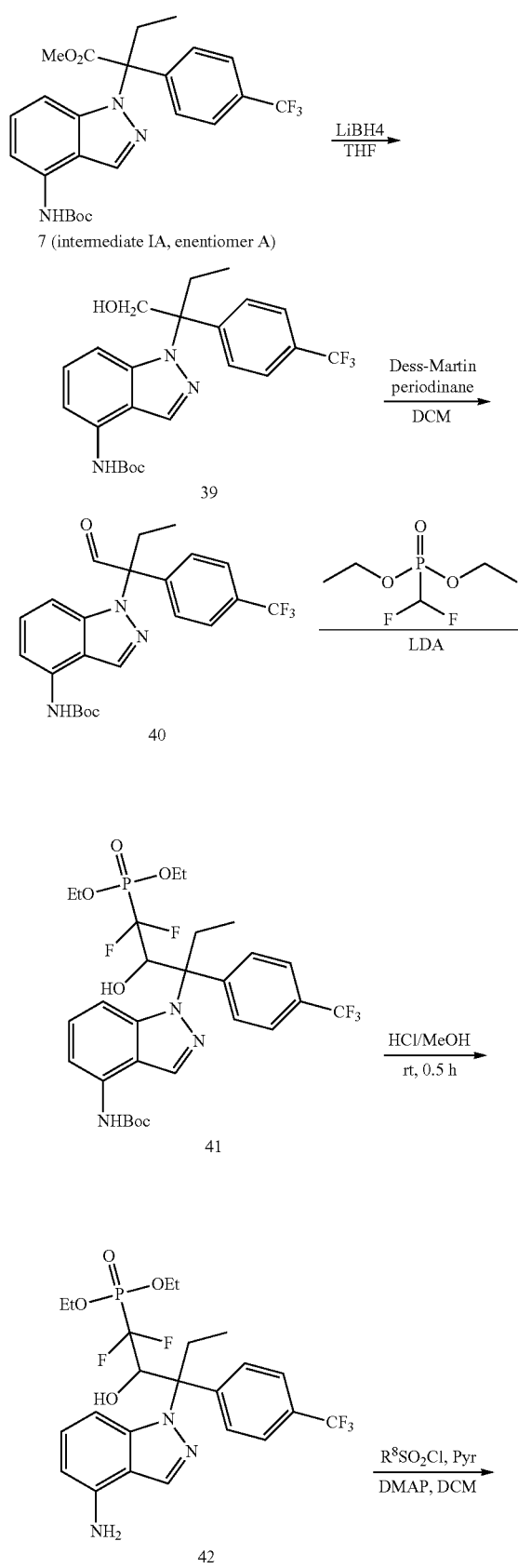

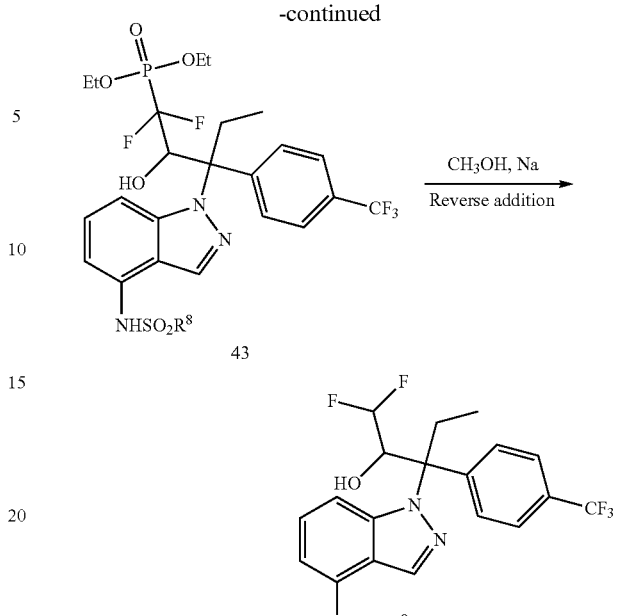

As shown in SCHEME 9, intermediate ester 7 can be reduced to give alcohol 39, which in turn was oxidized to aldehyde 40. An addition was carried out on compound 40 to afford the intermediate 41. A Boc deprotection of 41 and subsequent sulfonylation using appropriate alkylsulfonyl chloride provided intermediate 43. Removal of the phosphonate group from 43 provides compounds 44. The diastereomeric mixture of 44 can be separated into individual diastereomers. A similar sequence of reactions can be carried out on the fluorine substituted indazole starting material to afford fluorine substituted 44 analogs.

The following examples are provided so that the invention might be more fully understood. Unless otherwise indicated, the starting materials are commercially available. They should not be construed as limiting the invention in any way.

REPRESENTATIVE EXAMPLES

The following examples were provided to more fully illustrate the present invention, and shall not be construed as limiting the scope in any manner. Unless stated otherwise:
1) All operations were carried out at room or ambient temperature (rt) unless noted otherwise, that is, at a temperature in the range of about 10-30° C.;
2) Reactions were generally done using commercially available anhydrous solvents under an inert atmosphere, either nitrogen or argon;
3) Microwave reactions were conducted using a Biotage Initiator™ or CEM Explorer® system;
4) Evaporation of solvent was carried out using a rotary evaporator under reduced pressure (4.5-30 mmHg) with a bath temperature of up to about 40° C.;
5) The course of reactions was followed by thin layer chromatography (TLC) and/or tandem high performance liquid chromatography (HPLC) followed by electron spray mass spectroscopy (MS), herein termed LCMS, and any retention times are given for illustration only;
6) The structure of all final compounds was assured by at least one of the following techniques: MS or proton nuclear magnetic resonance (1H NMR) spectrometry, and the purity was assured by at least one of the following techniques: TLC or HPLC;
7) ¹H NMR spectra were recorded on Bruker instrument at 400 or 500 MHz, or on either a Varian Unity or a Varian Inova instrument at 400, 500 or 600 MHz, using the indicated solvent; when line-listed, NMR data is in the form of delta values for major diagnostic protons, given in parts per million (ppm) relative to residual solvent peaks (multiplicity and number of hydrogens) or internal tetramethylsilane (TMS); conventional abbreviations used for signal shape are: s. singlet; d. doublet (apparent); t. triplet (apparent); m. multiplet; br. broad; etc.;
8) MS data were recorded on Agilent 6110A MSD, interfaced with a Hewlett-Packard (Agilent 1200) HPLC instrument, and operating on Agilent rev.B.03.02 software or on a Waters Micromass unit, interfaced with a Hewlett-Packard (Agilent 1100) HPLC instrument, and operating on MassLynx/OpenLynx software; electrospray ionization was used with positive (API-ES+) or negative ion (API-ES-) detection; and diode array detection. LC/MS method: (LC2M_Low/Med_Positive mode. LC Conditions: 5-98% $CH_3CN/H_2O+v$ 0.1% TFA over 1.25 min; Flow Rate=1.5 mL/min, UV wavelength 254 nm; Column: Waters XTerra® MS C18 3.5 μm 2.1×20 mm IS™.
9) Purification of compounds by preparative reverse phase HPLC was performed on a Gilson 281 system using a XBridge Prep C18 10 um OBD (250×19 mm i.d.) eluting at 30 mL/min with a water (10 mM $NH_4HCO_3$)/acetonitrile gradient (5% acetonitrile to 95% acetonitrile) or a Shimadzu PRC-ODS (250×20 mm i.d.) eluting at 30 mL/min with a water (10 mM $NH_4HCO_3$ or 0.05% TFA)/acetonitrile gradient (5% acetonitrile to 95% acetonitrile) or a Sunfire Prep C18 OBD Sum (100×30 mm) eluting at 30 mL/min with a water (10 mM $NH_4HCO_3$ or 0.05% TFA)/acetonitrile gradient (5% acetonitrile to 95% acetonitrile) or on a Gilson system using a YMC-Pack Pro C18 column (150×20 mm i.d.) eluting at 20 mL/min with a water/acetonitrile (0.1% TFA) gradient (5% acetonitrile to 95% acetonitrile) or on a Shimadzu system using a Sunfire Prep C18 OBD 5 μM column (100×30 mm i.d.) eluting at 50 mL/min with a water/acetonitrile (0.1% TFA) gradient;
10) Purification of compounds by preparative thin layer chromatography (PTLC) was conducted on 20×20 cm glass plates coated with silica gel, commercially available from Labpartner, Analtech or E. Merck;
11) Flash column chromatography was carried out on a glass silica gel column using silica gel, 200-300 mesh ($SiO_2$), or using Kieselgel 60, 0.063-0.200 mm ($SiO_2$), or on a Biotage $SiO_2$ cartridge system using the Biotage Horizon and Biotage SP-1 systems; or a Teledyne Isco $SiO_2$ cartridge using the CombiFlashRf system;
12) Chemical symbols have their usual meanings, and the following abbreviations have also been used: h (hours), min (minutes), d (days), v (volume), w (weight), b.p. (boiling point), m.p. (melting point), L (liter(s)), mL (milliliters), g (gram(s)), mg (milligrams(s)), mol (moles), mmol (millimoles), eq or equiv (equivalent(s)), IC50 (molar concentration which results in 50% of maximum possible inhibition), EC50 (molar concentration which results in 50% of maximum possible efficacy), μM (micromolar), nM (nanomolar).

Preparation of Intermediate IA

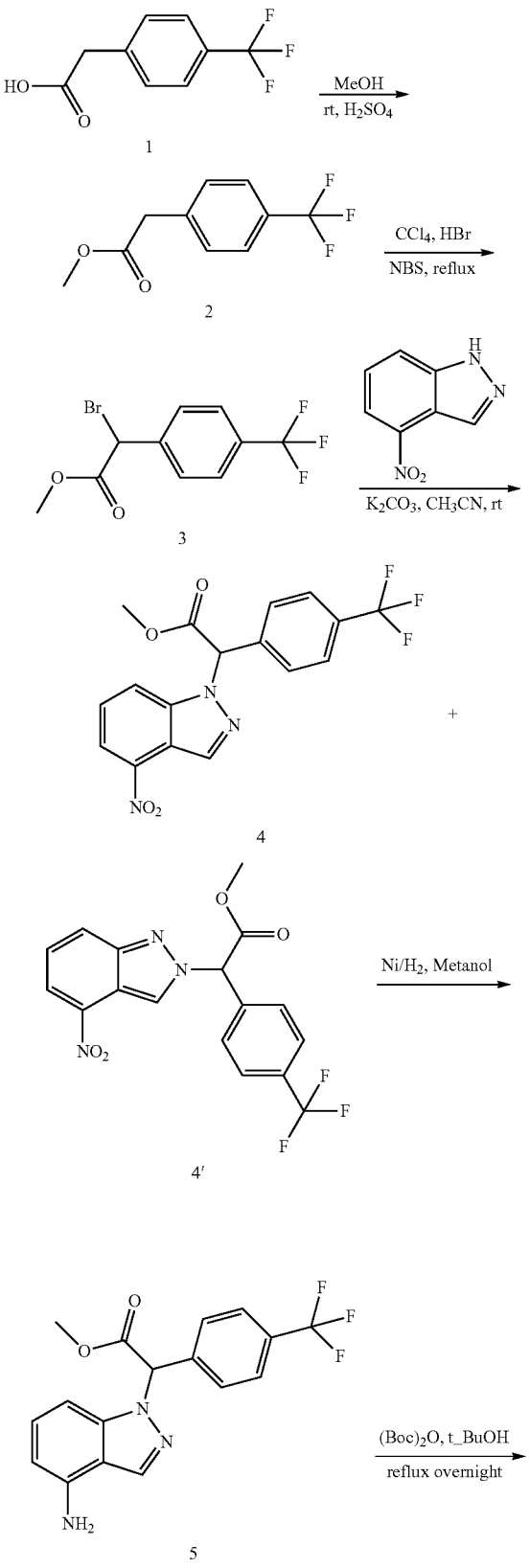

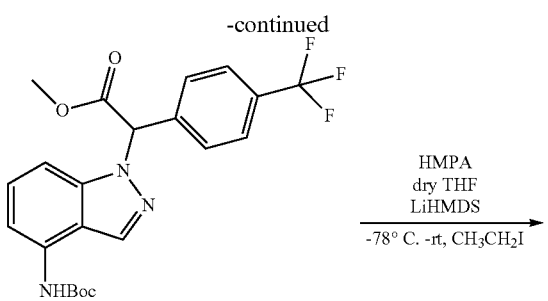

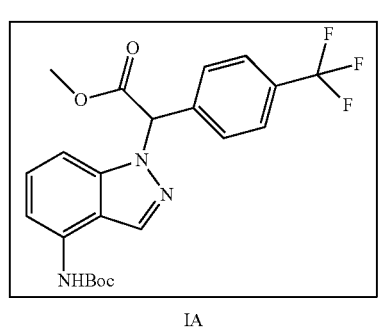

Step A: Synthesis of Compound 2:

To a solution of compound 1 (10.0 g, 49 mmol) in methanol (250 ml) was added concentrated sulfuric acid (2 ml) at rt, and the mixture was stirred for 2 hours. After removing the solvent, the residue was dissolved in ethyl acetate (200 ml), washed with a saturated sodium bicarbonate solution (50 ml×3), dried with anhydrous sodium sulfate, then filtered. After removing the organic solvent, the residue was used for the next step without purification.

Step B: Synthesis of Compound 3:

To a solution of compound 2 (10.7 g, 49 mmol) and NBS (13.1 g, 73.6 mmol) in carbon tetrachloride (200 ml) was add hydrobromic acid (1.0 ml). The mixture was heated to 80° C. and stirred overnight. After cooling, the residue was dissolved in ethyl acetate (200 ml), washed with a saturated sodium chloride solution (50 ml×3), dried with anhydrous sodium sulfate, then filtered. After removing the organic solvent, the residue was used for the next step without purification.

Step C: Synthesis of Compound 4:

To a mixture of 4-nitro-1H-indazole (9.6 g, 58.8 mmol) in acetonitrile (200 ml) was added potassium carbonate (10.8 g, 78.4 mmol) at rt, followed by the addition of compound 3 (14.5 g, 80%, about 39.2 mmol). The reaction mixture was stirred for 4 hours. The precipitate was removed by filtration. After the filtrate was concentrated under vacuum, the residue (mixture of 4 and 4') was used for the next step without purification.

Step D: Synthesis of Compound 5 and 5':

To a solution of mixture 4+4' (19.0 g, 70%, about 35.0 mmol) in methanol (500 ml) was added Raney-nickel (2.0 g) at rt. The mixture was charged with hydrogen three times then stirred for one hour. After removal of the catalyst by filtration, solvent was removed in vacuum to give a yellow oil. The residue mixtures (5 and 5') were used for the next step without purification.

Step E: Synthesis of Compound 6:

A mixture of compound 5+5' (17.0 g, 70%, about 34.0 mmol), di-tert-butyl dicarbonate (8.0 g, 37.2 mmol) and t-butanol (200 ml) was heated to 80° C. and stirred overnight. After removing the solvent, the residue was purified by chromatogram on silica gel (eluent: ethyl acetate/petroleum=1:10) to give a pure white solid 6.

Step F: Synthesis of Intermediate IA:

To a solution of compound 6 (2 g, 4.5 mmol) in dry tetrahydrofuran (10 ml) and HMPA (2 ml) was added LiHMDS (4.5 ml, 4.5 mmol) at −78° C. After stirring for 30 minutes, iodoethane (0.696 g, 4.5 mmol) was added at this temperature, and then the reaction mixture was warmed to rt and stirred for additional one hour. The mixture was quenched with a saturated ammonium chloride solution (50 ml), then ethyl acetate (100 ml) was added, and the organic layer was washed with water (50 ml×2). The organic layer was dried with anhydrous sodium sulfate, the solvent was removed in vacuo, and the residue was purified by silica gel chromatography (eluent: ethyl acetate/petroleum=1:10) to give racemic Intermediate IA as a white solid.

The racemic Intermediate IA was separated on a AD column (250 mm×50 mm, 5 um) with Mobile phase: A: Supercritical $CO_2$, B: MeOH, A: B=80:20 at 140 ml/min, Column Temp: 38° C.

Nozzle Pressure: 100 Bar, Nozzle Temp: 60° C.

Enantiomer A of Intermediate IA had retention time of 3.32 min on a analytical AD column (150×4.6 mm I.D., 3 μm; Column Temp: 35 deg.; Mobile Phase: methanol (0.05% DEA) in CO2 from 5% to 40%; Flow Rate: 2.5 mL/min)

Enantiomer B of Intermediate IA had retention time of 4.67 min. on the same analytical column.

Example 1

N-(1-(3-(4-bromophenyl)-2-hydroxypentan-3-yl)-1H-indazol-4-yl)methanesulfonamide (Diastereomers A, B, C and D)

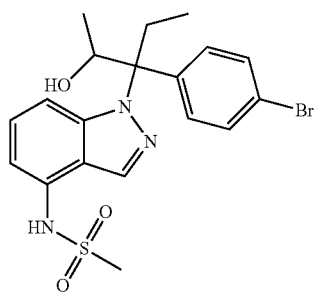 [SMILES: CCC(c1ccc(Br)cc1)(C(C)O)n1ncc2c(NS(C)(=O)=O)cccc21]

Step A: methyl 2-(4-bromophenyl)acetate

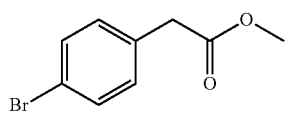

To a solution of 2-(4-bromophenyl)acetic acid (38.0 g, 177 mmol) in methanol (500 mL) was added concentrated sulfuric acid (7.2 mL) at rt, and the mixture was stirred for 2 h. After removing the solvent, the residue was dissolved in ethyl acetate (300 mL), washed with saturated sodium bicarbonate (50 mL×3), dried over anhydrous sodium sulfate, and then filtered. After removing organic solvent, the crude product was used for the next step without purification.

Step B: methyl 2-bromo-2-(4-bromonhenyl)acetate

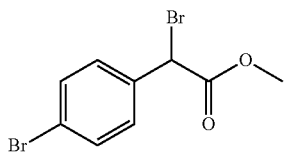

To a solution of methyl 2-(4-bromophenyl)acetate from Step A (40 g, 176 mmol) and NBS (34.5 g, 194 mmol) in CCl$_4$ (500 mL) was added AIBN (2.89 g, 17.6 mmol). Then the mixture was heated to 80° C. overnight. After cooling to rt, the mixture was concentrated in vacuo. The residue was dissolved with ethyl acetate (300 mL), washed with brine (50 mL×3), dried over anhydrous sodium sulfate, then filtered. The organics were concentrated under reduced pressure to afford the title compound, which was used in next step without purification.

Step C: methyl 2-(4-bromophenyl)-2-(4-nitro-1H-indazol-1-yl)acetate and methyl 2-(4-bromophenyl)-2-(4-nitro-1H-indazol-2-yl)acetate

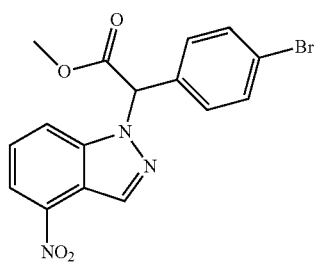

C

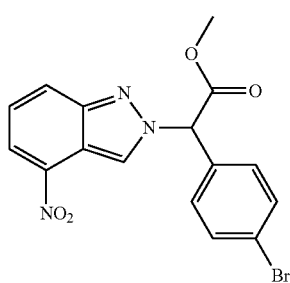

C'

To a mixture of 4-nitro-1H-indazole (5 g, 31 mmol) and potassium carbonate (10.7 g, 77.5 mmol) in dry acetonitrile (80 mL) was added methyl 2-bromo-2-(4-bromophenyl) acetate from Step B above (8.44 g, 37.2 mmol) at 0° C. Then the mixture was stirred at rt overnight. The potassium carbonate was removed by filtration and the acetonitrile was removed under reduced pressure. The residue was diluted with water (20 mL) and extracted with ethyl acetate (30 mL × 3). The combined organics were dried over anhydrous magnesium sulfate, filtered and concentrated under reduced pressure to give the crude product, which was purified by silica gel column chromatography (PE/EA=8/1) to afford the title mixtures. LC/MS (m/z): 392.0 [M+1].

Step D: methyl 2-(4-bromophenyl)-2-(4-nitro-1H-indazol-1-yl)butanoate

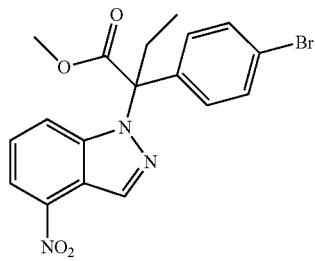 [SMILES: CCC(C(=O)OC)(c1ccc(Br)cc1)n1ncc2c([N+](=O)[O-])cccc21]

To a solution containing the product of Step C above (4 g, 10.3 mmol) in THF (40 mL) and HMPA (10 mL) was added LiHMDS (30.9 mL, 30.9 mmol, 1 M in THF) at −78° C. After stirring at −78° C. for 30 min, EtI (4.8 g, 30.9 mmol) was added to the mixture. Then the resulting mixture was gradually warmed to rt, quenched with saturated aqueous ammonium chloride (30 mL) and extracted with ethyl acetate (30 mL×3). The combined organics were washed with water (15 mL) and brine (15 mL), dried over anhydrous MgSO$_4$, filtered and concentrated in vacuo. The resulting crude product was purified by silica gel column chromatography (PE/EA=30/1) to afford the title compound. LC/MS (m/z): 418.0 [M+1].

Step E: methyl 2-(4-amino-1H-indazol-1-yl)-2-(4-bromophenyl)butanoate

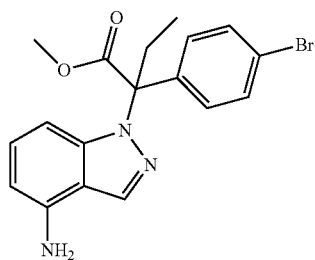 [SMILES: CCC(C(=O)OC)(c1ccc(Br)cc1)n1ncc2c(N)cccc21]

To a solution of methyl 2-(4-bromophenyl)-2-(4-nitro-1H-indazol-1-yl) butanoate from Step D above (2.04 g, 4.9 mmol) in EA (30 mL) was added 10% Pt/C (200 mg) at rt. The mixture was degassed three times and backfilled with hydrogen, and then stirred under a hydrogen atmosphere for 1 h at rt. The solid was removed by filtration and the filtrate was concentrated in vacuo to afford the crude title compound, which was used for the next step without purification. LC/MS (m/z): 386.9 [M+1].

Step F: methyl 2-(4-bromophenyl)-2-(4-(tert-butoxycarbonylamino)-1H-indazol-1-yl)butanoate

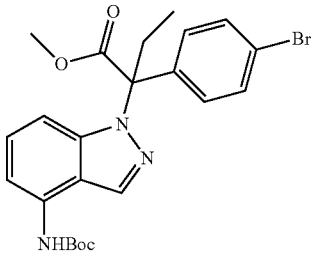 [SMILES: CCC(C(=O)OC)(c1ccc(Br)cc1)n1ncc2c(NC(=O)OC(C)(C)C)cccc21]

A mixture of methyl 2-(4-amino-1H-indazol-1-yl)-2-(4-bromo phenyl) butanoate from Step E above (1.85 g, 4.78 mmol) and Boc$_2$O (2.06 g, 9.56 mmol) in t-BuOH (20 mL) was heated to 80° C. overnight. The solvent was evaporated and the residue was purified by silica gel column chromatography (PE/EA=5/1) to afford the title compound. LC/MS (m/z): 488.0 [M+1].

Step G: tert-butyl 1-(2-(4-bromophenyl)-1-hydroxybutan-2-yl)-1H-indazol-4-ylcarbamate (Enantiomer A and B)

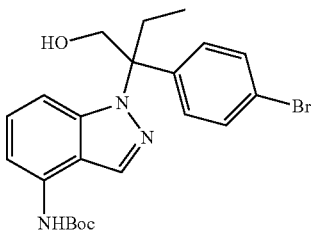 [SMILES: CCC(CO)(c1ccc(Br)cc1)n1ncc2c(NC(=O)OC(C)(C)C)cccc21]

To a solution of methyl 2-(4-bromophenyl)-2-(4-(tert-butoxycarbonylamino)-1H-indazol-1-yl)butanoate from Step F above (1.4 g, 2.87 mmol) in THF (20 mL) was added LiBH$_4$ (631 mg, 28.7 mmol) at 0° C. The reaction mixture was stirred at rt overnight. The mixture was carefully quenched with saturated aqueous ammonium chloride (20 mL) and extracted with ethyl acetate (30 mL×3). The combined organic layers were washed with brine (20 mL) and dried over anhydrous sodium sulfate, filtered and concentrated in vacuo to afford the title compound. LC/MS (m/z): 460.0 [M+1]. The racemic product was resolved by Prep-Chiral-SCF (Column: IC, Mobile phase: SCF (2.4 mL/min)/MeOH (0.1% DEA, 0.6 mL/min), Column Temp: 39.3° C.) to give the enantiomer A (Rt=5.39 min) and enantiomer B (Rt=6.16 min).

Step H: tert-butyl 1-(2-(4-bromophenyl)-1-hydroxybutan-2-yl)-1H-indazol-4-ylcarbamate (Enantiomer B)

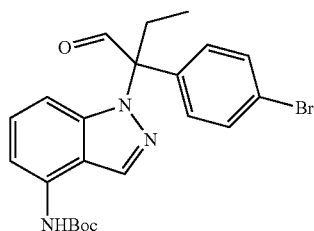 [SMILES: CCC(C=O)(c1ccc(Br)cc1)n1ncc2c(NC(=O)OC(C)(C)C)cccc21]

To a solution of tert-butyl 1-(2-(4-bromophenyl)-1-hydroxybutan-2-yl)-1H-indazol-4-ylcarbamate (360 mg, 0.78 mmol, enantiomer B) in DCM (20 mL) was added Dess-Martin periodinane (992 mg, 2.34 mmol) at 0° C. The mixture was stirred at rt for 0.5 h and the suspension was filtered. The filtrate was washed with water (20 mL) and brine (20 mL). The organic layer was dried over anhydrous magnesium sulfate, filtered and concentrated under reduced pressure to give the crude product, which was purified by silica gel column chromatography (PE/EA=5/1) to afford the title compound. LC/MS (m/z): 458.0 [M+1].

Step I: tert-butyl 1-(3-(4-bromophenyl)-2-hydroxypentan-3-yl)-1H-indazol-4-ylcarbamate (Diastereomer C and D)

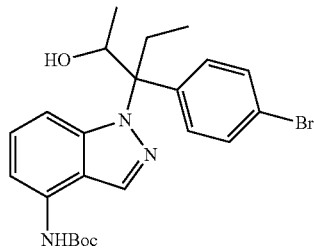 [SMILES: CCC(c1ccc(Br)cc1)(C(C)O)n1ncc2c(NC(=O)OC(C)(C)C)cccc21]

To a solution of tert-butyl 1-(2-(4-bromophenyl)-1-oxobutan-2-yl)-1H-indazol-4-ylcarbamate (Enantiomer B) from Step H above (274 mg, 0.6 mmol) in anhydrous tetrahydrofuran (15 mL) was added methylmagnesium bromide (0.8 mL, 2.4 mmol, 3 M in ether) at 0° C. After stirring for 1 h, the reaction was quenched with saturated aqueous ammonium chloride (10 mL) and extracted with ethyl acetate (10 mL×3). The combined organics were washed with brine (10 mL), dried over anhydrous MgSO$_4$, filtered and concentrated in vacuo. The residue was purified by PREP-TLC (PE/EA=5/1) to afford the title compound. LC/MS (m/z): 476 [M+1].

Step J: 3-(4-amino-1H-indazol-1-yl)-3-(4-bromophenyl)pentan-2-ol (Diastereomer C and D)

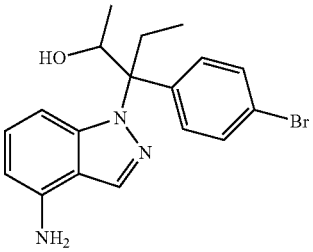 [SMILES: CCC(c1ccc(Br)cc1)(C(C)O)n1ncc2c(N)cccc21]

Trifluoroacetic acid (3 mL) was added rapidly dropwise to a stirred solution of tert-butyl 1-(3-(4-bromophenyl)-2-hydroxypentan-3-yl)-1H-indazol-4-ylcarbamate (Diastereomer C and D) from Step I above (240 mg, 0.51 mmol) in DCM (12 mL) at 0° C. After stirring for 1 h, the reaction was quenched by careful addition of saturated aqueous sodium bicarbonate, followed by extraction with ethyl acetate (10 mL×2). The organic layers were washed with brine (15 mL), dried over anhydrous sodium sulfate, filtered and concentrated in vacuo to afford the title compound. LC/MS (m/z): 373.8 [M+1].

Step K: N-(1-(3-(4-bromophenyl)-2-hydroxypentan-3-yl)-1H-indazol-4-yl) methanesulfonamide (Diastereomer C and D) (Compounds 1 and 2)

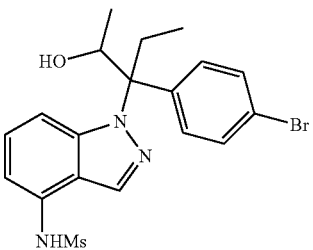

Methanesulfonyl chloride (66 mg, 0.58 mmol) was added to a stirred solution of 3-(4-amino-1H-indazol-1-yl)-3-(4-bromophenyl)pentan-2-ol (Diastereomer C and D) from Step J above (178 mg, 0.48 mmol) and 4-methylmorpholine (96 mg, 0.96 mmol) in DCM (10 mL) at 0° C. After stirring for 30 min, an additional portion of methanesulfonyl chloride (44 mg, 0.38 mmol) was added to the mixture. The reaction mixture was partitioned between DCM and saturated aqueous ammonium chloride. The layers were separated and the aqueous layer was extracted with DCM (10 mL×2). The combined organics were washed with brine (10 mL), dried over sodium sulfate, filtered and concentrated in vacuo. The residue was purified by PREP-TLC (PE/EA=2/1) to afford the title compound. LC/MS (m/z): 452.0 [M+1]. The diastereomeric mixture was resolved by Prep-Chiral-SCF (Column: AS-H, Mobile phase: SCF (2.25 mL/min)/MeOH (0.75 mL/min), Column Temp: 40.5° C.) to give the diastereomer C (Rt=4.34 min) and diastereomer D (Rt=5.4 min).

Diastereomer C (Compound 1): $^1$H NMR (400 MHz, CDCl$_3$) δ 8.27 (s, 1H), 7.50 (s, 1H), 7.42 (d, J=8.4 Hz, 2H), 7.12 (d, J=7.6 Hz, 1H), 7.01-7.07 (m, 3H), 6.34 (d, J=8.0 Hz, 1H), 5.13-5.18 (m, 1H), 4.33 (br, 1H), 3.12 (s, 3H), 2.44-2.51 (m, 2H), 1.05 (d, J=6.8 Hz, 3H), 0.47 (t, J=7.2 Hz, 3H). Diastereomer D (Compound 2): $^1$H NMR (400 MHz, CDCl$_3$) δ 8.26 (s, 1H), 7.46 (d, J=8.4 Hz, 2H), 7.32 (s, 1H), 7.10 (d, J=7.6 Hz, 1H), 7.00-7.05 (m, 3H), 6.25 (d, J=8.4 Hz, 1H), 4.77-4.82 (m, 1H), 3.12 (s, 3H), 2.69-2.76 (m, 1H), 2.47-2.52 (m, 1H), 1.00 (d, J=6.4 Hz, 3H), 0.66 (t, J=7.6 Hz, 3H).

Using the procedure described in Example 1 in Steps H through K, but using enantiomer A from Step G, Compounds 3 and 4 of Table 1 were prepared respectively. For Compound 3, the following final chiral separation conditions apply: SCF, column: OJ-H, Rt=4.04 min. For Compound 4, the following final chiral separation conditions apply: SCF, column: OJ-H, Rt=6.08 min.

Using the procedure described in Example 1 in Steps I through K, but using ethylmagnesium bromide replacement of methylmagnesium bromide, Compounds 5 and 6 of Table 1 were prepared respectively. For Compound 5, the following final chiral separation conditions apply: SCF, column: IC, Rt=2.15 min. For Compound 6, the following final chiral separation conditions apply: SCF, column: IC, Rt=3.78 min.

Using the procedure described in Example 1 in Steps H through K, but using enantiomer A from Step G and ethylmagnesium bromide replacement of methylmagnesium bromide in step I, Compounds 7 and 8 of Table 1 were prepared respectively. For Compound 7, the following final chiral separation conditions apply: SCF, column: AD-H, Rt=3.2 min. For Compound 8, the following final chiral separation conditions apply: SCF, column: AD-H, Rt=5.72 min.

TABLE 1

| Compound Number | IP (nM) | Structure | IUPAC Name | Exact Mass [M + H]$^+$ |
| --- | --- | --- | --- | --- |
| 1 | 10 | 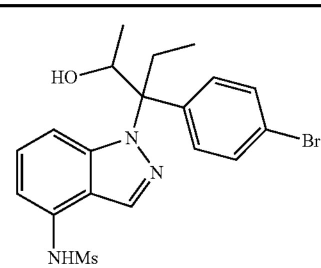 | N-(1-(3-(4-bromophenyl)-2-hydroxypentan-3-yl)-1H-indazol-4-yl)methanesulfonamide (diastereomer C) | 452.0 |

TABLE 1-continued

| Compound Number | IP (nM) | Structure | IUPAC Name | Exact Mass [M + H]+ |
|---|---|---|---|---|
| 2 | 7 | 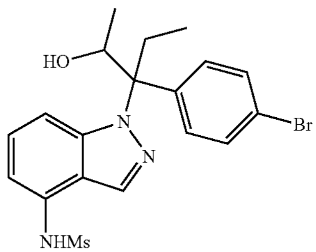 | N-(1-(3-(4-bromophenyl)-2-hydroxypentan-3-yl)-1H-indazol-4-yl) methanesulfonamide (diastereomer D) | 452.0 |
| 3 | 733 | 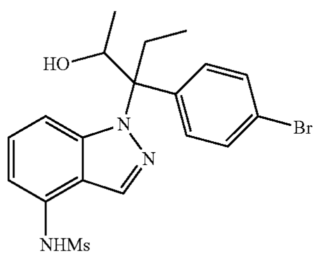 | N-(1-(3-(4-bromophenyl)-2-hydroxypentan-3-yl)-1H-indazol-4-yl) methanesulfonamide (diastereomer A) | 452.0 |
| 4 | 728 | 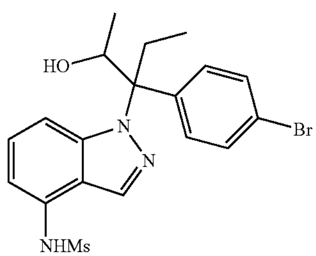 | N-(1-(3-(4-bromophenyl)-2-hydroxypentan-3-yl)-1H-indazol-4-yl) methane sulfonamide (diastereomer B) | 452.0 |
| 5 | 8 | 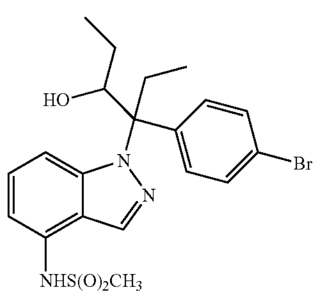 | N-(1-(3-(4-bromophenyl)-4-hydroxyhexan-3-yl)-1H-indazol-4-yl)methane sulfonamide (diastereomer C) | 468.1 |
| 6 | 3 | 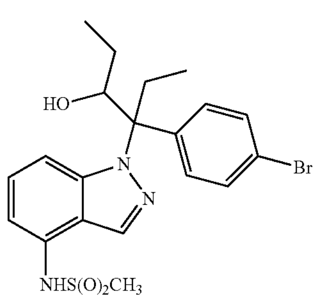 | N-(1-(3-(4-bromophenyl)-4-hydroxyhexan-3-yl)-1H-indazol-4-yl)methane sulfonamide (diastereomer D) | 468.1 |

TABLE 1-continued

| Compound Number | IP (nM) | Structure | IUPAC Name | Exact Mass [M + H]+ |
|---|---|---|---|---|
| 7 | 1992 | 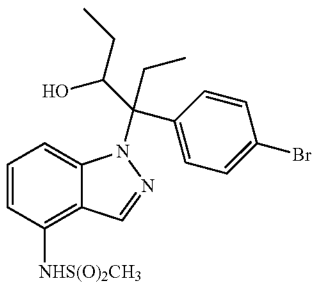 | N-(1-(3-(4-bromophenyl)-4-hydroxyhexan-3-yl)-1H-indazol-4-yl)methanesulfonamide (diastereomer A) | 468.1 |
| 8 | 1189 | 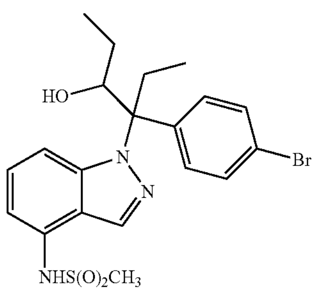 | N-(1-(3-(4-bromophenyl)-4-hydroxyhexan-3-yl)-1H-indazol-4-yl)methanesulfonamide (diastereomer B) | 468.1 |

Compound 2 exhibited good metabolic stability in liver microsome and hepatocytes of multiple animal species. Additionally, Compound 2 exhibited a good PK profile in rats. The PK profile for Compound 2 is shown below:

| Cl (mL/min/kg) | $t_{1/2}$ (hours) | AUCN po (µM · h · kg/mg) | % F |
|---|---|---|---|
| 18 | 3.6 | 1.0 | 49% |

Below is the metabolic stability for Compound 2:

| | Human | Rat | Dog | Rhesus Monkey |
|---|---|---|---|---|
| Liver Microsome Stability ($t_{1/2}$) | 48 mins | 53 mins | 67 mins | 23 mins |
| Hepatocyte Stability ($t_{1/2}$) | 69 mins | >90 mins | 45 mins | 56 mins |

Below is the metabolic stability for verapamil:

| | Human | Rat | Dog | Rhesus Monkey |
|---|---|---|---|---|
| Liver Microsome Stability ($t_{1/2}$) | 20 mins | 16 mins | 18 mins | 5.2 mins |

| | Human | Rat | Dog | Rhesus Monkey |
|---|---|---|---|---|
| Hepatocyte Stability ($t_{1/2}$) | 32 mins | 57 mins | 53 mins | 31 mins |

Example 2

N-(1-(4-hydroxy-3-(4-(trifluoromethyl)phenyl)hexan-3-yl)-1H-indazol-4-yl)methanesulfonamide (Diastereomer A and B) (Compounds 9 and 10)

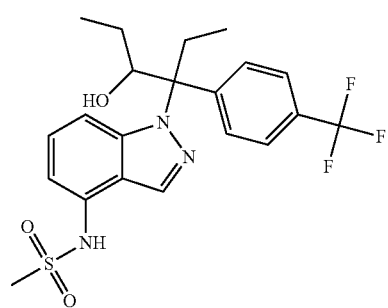 [SMILES: CCC(O)C(CC)(c1ccc(C(F)(F)F)cc1)n1ncc2c(NS(C)(=O)=O)cccc21]

Step A: tert-butyl 1-(4-oxo-3-(4-(trifluoromethyl)phenyl)hexan-3-yl)-1H-indazol-4-ylcarbamate (enantiomer A)

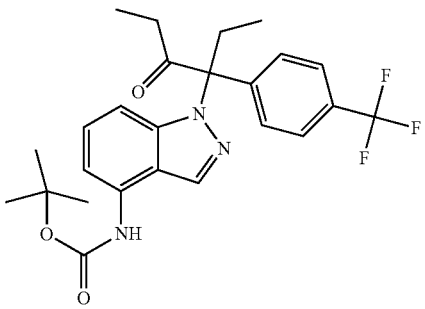 [SMILES: CCC(=O)C(CC)(c1ccc(C(F)(F)F)cc1)n1ncc2c(NC(=O)OC(C)(C)C)cccc21]

To a solution of methyl 2-(4-(tert-butoxycarbonylamino)-1H-indazol-1-yl)-2-(4-(trifluoromethyl)phenyl)butanoate (Intermediate IA, enantiomer A) (1 g, 2.09 mmol) in 2 mL of THF was added ethyllithium (8 mL, 10.48 mol, 1.3 M in ether) at rt. The mixture was stirred at rt for 1.5 h, quenched with sat. ammonium chloride (10 mL) and extracted with ethyl acetate (20 mL×3). The combined organics were washed with brine (10 mL) and dried over anhydrous sodium sulfate, filtered and concentrated in vacuo to provide the crude product, which was used in the next step without further purification. LC/MS (m/z): 476.2 [M+1].

Step B: 4-(4-amino-1H-indazol-1-yl)-4-(4-(trifluoromethyl)phenyl)hexan-3-one (enantiomer A)

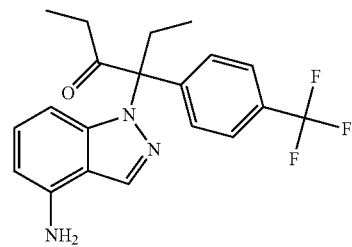 [SMILES: CCC(=O)C(CC)(c1ccc(C(F)(F)F)cc1)n1ncc2c(N)cccc21]

A solution of 4-(4-amino-1H-indazol-1-yl)-4-(4-(trifluoromethyl)phenyl)hexan-3-one (enantiomer A) from Step A above (400 mg, 0.84 mmol) in HCl/MeOH (5 mL) was stirred at 0° C. for 3 h. The volatile was removed in vacuo to provide the title product, which was used in the next step without further purification. LC/MS (m/z): 376.1 [M+1].

Step C: N-(1-(4-oxo-3-(4-(trifluoromethyl)phenyl)hexan-3-yl)-1H-indazol-4-yl)methanesulfonamide (enantiomer A)

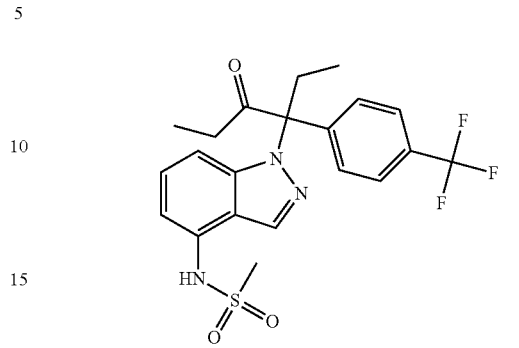

Methanesulfonyl chloride (78 mg, 0.68 mmol) was added to a stirred solution of 4-(4-amino-1H-indazol-1-yl)-4-(4-(trifluoromethyl)phenyl)hexan-3-one (enantiomer A) from Step B above (200 mg, 0.53 mmol) and 4-methylmorpholine (68 mg, 0.68 mmol) in DCM (5 mL) at 0° C. After stirring 30 min, the mixture was warmed to rt and stirred for another 3 h. The reaction mixture was diluted with DCM (10 mL) and saturated aqueous ammonium chloride (10 mL). The layer was separated and the aqueous layer was extracted with DCM (10 mL×3). The combined organics were washed with brine (10 mL), dried over anhydrous sodium sulfate, filtered and concentrated in vacuo. The residue was purified by silica gel flash chromatography (PE:EA=2:1) to afford the title compound. LC/MS (m/z): 454.1 [M+1].

Step D: N-(1-(4-hydroxy-3-(4-(trifluoromethyl)phenyl)hexan-3-yl)-1H-indazol-4-yl)methanesulfonamide (Diastereomer A and B)

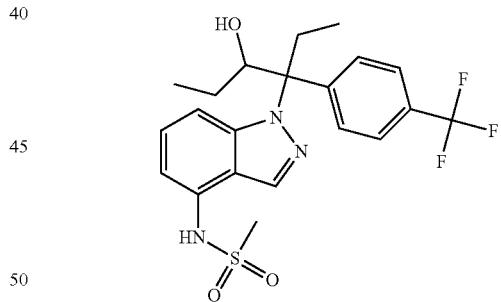

To a solution of N-(1-(4-oxo-3-(4-(trifluoromethyl)phenyl)hexan-3-yl)-1H-indazol-4-yl)methanesulfonamide (enantiomer A) from Step C above (150 mg, 0.33 mmol) in THF (5 mL) was added NaBH$_4$ (60 mg, 1.58 mmol) at 0° C. After stirring at 0° C. for 30 min, the mixture was warmed to rt and stirred for another 2 h. The reaction was quenched with saturated aqueous ammonium chloride (10 mL) and extracted with DCM (10 mL×3). The combined organic layer was washed with brine (10 mL) and dried over anhydrous sodium sulfate, filtered and concentrated. The residue was purified by PREP-HPLC to afford diastereomer A (Rt (LCMS: TFA)=1.77 min) and diastereomer B (Rt (LCMS: TFA)=1.80 min). LC/MS (m/z): 456.1 [M+1].

Diastereomer A (Compound 9): $^1$H NMR (400 MHz, CDCl$_3$) δ 8.22 (s, 1H), 7.58 (d, J=8.4 Hz, 2H), 7.26-7.27 (m, 2H), 7.09 (d, J=7.6 Hz, 1H), 7.02 (t, J=8.0 Hz, 1H), 6.92 (d, J=8.4 Hz, 1H), 4.51-4.54 (m, 1H), 3.11 (s, 3H), 2.54-2.79 (m, 2H), 1.15-1.34 (m, 2H), 0.95 (t, J=6.8 Hz, 3H), 0.69 (t, J=7.2 Hz, 3H).

Diastereomer B (Compounds 10): $^1$H NMR (400 MHz, CDCl$_3$) δ 8.22 (s, 1H), 7.56 (d, J=8.4 Hz, 2H), 72.9 (d, J=8.4 Hz, 2H), 6.93-7.11 (m, 3H), 6.26 (d, J=8.0 Hz, 1H), 4.85-4.88 (m, 1H), 3.12 (s, 3H), 2.49-2.79 (m, 2H), 1.63-1.64 (m, 1H), 1.06 (t, J=7.2 Hz, 3H), 0.82-0.92 (m, 1H), 0.48 (t, J=7.6 Hz, 3H).

Below is the metabolic stability for verapamil:

|  | Human | Rat | Dog | Rhesus Monkey |
|---|---|---|---|---|
| Liver Microsome Stability (t$_{1/2}$) | 21 mins | 15 mins | 19 mins | 7.6 mins |
| Hepatocyte Stability (t$_{1/2}$) | 53 mins | 35 mins | 32 mins | 32 mins |

TABLE 2

| Compound Number | IP (nM) | Structure | IUPAC Name | Exact Mass [M + H]+ |
|---|---|---|---|---|
| 9 | 4 | 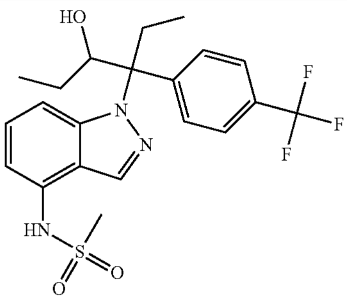 [SMILES: CCC(O)C(CC)(c1ccc(C(F)(F)F)cc1)n1ncc2c(NS(C)(=O)=O)cccc21] | N-(1-(4-hydroxy-3-(4-(trifluoromethyl)phenyl)hexan-3-yl)-1H-indazol-4-yl)methanesulfonamide (diastereomer A) | 456.1 |
| 10 | 5 | 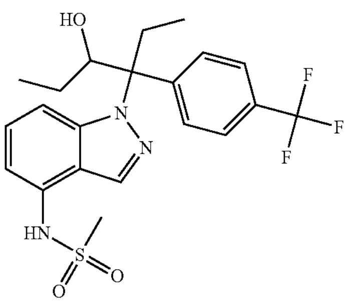 [SMILES: CCC(O)C(CC)(c1ccc(C(F)(F)F)cc1)n1ncc2c(NS(C)(=O)=O)cccc21] | N-(1-(4-hydroxy-3-(4-(trifluoromethyl)phenyl)hexan-3-yl)-1H-indazol-4-yl)methanesulfonamide (diastereomer B) | 456.1 |

Compound 9 exhibited good metabolic stability in liver microsome and hepatocytes of multiple animal species. Additionally, Compound 9 exhibited a good PK profile in rats. The PK profile for Compound 9 is shown below:

| Cl (mL/min/kg) | t$_{1/2}$ (hours) | AUCN po (μM · h · kg/mg) | % F |
|---|---|---|---|
| 24 | 5.3 | 1.3 | 76% |

Below is the metabolic stability for Compound 9:

|  | Human | Rat | Dog | Rhesus Monkey |
|---|---|---|---|---|
| Liver Microsome Stability (t$_{1/2}$) | 72 mins | 61 mins | 65 mins | 61 mins |
| Hepatocyte Stability (t$_{1/2}$) | >90 mins | >90 mins | 48 mins | >90 mins |

Example 3

N-(1-(1-hydroxy-2-(4-(trifluoromethyl)phenyl)butan-2-yl)-1H-indazol-4-yl)methanesulfonamide (enantiomer A) (Compound 11)

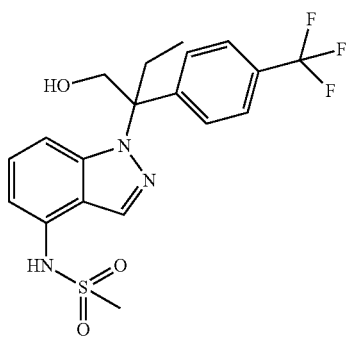 [SMILES: CCC(CO)(c1ccc(C(F)(F)F)cc1)n1ncc2c(NS(C)(=O)=O)cccc21]

Step A: methyl 2-(4-amino-1H-indazol-1-yl)-2-(4-(trifluoromethyl)phenyl)butanoate (enantiomer A)

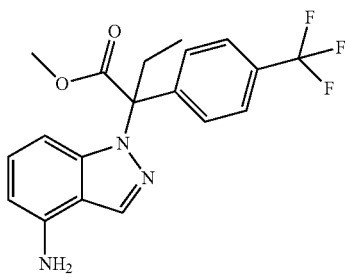 [SMILES: CCC(C(=O)OC)(c1ccc(C(F)(F)F)cc1)n1ncc2c(N)cccc21]

Trifluoroacetic acid (4 mL) was added rapidly dropwise to a stirred solution of methyl 2-(4-(tert-butoxycarbonylamino)-1H-indazol-1-yl)-2-(4-(trifluoromethyl)phenyl)butanoate (Intermediate IA, enantiomer A) (0.95 g, 2 mmol) in DCM (10 mL) at 0° C. After stirring for 1 h, the reaction was quenched with careful addition of saturated aqueous sodium bicarbonate, followed by extraction with ether. The organic layers were washed with saturated aqueous sodium bicarbonate, dried sodium sulfate, filtered and concentrated in vacuo to afford the title compound. LC/MS (m/z): 378.0 [M+1].

Step B: methyl 2-(4-(methylsulfonamido)-1H-indazol-1-yl)-2-(4-(trifluoromethyl)phenyl) butanoate (enantiomer A)

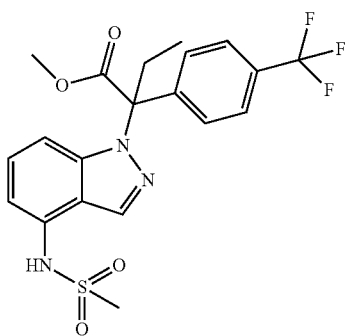 [SMILES: CCC(C(=O)OC)(c1ccc(C(F)(F)F)cc1)n1ncc2c(NS(C)(=O)=O)cccc21]

Methanesulfonyl chloride (0.23 g, 2 mmol) was added to a stirred solution of methyl 2-(4-amino-1H-indazol-1-yl)-2-(4-(trifluoromethyl)phenyl)butanoate (enantiomer A) from Step A above (0.6 g, 1.6 mmol) and 4-methylmorpholine (0.25 g, 2.5 mmol) in DCM (8 mL) at 0° C. After 30 min, an additional portion of methanesulfonyl chloride (0.11 g, 1 mmol) was added to the mixture. The resulting mixture was stirred for another 1 h and diluted with DCM and saturated aqueous ammonium chloride. The layer was separated and the aqueous layer was extracted with DCM. The combined organics were washed with brine, dried over anhydrous sodium sulfate, filtered and concentrated in vacuo. The residue was purified by silica gel flash chromatography (PE:EA=2:1) to afford the title compound. LC/MS (m/z): 456.00 [M+1].

Step C: N-(1-(1-hydroxy-2-(4-(trifluoromethyl)phenyl)butan-2-yl)-1H-indazol-4-yl)methanesulfonamide (enantiomer A)

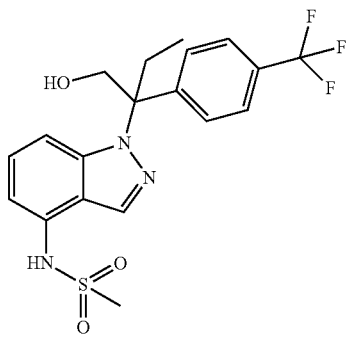 [SMILES: CCC(CO)(c1ccc(C(F)(F)F)cc1)n1ncc2c(NS(C)(=O)=O)cccc21]

To a solution of methyl 2-(4-(methylsulfonamido)-1H-indazol-1-yl)-2-(4-(trifluoromethyl)phenyl)butanoate (enantiomer A) from Step B above (0.5 g, 1.1 mmol) in THF (5 mL) was added dropwise lithium aluminum hydride solution (1.4 mL, 1.4 mmol, 1 M in THF) at −78° C. The reaction mixture was stirred for 0.5 hours at −78° C. TLC and LCMS was monitored to determine when the reaction was complete, then 3M HCl solution was carefully added into the reaction mixture to adjust the pH to 2-3 under ice bath cooling. The organic layer was separated and the aqueous layer was extracted with ethyl acetate. The combined organic layer was washed with brine and dried over anhydrous sodium sulfate. The resulting mixture was filtered and concentrated in vacuo. The residue was purified by silica gel flash chromatography (PE:EA=2:1) to afford the title compound. LC/MS (m/z): 428.00 [M+1]. $^1$H NMR (400 MHz, CDCl$_3$) δ 8.17 (s, 1H), 7.51 (d, J=8.0 Hz, 2H), 7.15 (d, J=8.0 Hz, 2H), 7.01-7.08 (m, 3H), 6.37 (d, J=8.0 Hz, 1H), 4.46 (d, J=12.4 Hz, 1H), 4.03 (d, J=12.4 Hz, 1H), 3.06 (s, 3H), 2.51-2.54 (m, 2H), 0.59 (t, J=7.6 Hz, 3H).

TABLE 3

| Compound Number | IP (nM) | Structure | IUPAC Name | Exact Mass [M + H]+ |
|---|---|---|---|---|
| 11 | 60 | 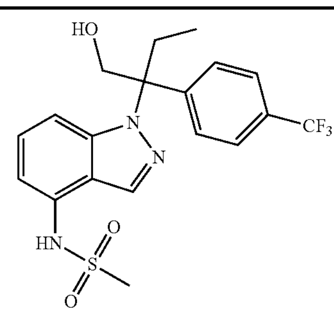 | N-(1-(1-hydroxy-2-(4-(trifluoromethyl)phenyl)butan-2-yl)-1H-indazol-4-yl)methanesulfonamide (enantiomer A) | 428.0 |

Example 4

2-(4-(methylsulfonamido)-1H-indazol-1-yl)-2-(4-(trifluoromethyl)phenyl)butanamide (enantiomer A) (Compound 12)

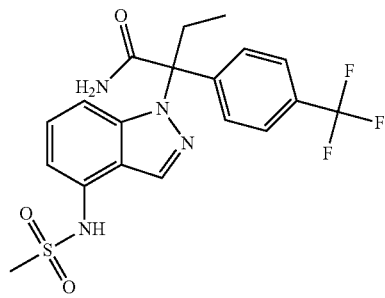 [SMILES: CCC(C(N)=O)(c1ccc(C(F)(F)F)cc1)n1ncc2c(NS(C)(=O)=O)cccc21]

Step A: 2-(4-(methylsulfonamido)-1H-indazol-1-yl)-2-(4-(trifluoromethyl)phenyl)butanoic acid (enantiomer A)

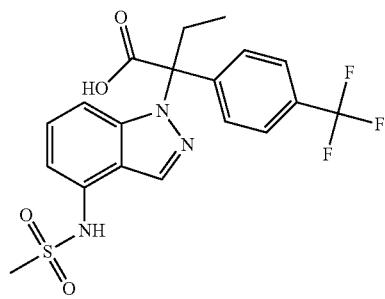 [SMILES: CCC(C(=O)O)(c1ccc(C(F)(F)F)cc1)n1ncc2c(NS(C)(=O)=O)cccc21]

A solution of methyl 2-(4-(methylsulfonamido)-1H-indazol-1-yl)-2-(4-(trifluoromethyl)phenyl)butanoate (enantiomer A) from Step B in Example 3 (250 mg, 0.54 mmol) and aqueous LiOH (0.54 mL, 1.62 mmol 3M in $H_2O$) in THF (2 mL) was stirred at rt for 3 h. The mixture was acidified with 1M HCl (1.7 mL) and extracted with DCM (10 mL×2). The combined organics were washed with brine (10 mL), dried over sodium sulfate, filtered and concentrated in vacuo to provide the title product, which was used in the next step without further purification. LC/MS (m/z): 442.1 [M+1].

Step B: 2-(4-(methylsulfonamido)-1H-indazol-1-yl)-2-(4-(trifluoromethyl)phenyl)butanamide (enantiomer A)

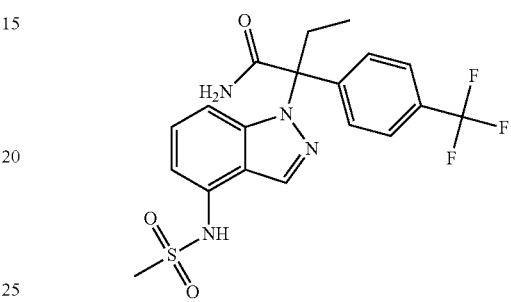

To a solution of 2-(4-(methylsulfonamido)-1H-indazol-1-yl)-2-(4-(trifluoromethyl) phenyl)butanoic acid (enantiomer A) from Step A above (100 mg, 0.23 mmol), HOBT (55 mg, 0.4 mmol) and EDCI (76.5 mg, 0.4 mmol) in 6 mL of DMF was added N-ethyl-N-isopropylpropan-2-amine (52 mg, 0.4 mmol) at rt. After stirring 30 min, ammonium chloride was added to the mixture and stirred for 8 h. The reaction mixture was taken up in $H_2O$ and extracted with DCM (10 mL×2). The combined organic layers were washed with brine (10 mL) and dried over anhydrous sodium sulfate, filtered and concentrated in vacuo. The residue was purified by PREP-HPLC to afford the title compound. LC/MS (m/z): 441.1 [M+1]. $^1$H NMR (400 MHz, CDCl$_3$) δ 8.31 (s, 1H), 7.58 (d, J=8.8 Hz, 2H), 7.52 (d, J=8.0 Hz, 2H), 7.24 (br, 1H), 7.14-7.15 (m, 2H), 6.92 (br, 1H) 6.52-6.55 (m, 1H), 5.67 (br, 1H), 3.13 (s, 3H), 2.97-3.02 (m, 1H), 2.68-2.73 (m, 1H), 0.86 (t, J=7.2 Hz, 3H).

TABLE 4

| Compound Number | IP (nM) | Structure | IUPAC Name | Exact Mass [M + H]+ |
|---|---|---|---|---|
| 12 | 139 | (structure shown) | 2-(4-(methylsulfonamido)-1H-indazol-1-yl)-2-(4-(trifluoromethyl)phenyl)butanamide (enantiomer A) | 441.1 |

Example 5

N-(1-(3-(4-cyanophenyl)-2-hydroxypentan-3-yl)-1H-indazol-4-yl)methanesulfonamide

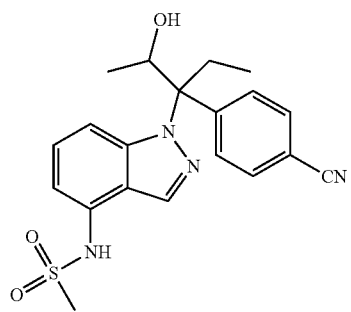 [SMILES: CCC(c1ccc(C#N)cc1)(C(C)O)n1ncc2c(NS(C)(=O)=O)cccc21]

Step A: Methyl 2-(4-(tert-butoxycarbonylamino)-1H-indazol-1-yl)-2-(4-chlorophenyl)butanoate, enantiomer A

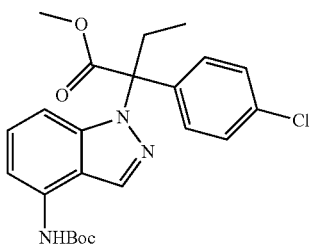 [SMILES: CCC(C(=O)OC)(c1ccc(Cl)cc1)n1ncc2c(NC(=O)OC(C)(C)C)cccc21]

Using the procedures described in Steps A through F of Example 1, but starting with 2-(4-chlorophenyl)acetic acid, the title compound was provided as a racemate. The racemate was resolved on AD-H column using SCF chromatography: A: CO$_2$, B: MeOH, A:B=80:20 at 1.0 mL/min at 38.3° C.; enantiomer A, Rt=3.71 min, enantiomer B, Rt=4.73 min.

Step B: N-{1-[3-(4-chlorophenyl)-2-hydroxypentan-3-yl]-1H-indazol-4-ylmethanesulfonamide, Diastereomer A

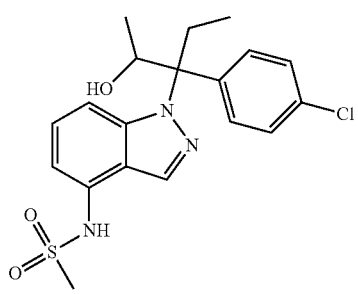 [SMILES: CCC(c1ccc(Cl)cc1)(C(C)O)n1ncc2c(NS(C)(=O)=O)cccc21]

Using the procedure described in Steps G through K of Example 1, but starting with methyl 2-(4-(tert-butoxycarbonylamino)-1H-indazol-1-yl)-2-(4-chlorophenyl)butanoate, enantiomer A from Step A above, the title compound was obtained as a diastereomeric mixture. The individual diastereomers were separated on IC column using SCF chromatography: A: CO2, B: MeOH, A:B=70:30 at 1.0 mL/min at 40° C.; enantiomer A, Rt=6.39 min, enantiomer B, Rt=11.71 min.

Step C: N-(1-(3-(4-cyanophenyl)-2-hydroxypentan-3-yl)-1H-indazol-4-yl)methanesulfonamide, diastereomer A (Compound 13)

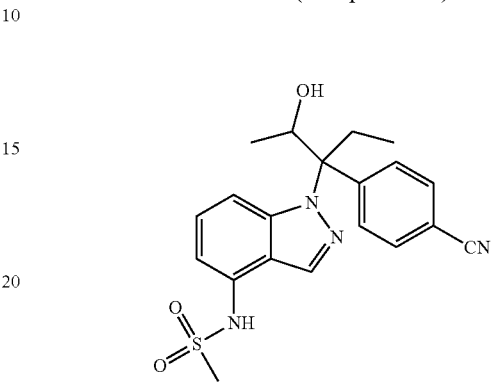

To a solution of N-(1-(3-(4-chlorophenyl)-2-hydroxypentan-3-yl)-1H-indazol-4-yl)methanesulfonamide, diastereomer A from Step B above (304 mg, 0.745 mmol), in anhydrous DMA (4.0 mL) was added zinc cyanide (96 mg, 0.82 mmol), zinc dust (56 mg, 0.820 mmol, 50 micron) and chloro(2-dicyclohexylphosphino-2',4',6'-triisopropyl-1,1'-biphenyl)[2-(2'-amino-1,1'-biphenyl)]palladium(II) (29.3 mg 0.037 mmol) and the suspension was stirred at 130° C. for 2.5 hrs., under an N$_2$ atmosphere. The mixture was cooled to rt and diluted with 4 ml of 50% MeCN/H$_2$O, filtered through a 0.45 micron filter and purified by reverse phase C-18 HPLC chromatography. Lyophilization afforded the title compound as a white lyophilizate. LC/MS m/z=399.4 [M+Na]$^+$. IP (nM)=225.

Using the procedures described above, but in Step C, substituting with N-{1-[3-(4-chlorophenyl)-2-hydroxypentan-3-yl]-1H-indazol-4-ylmethanesulfonamide, Diastereomer B, provides N-(1-(3-(4-cyanophenyl)-2-hydroxypentan-3-yl)-1H-indazol-4-yl)methanesulfonamide, Diastereomer B (Compound 14). IP (nM)=343.

Example 6

N-(1-(3-(4-cyanophenyl)-4-hydroxyhexan-3-yl)-1H-indazol-4-yl)methanesulfonamide, Diastereomer A (Compound 15)

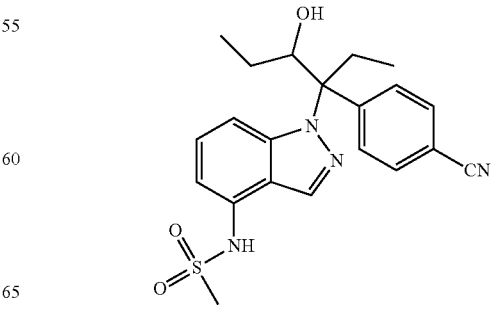

To a solution of N-(1-(-3-(4-bromophenyl)-4-hydroxyhexan-3-yl)-1H-indazol-4-yl)methanesulfonamide, diastereomer C (Compound 5 as described in Example 1 above) (11.4 mg, 0.024 mmol), in anhydrous DMA (0.20 mL) was added zinc cyanide (3.16 mg, 0.027 mmol), zinc dust (1.75 mg, 0.820 mmol, 50 micron) and chloro(2-dicyclohexylphosphino-2',4',6'-triisopropyl-1,1'-biphenyl)[2-(2'-amino-1,1'-biphenyl)]palladium(II) (1.92 mg 0.037 mmol) and the suspension was stirred at 120° C. for 0.5 hrs., under an $N_2$ atmosphere. The mixture was cooled to rt and diluted with 1 ml of 50% MeCN/$H_2O$, filtered through a 0.45 micron filter and purified by reverse phase C-18 HPLC chromatography. Lyophilization afforded the title compound as a white lyophilizate. LC/MS m/z=413.5 [M+1]$^+$. IP (nM)=56.

Using the procedures described above, but substituting with N-(1-(-3-(4-bromophenyl)-4-hydroxyhexan-3-yl)-1H-indazol-4-yl)methanesulfonamide, diastereomer D (Compound 6 as described in Example 1 above) provides N-(1-(3-(4-cyanophenyl)-4-hydroxyhexan-3-yl)-1H-indazol-4-yl)methanesulfonamide, Diastereomer B (Compound 16). IP (nM)=48.

Example 7

Following the analogous procedures described in Examples 1 to 6, but substituting the appropriate starting materials, the following compounds were prepared:

TABLE 5

| Compound No. | IP (nM) | Structure | IUPAC Name | Exact Mass [M + H]+ |
|---|---|---|---|---|
| 17 | 21 | 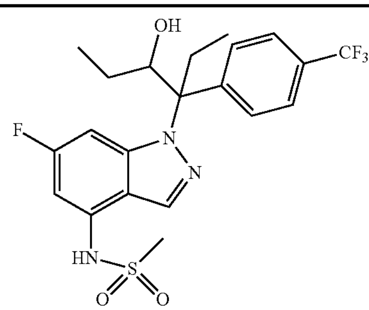 | N-(6-fluoro-1-(4-hydroxy-3-(4-(trifluoromethyl)phenyl)hexan-3-yl)-1H-indazol-4-yl)methanesulfonamide (Diastereomer A) | 474.1 |
| 18 | 9 | 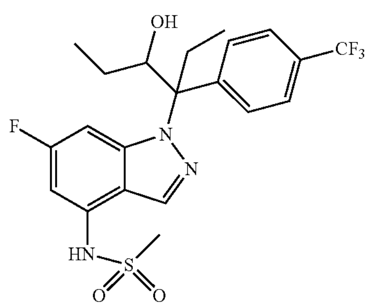 [SMILES: CCC(O)C(CC)(c1ccc(C(F)(F)F)cc1)n1ncc2c(NS(C)(=O)=O)cc(F)cc21] | N-(6-fluoro-1-(4-hydroxy-3-(4-(trifluoromethyl)phenyl)hexan-3-yl)-1H-indazol-4-yl)methanesulfonamide (Diastereomer B) | 474.1 |
| 19 | 136 | 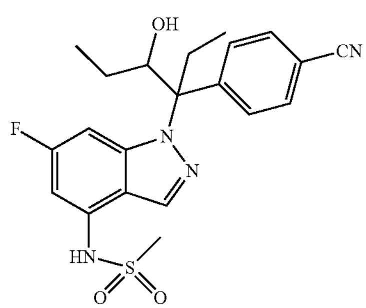 | N-(1-(3-(4-cyanophenyl)-2-hydroxypentan-3-yl)-6-fluoro-1H-indazol-4-yl)methanesulfonamide (Diastereomer A) | 431.0 |
| 20 | 138 | 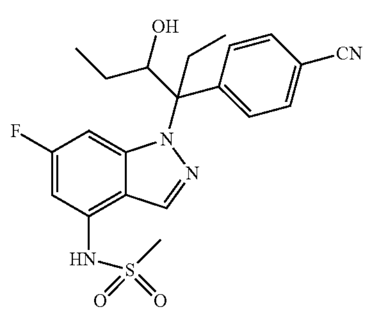 | N-(1-(3-(4-cyanophenyl)-4-hydroxyhexan-3-yl)-6-fluoro-1H-indazol-4-yl)methanesulfonamide (Diastereomer A) | 431.0 |

TABLE 5-continued

| Compound No. | IP (nM) | Structure | IUPAC Name | Exact Mass [M + H]+ |
|---|---|---|---|---|
| 21 | 333 | 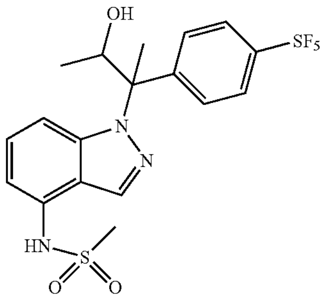 | N-(1-{2-hydroxy-3-[4-(pentafluoro-$\lambda^6$-sulfanyl)phenyl]pentan-3-yl}-1H-indazol-4-yl)methanesulfonamide (Diasteromer A) | 500.1 |
| 22 | 3810 | 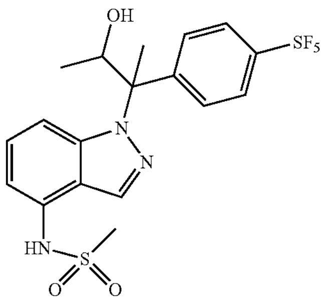 | N-(1-{2-hydroxy-3-[4-(pentafluoro-$\lambda^6$-sulfanyl)phenyl]pentan-3-yl}-1H-indazol-4-yl)methanesulfonamide (Diasteromer B) | 500.1 |
| 23 | 4737 | 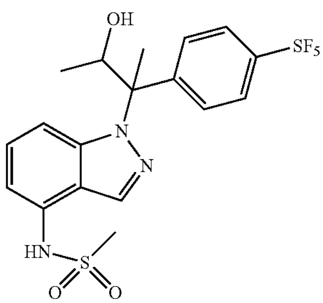 | N-(1-{2-hydroxy-3-[4-(pentafluoro-$\lambda^6$-sulfanyl)phenyl]pentan-3-yl}-1H-indazol-4-yl)methanesulfonamide (Diasteromer C) | 500.1 |
| 24 | 152 | 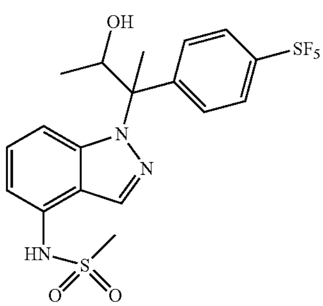 | N-(1-{2-hydroxy-3-[4-(pentafluoro-$\lambda^6$-sulfanyl)phenyl]pentan-3-yl}-1H-indazol-4-yl)methanesulfonamide (Diasteromer D) | 500.2 |
| 25 | 48 | 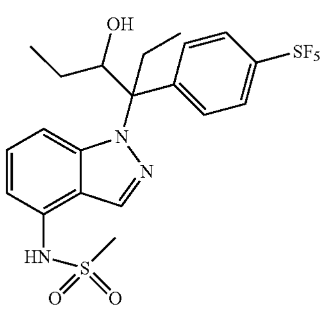 | N-(1-{4-hydroxy-3-[4-(pentafluoro-$\lambda^6$-sulfanyl)phenyl]hexan-3-yl}-1H-indazol-4-yl)methanesulfonamide (Diastereomers A and B) | 514.3 |

TABLE 5-continued

| Compound No. | IP (nM) | Structure | IUPAC Name | Exact Mass [M + H]+ |
|---|---|---|---|---|
| 26 | 1134 | 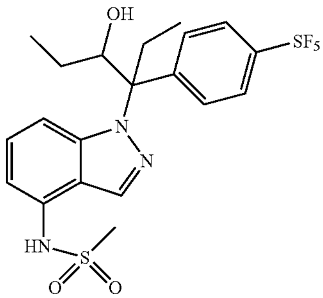 | N-(1-{4-hydroxy-3-[4-(pentafluoro-$\lambda^6$-sulfanyl)phenyl]hexan-3-yl}-1H-indazol-4-yl)methanesulfonamide (Diastereomers A and B) | 514.3 |
| 27 | 3606 | 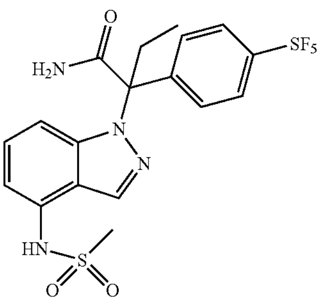 | 2-{4-[(methylsulfonyl)amino]-1H-indazol-1-yl}-2-[4-(pentafluoro-$\lambda^6$-sulfanyl)phenyl]butanamide (racemic) | 499.2 |

Following the analogous procedures described in Examples 1 to 6, but substituting the appropriate starting materials, the following compounds are prepared:

TABLE 6

| 28 | | N-(6-fluoro-1-{2-hydroxy-3-[4-(pentafluoro-$\lambda^6$-sulfanyl)phenyl]pentan-3-yl}-1H-indazol-4-yl)methanesulfonamide |
|---|---|---|
| 29 | | N-(6-fluoro-1-{4-hydroxy-3-[4-(pentafluoro-$\lambda^6$-sulfanyl)phenyl]hexan-3-yl}-1H-indazol-4-yl)methanesulfonamide |

TABLE 6-continued

| 30 | | 2-{6-fluoro-4-[(methylsulfonyl)amino]-1H-indazol-1-yl}-2-[4-(pentafluoro-$\lambda^6$-sulfanyl)phenyl]butanamide |
|---|---|---|

Example 8

N-(6-fluoro-1-(2-hydroxy-3-(4-(trifluoromethyl)phenyl)pentan-3-yl)-1H-indazol-4-yl)methanesulfonamide (Diastereomer A and B) (Compounds 31 and 32)

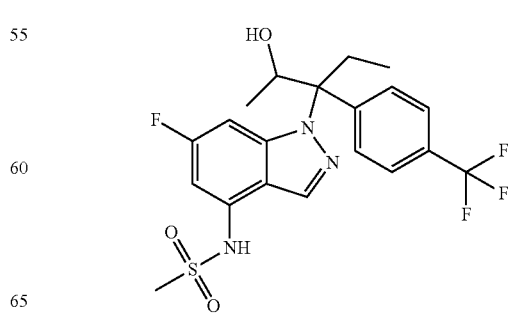

Step A: methyl 2-(4-(trifluoromethyl)phenyl)acetate

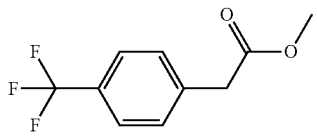

To a solution of 2-(4-(trifluoromethyl)phenyl)acetic acid (10.0 g, 49 mmol) in methanol (250 mL) was added concentrated sulfuric acid (2 mL) at rt. After stirring for 2 h, the solvent was removed under reduced pressure and the residue was dissolved with ethyl acetate (200 mL). The organic layer was washed with saturated sodium bicarbonate solution (30 mL×3), dried over anhydrous sodium sulfate, filtered, and concentrated in vacuo to give the crude title product, which was used for the next step without purification.

Step B: methyl 2-bromo-2-(4-(trifluoromethyl)phenyl)acetate

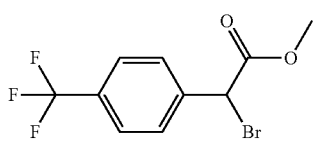 [SMILES: COC(=O)C(Br)c1ccc(C(F)(F)F)cc1]

To a solution of methyl 2-(4-(trifluoromethyl)phenyl) acetate (10.7 g, 49 mmol) and NBS (13.1 g, 73.6 mmol) in benzene (200 mL) was added AIBN (0.8 g, 0.49 mmol) at rt. Then the mixture was heated to 80° C. and stirred overnight. After cooling to rt, the volatiles were removed in vacuo, and the residue was dissolved with ethyl acetate (200 mL). The organic phase was washed with brine (30 mL×3), dried over anhydrous sodium sulfate, filtered and concentrated. The residue was purified by column chromatography (silica gel: 200-300 mesh; eluent: 5% ethyl acetate in hexane) to afford the pure product.

Step C: 5-fluoro-2-methyl-1,3-dinitrobenzene

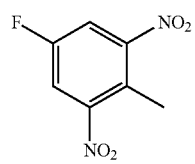

4-Fluoro-1-methyl-2-nitrobenzene (35 g, 226 mmol) was dissolved in fuming sulphuric acid (122 mL) at about −5° C. to about 0° C. A mixture of fuming sulphuric acid (61 mL) and fuming nitric acid (20 mL) was added dropwise to the above solution at about −5° C. to about 0° C. over the period of 45 min. After the addition was completed, the reaction mixture was stirred at rt for 3 h. The reaction mixture was poured into ice (300 g) and extracted with dichloromethane (200 mL×3). The combined organic layers were washed with water (200 mL) and brine (100 mL), dried over anhydrous magnesium sulfate, filtered and concentrated under reduced pressure to give the crude product, which was purified by column chromatography (silica gel: 100-200 mesh; eluent: 2% ethyl acetate in hexane) to afford the purified compound.

Step D: 5-fluoro-2-methyl-3-nitroaniline

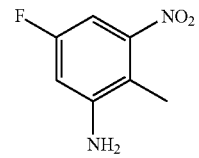

A solution of 5-fluoro-2-methyl-1,3-dinitrobenzene (8.1 g, 40.5 mmol) in ethanol (130 mL) was treated dropwisely with a solution of sodium sulfide nonahydrate (16.39 g, 68 mmol) in water (90 mL). The mixture was allowed to stir at rt for 2.5 h, then diluted with water (500 mL) and extracted with ethyl acetate (500 mL×4). The combined extracts were dried over sodium sulfate, filtered and evaporated under reduced pressure. The residue was purified by flash chromatography on silica gel, eluting with 15% ethyl acetate in hexane to afford 5-fluoro-2-methyl-3-nitroaniline as a solid.

Step E: 6-fluoro-4-nitro-1H-indazole

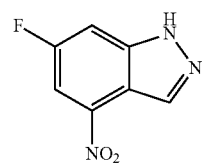

To a solution of 5-fluoro-2-methyl-3-nitroaniline (3 g, 17 mmol) in glacial acetic acid (100 mL) and water (15 mL) was added a solution of sodium nitrite dropwise (3 g, 43.5 mmol) at 0° C. The mixture was allowed to stir at rt for 24 h. After consumption of starting material, acetic acid was removed under reduced pressure. The crude was dissolved in ethyl acetate and filtered through a plug of silica gel to afford the title compound. LC/MS (m/z): 182.3 [M+1].

Step F: methyl 2-(6-fluoro-4-nitro-1H-indazol-1-yl)-2-(4-(trifluoromethyl)phenyl)acetate and methyl 2-(6-fluoro-4-nitro-2H-indazol-2-yl)-2-(4-(trifluoromethyl)phenyl)acetate

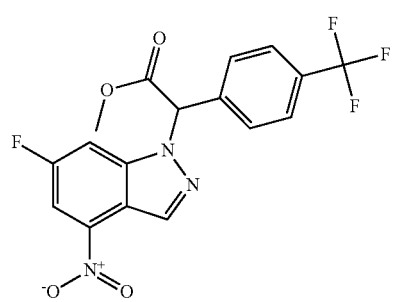

-continued

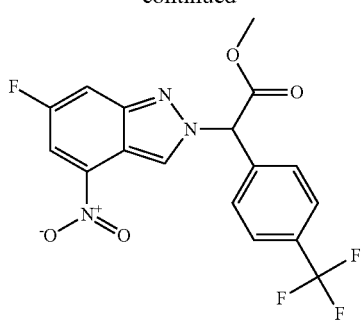

To a solution of 6-fluoro-4-nitro-1H-indazole (2 g, 11 mmol) and potassium carbonate (3 g, 22 mmol) in dry acetonitrile (20 mL) was added methyl 2-bromo-2-(4-(trifluoromethyl)phenyl) acetate (3.9 g, 13.2 mmol) at 0° C. Then the mixture was stirred at rt for 3 h. The potassium carbonate was filtered off and the acetonitrile was removed under reduced pressure. The residue was diluted with water (20 mL) and extracted with ethyl acetate (30 mL×3). The combined organics were dried over anhydrous magnesium sulfate, filtered and concentrated under reduced pressure to obtain the crude product, which was purified by column chromatography (silica gel: 300-400 mesh; eluent: 10% ethyl acetate in hexanes) to afford the mixture of the title products. LC/MS (m/z): 398.2 [M+l].

Step G: methyl 2-(6-fluoro-4-nitro-1H-indazol-1-yl)-2-(4-(trifluoromethyl)phenyl)butanoate

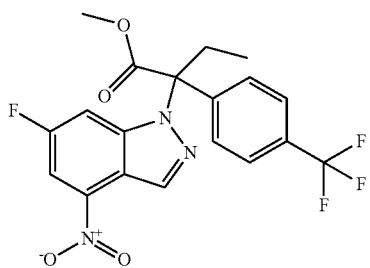

To a solution containing a mixture of the products from the previous step (0.5 g, 1.3 mmol) in THF (10 mL) and HMPA (2.5 mL) was added LiHMDS (3.9 mL, 3.9 mmol, 1M in THF) at −78° C. After stirring for 30 min, EtI (2 g, 12.8 mmol) was added to the mixture. Then the resulting mixture was stirred at 0° C. for another 2 h, quenched by addition of saturated aqueous ammonium chloride (20 mL) and extracted with ethyl acetate (30 mL×3). The combined organics were washed with water and brine, dried over anhydrous $Na_2SO_4$, filtered and concentrated in vacuo. The crude product was purified by column chromatography (silica gel: 300-400 mesh; eluent: 10% ethyl acetate in hexane) to afford the pure title compound. LC/MS (m/z): 426.1 [M+1]. The racemic product was resolved by Prep-Chiral-SCF (Column: AD-H, Mobile phase: SCF (2.7 mL/min)/IPA:Hexane (1:5, 0.1% DEA, 0.3 mL/min), Column Temp: 39.6° C.) to give the enantiomer A (Rt=3.09 min) and enantiomer B (Rt=3.65 min).

Step H: methyl 2-(4-amino-6-fluoro-1H-indazol-1-yl)-2-(4-(trifluoromethyl)phenyl)butanoate (enantiomer A)

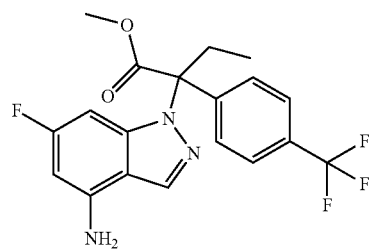 [SMILES: CCC(C(=O)OC)(c1ccc(C(F)(F)F)cc1)n1ncc2c(N)cc(F)cc21]

To a solution of methyl 2-(6-fluoro-4-nitro-1H-indazol-1-yl)-2-(4-(trifluoromethyl)phenyl)butanoate (1 g, 2.4 mmol, enantiomer A) in MeOH (20 mL) was added Raney-Ni (0.1 g) at rt. The mixture was degassed and backfilled with hydrogen (three iterations), then the mixture was stirred at rt for 1 h. The catalyst was filtered off and filtrate was concentrated in vacuo to afford the crude product, which was used for the next step without purification. LC/MS (m/z): 396.1 [M+1].

Step I: methyl 2-(6-fluoro-4-(tritylamino)-1H-indazol-1-yl)-2-(4-(trifluoromethyl)phenyl) butanoate (enantiomer A)

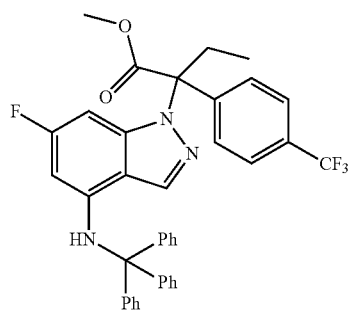 [SMILES: CCC(C(=O)OC)(c1ccc(C(F)(F)F)cc1)n1ncc2c(NC(c3ccccc3)(c3ccccc3)c3ccccc3)cc(F)cc21]

To a solution of methyl 2-(4-amino-6-fluoro-1H-indazol-1-yl)-2-(4-(trifluoromethyl) phenyl)butanoate (enantiomer A) from Step H above (2.5 g, 6.3 mmol) in dry DCM (30 mL) was added $Et_3N$ (1.3 g, 13 mmol) and TrCl (1.9 g, 6.8 mmol). The mixture was stirred at rt for 2 h, then quenched with saturated aqueous ammonium chloride (30 mL) and extracted with ethyl acetate (30 mL×3). The combined organics were washed with water and brine, dried over anhydrous $Na_2SO_4$, filtered and concentrated in vacuo. The crude product was purified by column chromatography (silica gel: 300-400 mesh; eluent: 10% ethyl acetate in hexane) to afford the title compound. LC/MS (m/z): 638.0 [M+1].

Step J: 2-(6-fluoro-4-(tritylamino)-1H-indazol-1-yl)-2-(4-(trifluoromethyl)phenyl)butan-1-ol (enantiomer A)

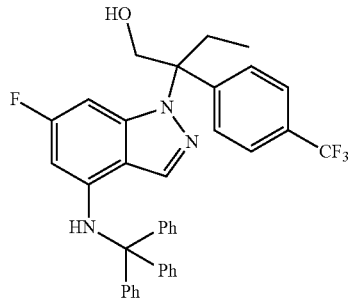 [SMILES: CCC(CO)(c1ccc(C(F)(F)F)cc1)n1ncc2c(NC(c3ccccc3)(c3ccccc3)c3ccccc3)cc(F)cc21]

To a solution of methyl 2-(6-fluoro-4-(tritylamino)-1H-indazol-1-yl)-2-(4-(trifluoromethyl)phenyl)butanoate (enantiomer A) from Step I above (1.6 g, 2.5 mmol) in anhydrous tetrahydrofuran (50 mL) was added LiBH$_4$ (0.17 g, 7.7 mmol) at 0° C. The mixture was stirred at rt for 3 h, carefully quenched with saturated aqueous ammonium chloride (15 mL) and extracted with ethyl acetate (30 mL×3). The combined organics were washed with water and brine (15 mL), dried over anhydrous Na$_2$SO$_4$, filtered and concentrated in vacuo. The crude product was purified by column chromatography (silica gel: 300-400 mesh; eluent: 5% ethyl acetate in hexane) to afford the title compound. LC/MS (m/z): 610.2 [M+1].

Step K: 2-(6-fluoro-4-(tritylamino)-1H-indazol-1-yl)-2-(4-(trifluoromethyl)phenyl)butanal (enantiomer A)

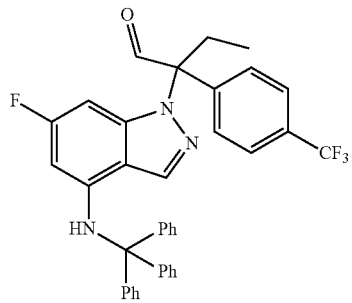 [SMILES: CCC(C=O)(c1ccc(C(F)(F)F)cc1)n1ncc2c(NC(c3ccccc3)(c3ccccc3)c3ccccc3)cc(F)cc21]

To a solution of 2-(6-fluoro-4-(tritylamino)-1H-indazol-1-yl)-2-(4-(trifluoromethyl)phenyl)butan-1-ol (enantiomer A) from Step J above (2.3 g, 3.8 mmol) in dry dimethyl sulfoxide (50 mL) was added 1,2-benziodoxol-3(1H)-one-1-hydroxy-1-oxide (2.64 g, 9.1 mmol) at rt. The mixture was stirred overnight at rt, partitioned between ethyl acetate (50 mL) and water (20 mL). The organic layer was separated and the aqueous layer was extracted with ethyl acetate (20 mL×2). The combined organics were washed with brine (10 mL×3), dried over anhydrous Na$_2$SO$_4$, filtered and concentrated in vacuo to give the crude product, which was used for the next step without purification. LC/MS (m/z): 608.3 [M+1].

Step L: 3-(6-fluoro-4-(tritylamino)-1H-indazol-1-yl)-3-(4-(trifluoromethyl)phenyl)pentan-2-ol (Diastereomers A and B)

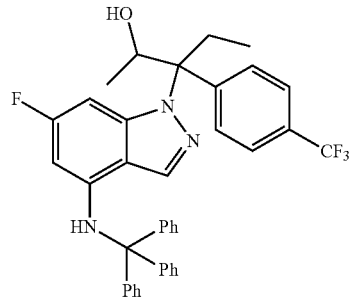 [SMILES: CCC(c1ccc(C(F)(F)F)cc1)(C(C)O)n1ncc2c(NC(c3ccccc3)(c3ccccc3)c3ccccc3)cc(F)cc21]

To a solution of 2-(6-fluoro-4-(tritylamino)-1H-indazol-1-yl)-2-(4-(trifluoromethyl)phenyl)butanal (1.0 g, 1.6 mmol) (enantiomer A) from Step K above in anhydrous tetrahydrofuran (10 mL) was added methylmagnesium bromide (1.1 mL, 3.3 mmol, 3 M in ether) at 0° C. The mixture was stirred at 0° C. for another 1 h, quenched by addition of saturated aqueous ammonium chloride (10 mL) and extracted with ethyl acetate (20 mL×3). The combined organics were washed with water and brine (10 mL), dried over anhydrous Na$_2$SO$_4$, filtered and concentrated in vacuo to give the crude product, which was used for the next step without purification. LC/MS (m/z): 624.0 [M+1].

Step M: 3-(4-amino-6-fluoro-1H-indazol-1-yl)-3-(4-(trifluoromethyl)phenyl)pentan-2-ol (Diastereomers A and B)

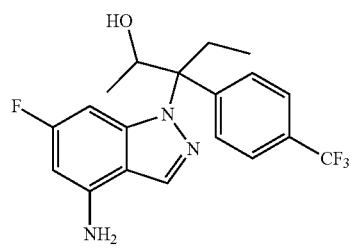 [SMILES: CCC(c1ccc(C(F)(F)F)cc1)(C(C)O)n1ncc2c(N)cc(F)cc21]

A mixture of 3-(6-fluoro-4-(tritylamino)-1H-indazol-1-yl)-3-(4-(trifluoromethyl)phenyl)pentan-2-ol (Diastereomers A and B) from Step L above (1.9 g, 3 mmol) and 4N HCl/MeOH (30 mL) was stirred at rt for 1 h. Then the reaction mixture was neutralized with saturated NaHCO$_3$ solution and the volatiles were removed under reduced pressure. The residue was diluted with water (15 mL) and ethyl acetate (30 mL). The organic layer was separated and the aqueous layer was extracted with ethyl acetate (20 mL×2). The combined organics were washed with brine (10 mL×2), dried over anhydrous Na$_2$SO$_4$, filtered and concentrated. The crude product was purified by column chromatography (silica gel: 300-400 mesh; eluent: 20% ethyl acetate in hexane) to afford the title compound. LC/MS (m/z): 381.9 [M+1].

Step N: N-(6-fluoro-1-(2-hydroxy-3-(4-(trifluoromethyl)phenyl)pentan-3-yl)-1H-indazol-4-yl)-N-(methylsulfonyl)methanesulfonamide (Diastereomers A and B)

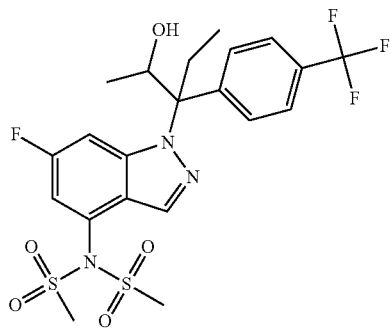 [SMILES: CCC(c1ccc(C(F)(F)F)cc1)(C(C)O)n1ncc2c(N(S(C)(=O)=O)S(C)(=O)=O)cc(F)cc21]

To a solution of 3-(4-amino-6-fluoro-1H-indazol-1-yl)-3-(4-(trifluoromethyl)phenyl)pentan-2-ol (Diastereomers A and B) from Step M above (0.9 g, 2.4 mmol) and Et₃N (0.73 g, 7.2 mmol) in dry dichloromethane (20 mL) was added Ms₂O (1.2 g, 7 mmol) at 0° C. The mixture was stirred at 0° C. for 1 hour, then partitioned between dichloromethane (20 mL) and saturated aqueous ammonium chloride (10 mL). The organic layer was separated and the aqueous layer was extracted with dichloromethane (15 mL×2). The combined organics were washed with brine (10 mL), dried over Na₂SO₄, filtered and concentrated to give the crude product, which was used for the next step without purification. LC/MS (m/z): 538.0 [M+1].

Step O: N-(6-fluoro-1-(2-hydroxy-3-(4-(trifluoromethyl)phenyl)pentan-3-yl)-1H-indazol-4-yl)methanesulfonamide (Diastereomers A and B)

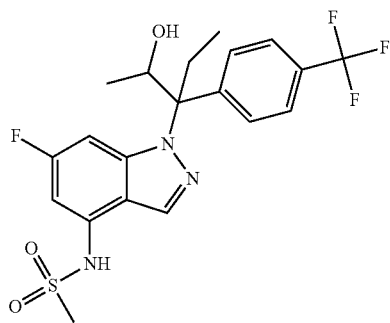 [SMILES: CCC(c1ccc(C(F)(F)F)cc1)(C(C)O)n1ncc2c(NS(C)(=O)=O)cc(F)cc21]

A mixture of N-(6-fluoro-1-(2-hydroxy-3-(4-(trifluoromethyl)phenyl)pentan-3-yl)-1H-indazol-4-yl)-N-(methylsulfonyl)methanesulfonamide (Diastereomers A and B) from Step N above (0.85 g, 1.58 mmol) and NaOH (127 mg, 3.2 mmol) in MeOH (10 mL) and water (1 mL) was refluxed for 24 h. Then the volatile was removed under reduced pressure and the residue was dissolved in saturated aqueous ammonium chloride (20 mL) and DCM (20 mL). The organic layer was separated and the aqueous layer was extracted with dichloromethane (10 mL×2). The combined organics were washed with brine (10 mL), dried over anhydrous Na₂SO₄, filtered and concentrated under reduced pressure. The resulting crude product was purified by column chromatography (silica gel: 300-400 mesh; eluent: 20% ethyl acetate in hexane) to afford the title compound. LC/MS (m/z): 459.8 [M+1]. $^1$H NMR (400 MHz, CDCl₃) δ 8.15 (s, 1H), 7.59 (d, J=8.0 Hz, 2H), 7.28 (s, 1H), 7.09 (s, 1H), 6.98 (d, J=13.6 Hz, 1H), 5.91 (d, J=8.8 Hz, 1H), 5.17 (s, 1H), 4.24 (s, 1H), 3.17 (d, J=2.0 Hz, 3H), 2.52-2.46 (m, 2H), 1.04 (d, J=6.4 Hz, 3H), 0.53-0.49 (m, 2H). The diastereomeric mixture was resolved by Prep-Chiral-SCF (Column: IB, Mobile phase: SCF (2.1 mL/min)/MeOH (0.1% DEA, 0.9 mL/min), Column Temp: 38.1° C.) to give the diastereomer A (Rt=2.33 min) and diastereomer B (Rt=3.7 min).

Diastereomer A (Compound 31): $^1$H NMR (400 MHz, CDCl₃) δ 8.19 (s, 1H), 7.61 (d, J=8.0 Hz, 2H), 7.25-7.26 (m, 2H), 6.96-6.99 (m, 1H), 5.85 (d, J=9.2 Hz, 1H), 5.08 (br, 1H), 4.82-4.85 (m, 1H), 3.17 (s, 3H), 2.75-2.81 (m, 1H), 2.48-2.54 (m, 1H), 1.0 (d, J=6.0 Hz, 3H), 0.7 (t, J=7.6 Hz, 3H).

Diastereomer B (Compound 32): $^1$H NMR (400 MHz, DMSO) δ 8.79 (br, 1H), 8.24 (s, 1H), 7.69 (d, J=8.4 Hz, 2H), 7.42 (d, J=8.4 Hz, 2H), 6.62 (m, 1H), 5.46 (d, J=9.6 Hz, 1H), 5.01-5.05 (m, 1H), 4.84-4.85 (m, 1H), 2.9 (s, 3H), 2.55-2.58 (m, 1H), 2.35-2.41 (m, 1H), 0.85 (d, J=6.8 Hz, 3H), 0.49 (t, J=7.6 Hz, 3H).

Compound 31 exhibited excellent metabolic stability in liver microsome and hepatocytes of multiple animal species. Additionally, Compound 31 exhibited a good PK profile in rats. The PK profile for Compound 31 in rats is shown below:

| Cl (mL/min/kg) | $t_{1/2}$ (hours) | AUCN po (µM · h · kg/mg) | % F |
|---|---|---|---|
| 8.4 | 5.2 | 4.0 | 92 |

Below is the metabolic stability for Compound 31:

| | Human | Rat | Dog | Rhesus Monkey |
|---|---|---|---|---|
| Liver Microsome Stability ($t_{1/2}$) | 156 mins | 234 mins | 128 mins | 67 mins |
| Hepatocyte Stability ($t_{1/2}$) | 90 mins | >90 mins | 73 mins | >90 mins |

Below is the metabolic stability for verapamil:

| | Human | Rat | Dog | Rhesus Monkey |
|---|---|---|---|---|
| Liver Microsome Stability ($t_{1/2}$) | 18 mins | 18 mins | 15 mins | 5.6 mins |
| Hepatocyte Stability ($t_{1/2}$) | 50 mins | 35 mins | 37 mins | 33 mins |

Example 9

N-(6-fluoro-1-(2-hydroxy-3-(4-(trifluoromethyl)phenyl)pentan-3-yl)-1H-indazol-4-yl)methanesulfonamide (Diastereomers C and D) (Compounds 33 and 34)

Using the procedures described in Example 1, Steps H through O, but starting with enantiomer B from Step G, Diastereomers C and D (Compound 33 and 34 of Table 7) were prepared respectively. For Compounds 33 and 34, the following chiral separation conditions were used: Column: AD-H, Mobile phase: SCF (2.1 mL/min)/MeOH (0.1% DEA, 0.9 mL/min), Column Temp: 39.9° C.). Compound 33: Rt=1.62 min; Compound 34: Rt=2.7 min.

TABLE 7

| Compound Number | IP (nM) | Structure | IUPAC Name | Exact Mass [M + H]+ |
|---|---|---|---|---|
| 31 | 51 | 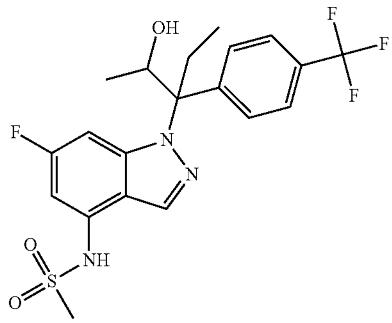 [SMILES: CCC(c1ccc(C(F)(F)F)cc1)(C(C)O)n1ncc2c(NS(C)(=O)=O)cc(F)cc21] | N-(6-fluoro-1-(2-hydroxy-3-(4-(trifluoromethyl)phenyl)pentan-3-yl)-1H-indazol-4-yl)methanesulfonamide (diastereomer A) | 459.8 |
| 32 | 27 | 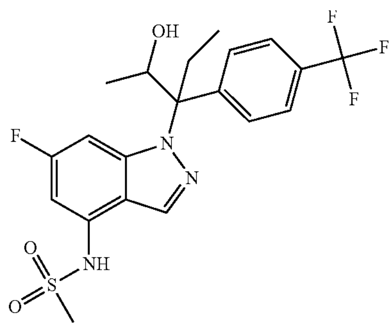 [SMILES: CCC(c1ccc(C(F)(F)F)cc1)(C(C)O)n1ncc2c(NS(C)(=O)=O)cc(F)cc21] | N-(6-fluoro-1-(2-hydroxy-3-(4-(trifluoromethyl)phenyl)pentan-3-yl)-1H-indazol-4-yl)methanesulfonamide (diastereomer B) | 459.8 |
| 33 | 1108 | 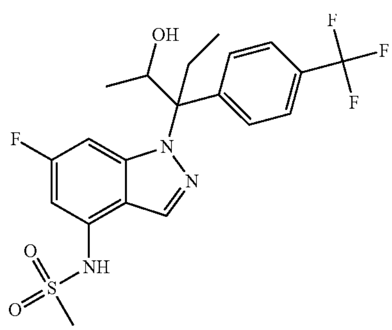 [SMILES: CCC(c1ccc(C(F)(F)F)cc1)(C(C)O)n1ncc2c(NS(C)(=O)=O)cc(F)cc21] | N-(6-fluoro-1-(2-hydroxy-3-(4-(trifluoromethyl)phenyl)pentan-3-yl)-1H-indazol-4-yl)methanesulfonamide (diastereomer C) | 459.8 |
| 34 | 1138 | 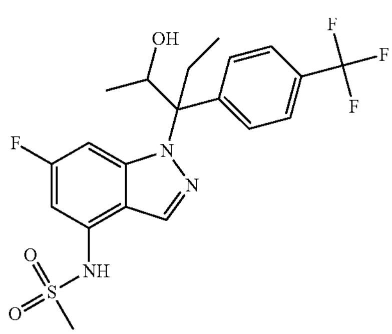 [SMILES: CCC(c1ccc(C(F)(F)F)cc1)(C(C)O)n1ncc2c(NS(C)(=O)=O)cc(F)cc21] | N-(6-fluoro-1-(2-hydroxy-3-(4-(trifluoromethyl)phenyl)pentan-3-yl)-1H-indazol-4-yl)methanesulfonamide (diastereomer D) | 459.8 |

Example 10
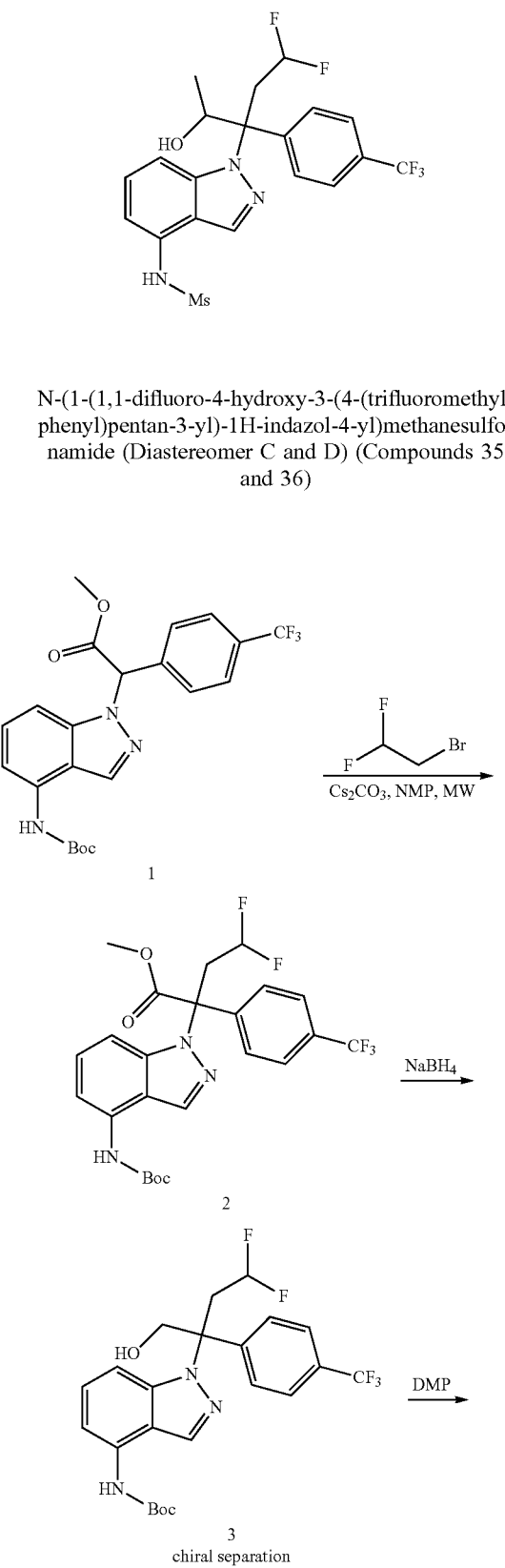
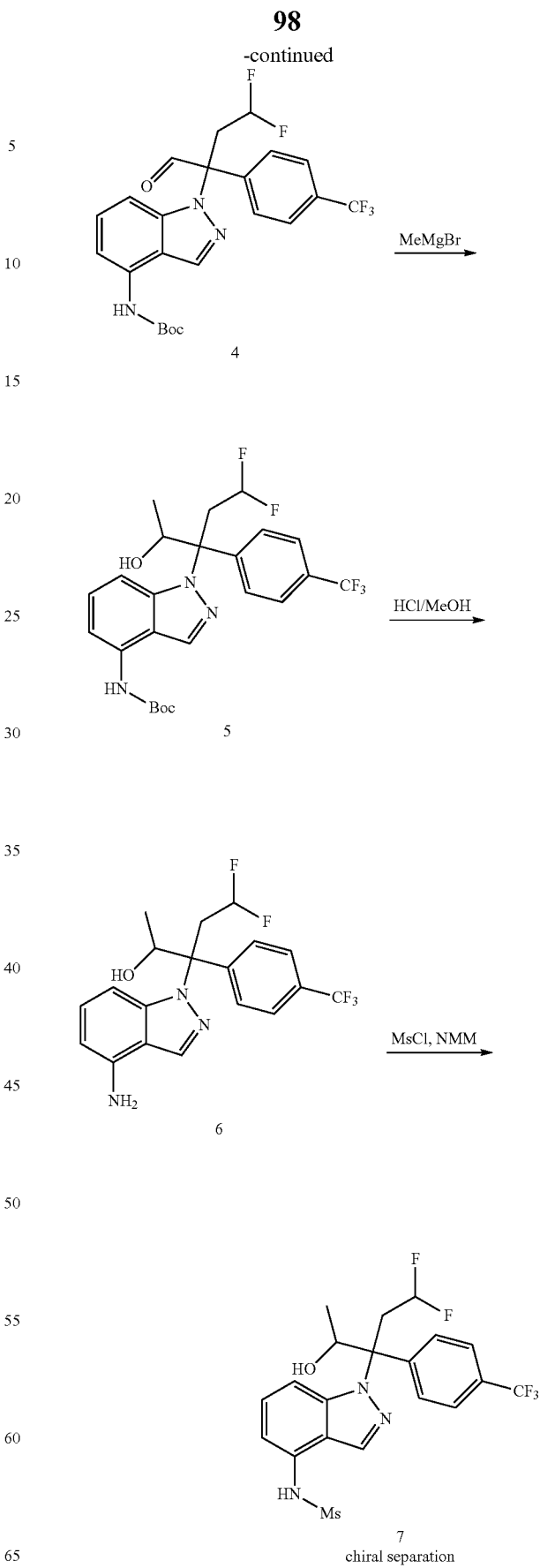
N-(1-(1,1-difluoro-4-hydroxy-3-(4-(trifluoromethyl)phenyl)pentan-3-yl)-1H-indazol-4-yl)methanesulfonamide (Diastereomer C and D) (Compounds 35 and 36)

Step A: Methyl 2-(4-(tert-butoxycarbonylamino)-1H-indazol-1-yl)-4,4-difluoro-2-(4-(trifluoromethyl)phenyl)butanoate

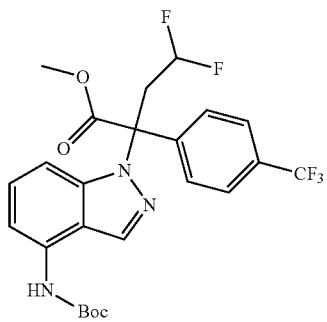 [SMILES: COC(=O)C(CC(F)F)(c1ccc(C(F)(F)F)cc1)n1ncc2c(NC(=O)OC(C)(C)C)cccc21]

To a solution of methyl 2-(4-(tert-butoxycarbonylamino)-1H-indazol-1-yl)-2-(4-(trifluoromethyl)phenyl)acetate (2 g, 4.45 mmol, precursor compound 6 during preparation of Intermediate IA) in NMP (5 mL) was added $Cs_2CO_3$ (2.9 g, 8.9 mmol) and 2-bromo-1,1-difluoroethane (1.3 g, 8.9 mmol) at rt. The reaction mixture was stirred at 70° C. under MW for 2 h, and then diluted with $H_2O$ (10 mL). The aqueous layer was extracted with ethyl acetate (10 mL x 3) and the combined organics were washed with brine (10 mL), dried over anhydrous sodium sulfate, filtered and concentrated in vacuo. The crude product was purified by column chrotomagraphy (petroleum ether/ethyl acetate=20/1) to give the target product. LC/MS (m/z): 514.1 [M+1]. The racemic product was resolved by Prep-Chiral-SCF (Column: OJ-H, Mobile phase: SCF (2.55 mL/min)/IPA:MeOH (1:9, 0.1% DEA, 0.45 mL/min), Column Temp: 40° C.) to give the enantiomer A (Rt=1.87 min) and enantiomer B (Rt=2.5 min).

Step B: tert-butyl 1-(4,4-difluoro-1-hydroxy-2-(4-(trifluoromethyl)phenyl)butan-2-yl)-1H-indazol-4-ylcarbamate (enantiomer B)

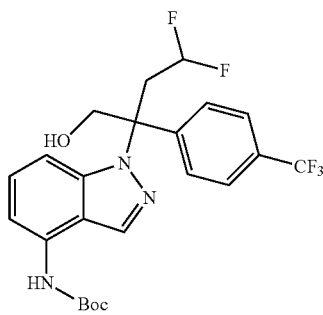 [SMILES: CC(C)(C)OC(=O)Nc1cccc2c1cnn2C(CO)(CC(F)F)c1ccc(C(F)(F)F)cc1]

To a solution of methyl 2-(4-(tert-butoxycarbonylamino)-1H-indazol-1-yl)-4,4-difluoro-2-(4-(trifluoromethyl)phenyl)butanoate (200 mg, 0.39 mmol, enantiomer B from Step A above) in MeOH (5 mL) was added $NaBH_4$ (148 mg, 3.9 mmol) at rt. The reaction mixture was stirred at rt for 2 h, then quenched with saturated $NH_4Cl$ solution (20 mL). The aqueous was extracted with ethyl acetate (10 mL×3) and the combined organics were washed with brine (10 mL), dried over anhydrous sodium sulfate, filtered and concentrated in vacuo to give the title compound, which was used in the next step without further purification. LC/MS (m/z): 486.2 [M+1].

Step C: tert-butyl 1-(4,4-difluoro-1-oxo-2-(4-(trifluoromethyl)phenyl)butan-2-yl)-1H-indazol-4-ylcarbamate (Enantiomer B)

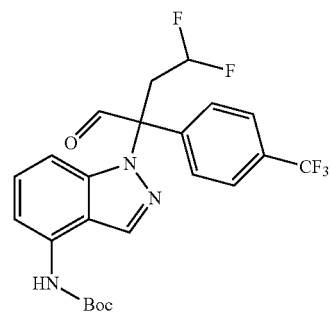 [SMILES: CC(C)(C)OC(=O)Nc1cccc2c1cnn2C(C=O)(CC(F)F)c1ccc(C(F)(F)F)cc1]

To a solution of tert-butyl 1-(4,4-difluoro-1-hydroxy-2-(4-(trifluoromethyl)phenyl) butan-2-yl)-1H-indazol-4-ylcarbamate (270 mg, 0.56 mmol) from step B in DCM (4 mL) was added Dess-Martin Periodinane (472 mg, 1.1 mmol) at rt. The reaction mixture was stirred at rt for 2 h, then diluted with saturated $NH_4Cl$ solution (10 mL). The aqueous was extracted with ethyl acetate (10 mL×3) and the combined organics were washed with brine (10 mL), dried over anhydrous sodium sulfate, filtered and concentrated in vacuo. The crude was purified by column chrotomagraphy (petroleum ether/ethyl acetate=20/1) to give the target product. LC/MS (m/z): 484.1 [M+1].

Step D: tert-butyl 1-(1,1-difluoro-4-hydroxy-3-(4-(trifluoromethyl)phenyl)pentan-3-yl)-1H-indazol-4-ylcarbamate (diastereomers)

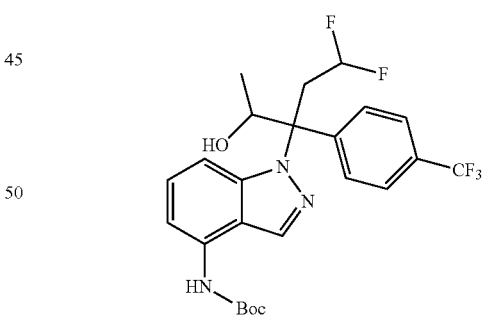

To a solution of tert-butyl 1-(4,4-difluoro-1-oxo-2-(4-(trifluoromethyl)phenyl)butan-2-yl)-1H-indazol-4-ylcarbamate (130 mg, 0.269 mmol) in THF (2 mL) was added $CH_3MgBr$ (0.2 mL, 0.6 mmol, 3M in THF) at 0° C. The reaction mixture was stirred at rt for 2 h, then quenched with saturated $NH_4Cl$ solution (10 mL). The aqueous layer was extracted with ethyl acetate (10 mL x 3) and the combined organics were washed with brine (10 mL), dried over anhydrous sodium sulfate, filtered and concentrated in vacuo to give the title compound without further purification. LC/MS (m/z): 500.2 [M+1].

Step E: 3-(4-amino-1H-indazol-1-yl)-5,5-difluoro-3-(4-(trifluoromethyl)phenyl)pentan-2-ol (diastereomers)

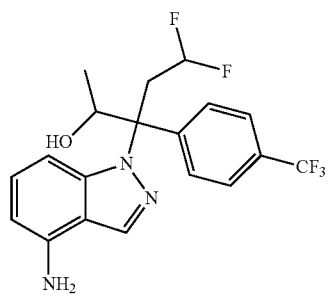 [SMILES: CC(O)C(CC(F)F)(c1ccc(C(F)(F)F)cc1)n1ncc2c(N)cccc21]

To a solution of tert-butyl 1-(1,1-difluoro-4-hydroxy-3-(4-(trifluoromethyl)phenyl)pentan-3-yl)-1H-indazol-4-ylcarbamate (120 mg, 0.24 mmol) in MeOH (5 mL) was added 4N HCl/MeOH (5 mL) at rt. After stirring at rt for 2 h, the volatile was concentrated in vacuo to give the title compound without further purification. LC/MS (m/z): 400.2 [M+1].

Step F: N-(1-(1,1-difluoro-4-hydroxy-3-(4-(trifluoromethyl)phenyl)pentan-3-yl)-1H-indazol-4-yl)methanesulfonamide (Diastereomer C and D) (Compounds 35 and 36)

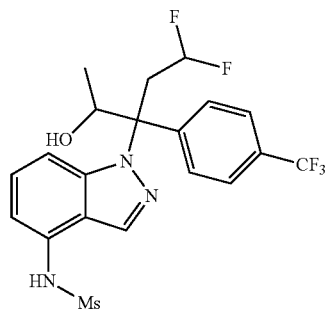 [SMILES: CC(O)C(CC(F)F)(c1ccc(C(F)(F)F)cc1)n1ncc2c(NS(C)(=O)=O)cccc21]

To a solution of 3-(4-amino-1H-indazol-1-yl)-5,5-difluoro-3-(4-(trifluoromethyl)phenyl) pentan-2-ol (120 mg, 0.30 mmol) in DCM (10 mL) was added NMM (60 mg, 0.6 mmol) and MsCl (69 mg, 0.6 mmol) at rt. The reaction mixture was stirred at rt for 2 h, then quenched with saturated NH$_4$Cl solution (10 mL). The aqueous layer was extracted with ethyl acetate (10 mL x 3) and the combined organics were washed with brine (10 mL), dried over anhydrous sodium sulfate, filtered and concentrated in vacuo. The residue was purified by PREP-HPLC (Mobile phase: acetonitrile/water (10 mM NH$_4$HCO$_3$)) to give title product as white solid. LC/MS (m/z): 478.1 [M+1]. The diaseteromeric product was resolved by Prep-Chiral-SCF (Column: OD-H, Mobile phase: CO$_2$ (2.75 mL/min)/MeOH (0.1% EDA, 0.25 mL/min), Column Temp: 40° C.) to give the diastereomer C (Rt=2.59 min) and diastereomer D (Rt=3.66 min).

Diastereomer C (Compound 35): $^1$H NMR (400 MHz, CDCl$_3$) δ 8.42 (s, 1H), 7.63-7.61 (d, J=8.4 Hz, 2H), 7.26-7.25 (d, J=8.0 Hz, 2H), 7.13-7.11 (m, 1H), 7.08-7.06 (m, 1H), 6.45-6.14 (m, 2H), 4.49-4.81 (m, 1H), 3.25-3.11 (m, 5H), 1.05-1.02 (d, J=6.4 Hz, 3H).

Diastereomer D (Compound 36): $^1$H NMR (400 MHz, CDCl$_3$) δ 8.43 (s, 1H), 7.63-7.60 (d, J=8.4 Hz, 2H), 7.29-7.27 (d, J=8.0 Hz, 2H), 7.17-7.15 (m, 1H), 7.11-7.07 (m, 1H), 6.20-6.17 (d, J=8.4 Hz, 1H), 5.23-5.22 (m, 2H), 3.12 (s, 3H), 3.08-3.02 (m, 2H), 1.10-1.09 (d, J=6.4 Hz, 3H).

Example 11

N-(1-(1,1-difluoro-4-hydroxy-3-(4-(trifluoromethyl)phenyl)pentan-3-yl)-1H-indazol-4-yl)methanesulfonamide (Diastereomer A and B) (Compounds 37 and 38)

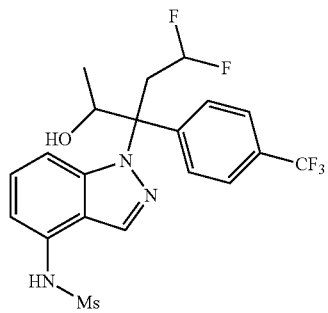 [SMILES: CC(O)C(CC(F)F)(c1ccc(C(F)(F)F)cc1)n1ncc2c(NS(C)(=O)=O)cccc21]

Using the procedures described in Example 10 Steps B~F, but starting with enantiomer A from Step A, Compounds 37 and 38 of Table 8 were prepared respectively. For Compound 37 (Diastereomer A), the following final chiral separation conditions apply: SCF, column: AS-H, Rt=2.93 min. For Compound 38 (Diastereomer B), the following final chiral separation conditions apply: SCF, column: AS-H, Rt=3.35 min. Diastereomer A (Compound 37): $^1$H NMR (400 MHz, CDCl$_3$) δ 8.42 (s, 1H), 7.63-7.60 (d, J=8.4 Hz, 2H), 7.29-7.27 (d, J=8.0 Hz, 2H), 7.18-7.15 (m, 1H), 7.12-7.08 (m, 1H), 6.20-6.18 (d, J=8.4 Hz, 1H), 5.32-5.18 (m, 2H), 3.05 (s, 3H), 3.09-3.02 (m, 2H), 1.10-1.096 (d, J=6.4 Hz, 3H).

Diastereomer B (Compound 38): $^1$H NMR (400 MHz, CDCl$_3$) δ 8.42 (s, 1H), 7.59-7.57 (d, J=8.0 Hz, 2H), 7.22-7.20 (d, J=7.6 Hz, 2H), 7.05-7.70 (m, 1H), 6.97-6.12 (m, 2H), 4.91-4.86 (m, 1H), 3.25-3.19 (m, 1H), 3.12-3.04 (m, 4H), 1.00-0.96 (d, J=6.4 Hz, 3H).

Example 12

N-(1-(1,1-difluoro-4-hydroxy-3-(4-(trifluoromethyl)phenyl)hexan-3-yl)-1H-indazol-4-yl)methanesulfonamide (Diastereomer C and D) (Compounds 39 and 40)

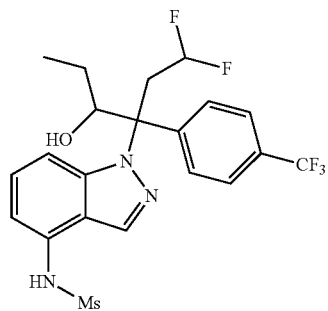 [SMILES: CCC(O)C(CC(F)F)(c1ccc(C(F)(F)F)cc1)n1ncc2c(NS(C)(=O)=O)cccc21]

Using the procedure described in Example 10 in Steps D through F, but replacing methylmagnesium bromide with ethylmagnesium bromide in step D, Compounds 39 and 40 of Table 8 were prepared respectively. For Compound 39, the following final chiral separation conditions apply: SCF, column: OD-H, Rt=4.39 min. For Compound 40, the following final chiral separation conditions apply: SCF, column: OD-H, Rt=5.44 min. Diastereomer C (Compound 39): $^1$H NMR (400 MHz, CDCl$_3$) δ 8.35 (s, 1H), 7.62-7.60 (d, J=8.4 Hz, 2H), 7.27-7.25 (d, J=8.4 Hz, 2H), 7.23-7.03 (m, 2H), 7.31-7.203 (m, 2H), 4.61-4.58 (d, J=10.4 Hz, 1H), 3.19-3.05 (m, 5H), 1.40-1.36 (m, 1H), 1.21-1.12 (m, 1H), 0.98-0.95 (t, 3H).

Diastereomer D (Compound 40): $^1$H NMR (400 MHz, CDCl$_3$) δ 8.38 (s, 1H), 7.62-7.60 (d, J=8.4 Hz, 2H), 7.30-7.28 (d, J=8.4 Hz, 2H), 7.16-7.09 (m, 2H), 6.17-6.15 (d, J=8.4 Hz, 1H), 5.18-5.17 (m, 1H), 4.90-4.87 (d, J=10.4 Hz, 1H), 4.13 (s, 1H), 3.12-2.96 (m, 5H), 1.62-1.57 (m, 1H), 1.07-0.90 (t, 3H), 0.89-0.86 (m, 1H).

Example 13

N-(1-(1,1-difluoro-4-hydroxy-3-(4-(trifluoromethyl)phenyl)hexan-3-yl)-1H-indazol-4-yl)methanesulfonamide (Diastereomer A and B) (Compound 41 and 42)

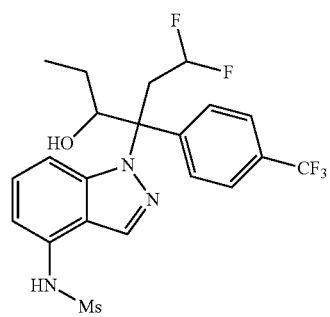 [SMILES: CCC(O)C(CC(F)F)(c1ccc(C(F)(F)F)cc1)n1ncc2c(NS(C)(=O)=O)cccc21]

Using the procedure described in Example 10 in Steps B through F, but using enantiomer A from Step A and ethylmagnesium bromide replacement of methylmagnesium bromide in step D, Compounds 41 and 42 of Table 8 were prepared respectively. For Compound 41, the following final chiral separation conditions apply: SCF, column: OD-H, Rt=3.15 min. For Compound 42, the following final chiral separation conditions apply: SCF, column: OD-H, Rt=4.17 min.

TABLE 8

| Compound No. | IP (nM) | Structure | IUPAC Name | Exact Mass [M + H]+ |
| --- | --- | --- | --- | --- |
| 35 | 50 | 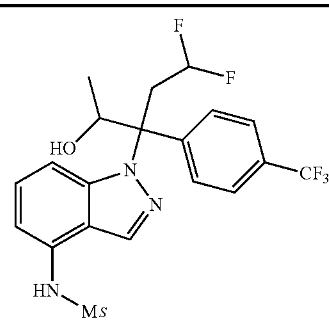 | N-(1-(1,1-difluoro-4-hydroxy-3-(4-(trifluoromethyl)phenyl)pentan-3-yl)-1H-indazol-4-yl)methanesulfonamide (Diastereomer C) | 478.1 |
| 36 | 95 | 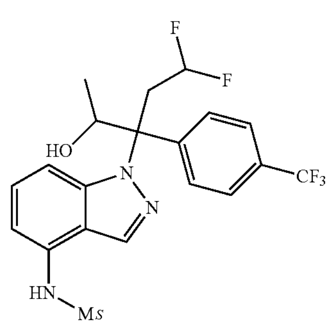 | N-(1-(1,1-difluoro-4-hydroxy-3-(4-(trifluoromethyl)phenyl)pentan-3-yl)-1H-indazol-4-yl)methanesulfonamide (Diastereomer D) | 478.1 |

TABLE 8-continued

| Compound No. | IP (nM) | Structure | IUPAC Name | Exact Mass [M + H]+ |
|---|---|---|---|---|
| 37 | 66 | 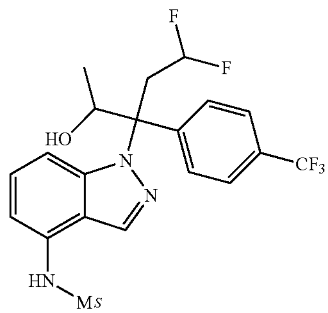 | N-(1-(1,1-difluoro-4-hydroxy-3-(4-(trifluoromethyl)phenyl)pentan-3-yl)-1H-indazol-4-yl)methanesulfonamide (Diastereomer A) | 478.1 |
| 38 | 596 | 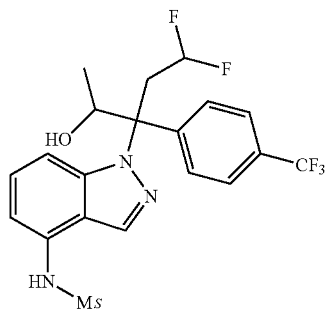 | N-(1-(1,1-difluoro-4-hydroxy-3-(4-(trifluoromethyl)phenyl)pentan-3-yl)-1H-indazol-4-yl)methanesulfonamide (Diastereomer B) | 478.1 |
| 39 | 23 | 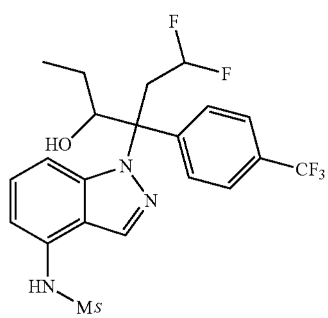 | N-(1-(1,1-difluoro-4-hydroxy-3-(4-(trifluoromethyl)phenyl)hexan-3-yl)-1H-indazol-4-yl)methanesulfonamide (Diastereomer C) | 492.1 |
| 40 | 15 | 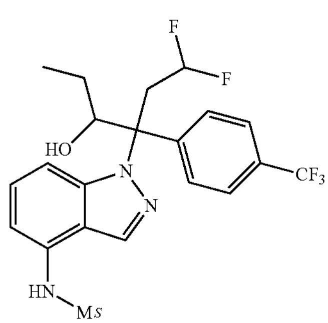 | N-(1-(1,1-difluoro-4-hydroxy-3-(4-(trifluoromethyl)phenyl)hexan-3-yl)-1H-indazol-4-yl)methanesulfonamide (Diastereomer D) | 492.1 |

TABLE 8-continued

| Compound No. | IP (nM) | Structure | IUPAC Name | Exact Mass [M + H]+ |
|---|---|---|---|---|
| 41 | 543 | 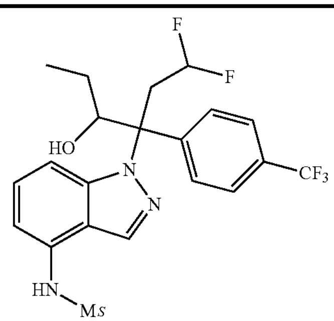 | N-(1-(1,1-difluoro-4-hydroxy-3-(4-(trifluoromethyl)phenyl)hexan-3-yl)-1H-indazol-4-yl)methanesulfonamide (Diastereomer A) | 492.1 |
| 42 | 1372 | 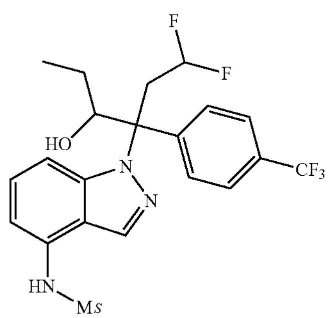 | N-(1-(1,1-difluoro-4-hydroxy-3-(4-(trifluoromethyl)phenyl)hexan-3-yl)-1H-indazol-4-yl)methanesulfonamide (Diastereomer B) | 492.1 |

Compound 35 exhibited good metabolic stability in liver microsome and hepatocytes of multiple animal species. Additionally, Compound 35 exhibited a good PK profile in rats. The PK profile for Compound 35 is shown below:

| Cl (mL/min/kg) | $t_{1/2}$ (hours) | AUCN po ($\mu M \cdot h \cdot kg/mg$) | % F |
|---|---|---|---|
| 14 | 7.0 | 2.7 | 98 |

Below is the metabolic stability for Compound 37:

| | Human | Rat | Dog | Rhesus Monkey |
|---|---|---|---|---|
| Liver Microsome Stability ($t_{1/2}$) | 86 mins | 122 mins | 58 mins | 123 mins |
| Hepatocyte Stability ($t_{1/2}$) | >90 mins | >90 mins | 79 mins | >90 mins |

Example 14

N-(1-(4,4-difluoro-1-hydroxy-2-(4-(trifluoromethyl)phenyl)butan-2-yl)-1H-indazol-4-yl)methanesulfonamide (Enantiomer A) (Compound 43)

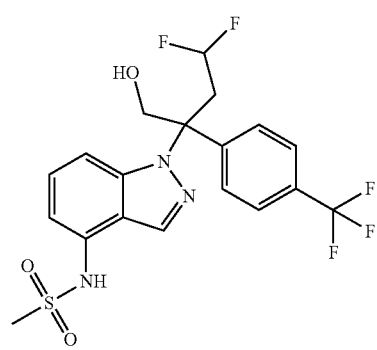 [SMILES: CS(=O)(=O)Nc1cccc2c1cnn2C(CO)(CC(F)F)c1ccc(C(F)(F)F)cc1]

Step A: Methyl 2-(4-amino-1H-indazol-1-yl)-4,4-difluoro-2-(4-(trifluoromethyl)phenyl) butanoate (enantiomer A) (Compound 431

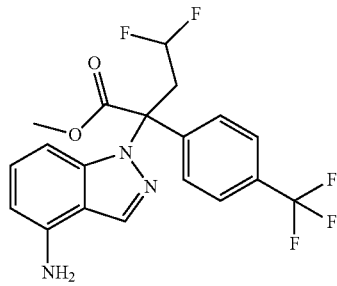 [SMILES: COC(=O)C(CC(F)F)(c1ccc(C(F)(F)F)cc1)n1ncc2c(N)cccc21]

A mixture of methyl 2-(4-(tert-butoxycarbonylamino)-1H-indazol-1-yl)-4,4-difluoro-2-(4-(trifluoromethyl)phenyl)butanoate (102 mg, 0.2 mmol, enantiomer A from Example 10 in step A) and 4N HCl/MeOH (5 mL) was stirred at rt for 1 h. Then the reaction mixture was concentrated in vacuo to give the crude product, which was used for the next step without purification. LC/MS (m/z): 414.2 [M+1].

Step B: Methyl 4,4-difluoro-2-(4-(methylsulfonamido)-1H-indazol-1-yl)-2-(4-(trifluoromethyl) phenyl)butanoate (enantiomer A)

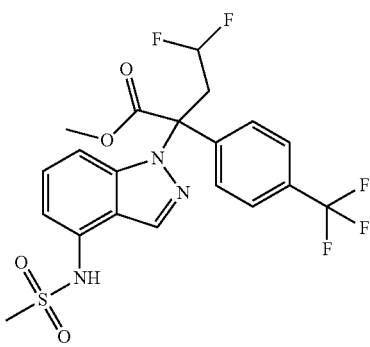 [SMILES: COC(=O)C(CC(F)F)(c1ccc(C(F)(F)F)cc1)n1ncc2c(NS(C)(=O)=O)cccc21]

To a solution of methyl 2-(4-amino-1H-indazol-1-yl)-4,4-difluoro-2-(4-(trifluoromethyl) phenyl)butanoate (79 mg, 0.19 mmol) from step A in dry dichloromethane (1.5 mL) was added 4-methylmorpholine (200 uL, 1.88 mmol) and MsCl (21 uL, 0.282 mmol) successively at rt. After stirring at rt for 1 h, the mixture was quenched with ice water (5 mL). The organic layer was separated and the aqueous was extracted with ethyl acetate (6 mL×5). The combined organic layer was dried over anhydrous Na₂SO₄, filtered and concentrated. The residue was purified by PREP-TLC (eluent: 35% ethyl acetate in petroleum ether) to afford the title compound. LC/MS (m/z): 492.1 [M+1].

Step C: N-(1-(4,4-difluoro-1-hydroxy-2-(4-(trifluoromethyl)phenyl)butan-2-yl)-1H-indazol-4-yl)methanesulfonamide (Enantiomer A)

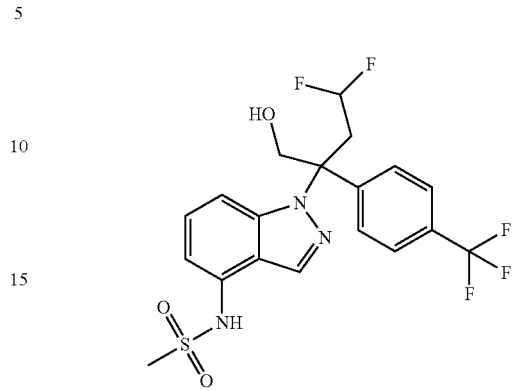

To a solution of methyl 4,4-difluoro-2-(4-(methylsulfonamido)-1H-indazol-1-yl)-2-(4-(trifluoromethyl)phenyl)butanoate from Step B (50 mg, 0.1 mmol) in methanol (2 mL) was added NaBH₄ (20 mg, 0.51 mmol) at rt. The mixture was stirred at rt for 1 h, then quenched with ice saturated NH₄Cl solution (3 mL), MeOH was removed in vacuo and the water layer was extracted with ethyl acetate (5 mL×4). The organic layer was combined and dried over Na₂SO₄, filtered and concentrated. The residue was purified by PREP-TLC (eluent: 33% ethyl acetate in petroleum ether) to afford the title compound. LC/MS (m/z): 464.1 [M+1]. Enantiomer A (Compound 43): ¹H NMR (400 MHz, CDCl₃) δ 8.31 (s, 1H), 7.63-7.61 (d, J=8.4 Hz, 2H), 7.30-7.26 (d, J=8.3 Hz, 1H), 7.25-7.23 (m, 2H), 7.17-7.12 (m, 2H), 6.38-6.35 (m, 1H), 6.10-5.80 (m, 1H), 4.45-4.43 (m, 1H), 4.30-4.25 (m, 1H), 4.10-4.09 (m, 1H), 3.18-3.09 (m, 5H).

Example 15

N-(1-(4,4-difluoro-1-hydroxy-2-(4-(trifluoromethyl)phenyl)butan-2-yl)-1H-indazol-4-yl)methanesulfonamide (Enantiomer B) (Compound 44)

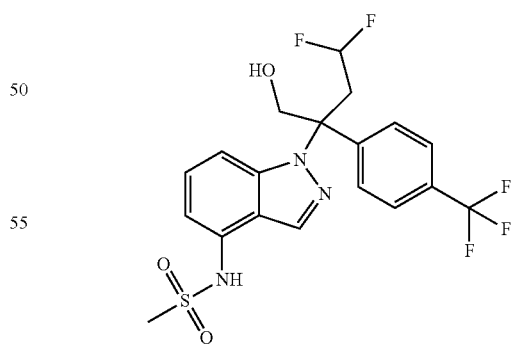

Using the procedures described in Example 14 Steps A~C, but starting with enantiomer B in Step A, Examples 15 of Table 8 was prepared. Enantiomer B: ¹H NMR (400 MHz, CDCl₃) δ 8.38 (s, 1H), 7.77 (s, 1H), 7.63-7.61 (d, J=8.4 Hz, 2H), 7.28-7.23 (m, 2H), 7.18-7.11 (m, 2H), 6.38-6.35 (d, J=8 Hz, 1H), 5.93 (m, 1H), 4.43 (m, 3H), 3.18-3.09 (m, 5H).

TABLE 9

| Compound Number | IP (nM) | Structure | IUPAC Name | Exact Mass [M + H]+ |
|---|---|---|---|---|
| 43 | 388 | 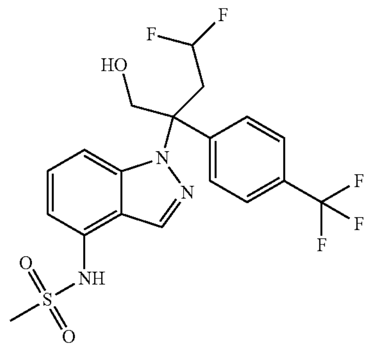 [SMILES: CS(=O)(=O)Nc1cccc2c1cnn2C(CO)(CC(F)F)c1ccc(C(F)(F)F)cc1] | N-(1-(4,4-difluoro-1-hydroxy-2-(4-(trifluoromethyl)phenyl)butan-2-yl)-1H-indazol-4-yl)methanesulfonamide (Enantiomer A) | 464.1 |
| 44 | 539 | 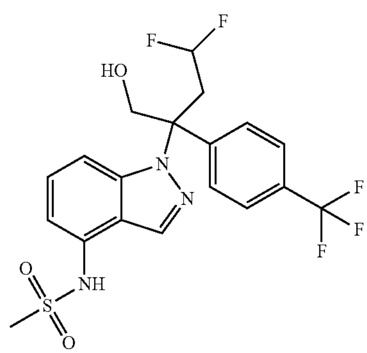 [SMILES: CS(=O)(=O)Nc1cccc2c1cnn2C(CO)(CC(F)F)c1ccc(C(F)(F)F)cc1] | N-(1-(4,4-difluoro-1-hydroxy-2-(4-(trifluoromethyl)phenyl)butan-2-yl)-1H-indazol-4-yl)methanesulfonamide (Enantiomer B) | 464.1 |

Example 16

4,4-difluoro-2-(4-(methylsulfonamido)-1H-indazol-1-yl)-2-(4-(trifluoromethyl)phenyl) butanamide (Enantiomer B) (Compound 45)

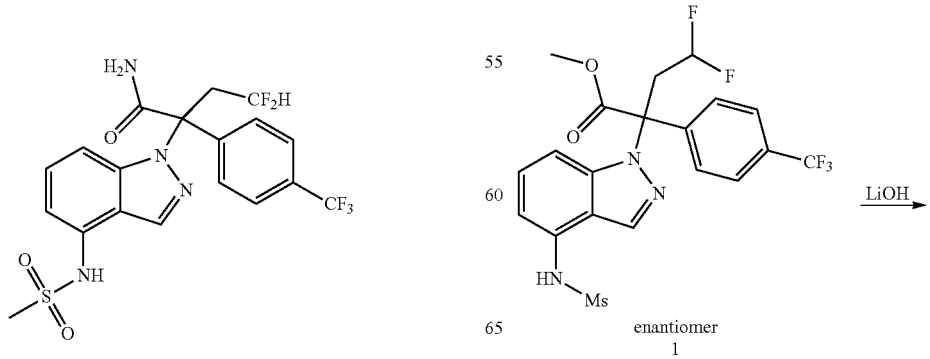

-continued

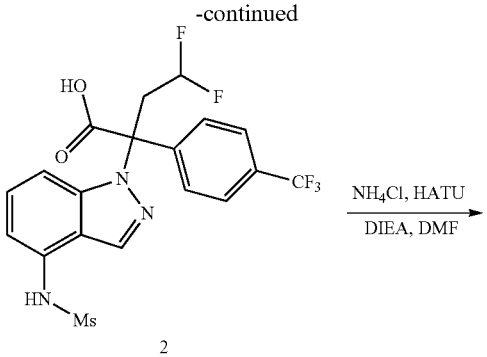

2

NH₄Cl, HATU
―――――→
DIEA, DMF

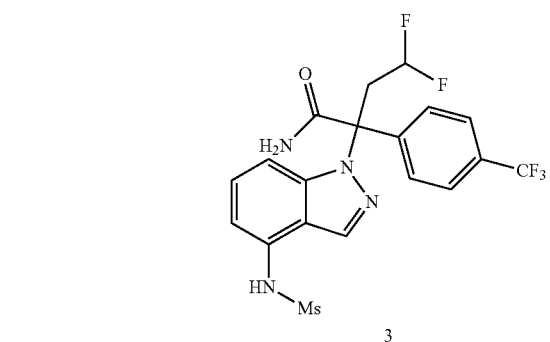

3

Step A: 4,4-difluoro-2-(4-(methylsulfonamido)-1H-indazol-1-yl)-2-(4-(trifluoromethyl)phenyl) butanoic acid (Enantiomer A)

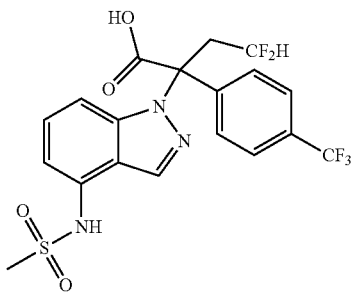 [SMILES: CS(=O)(=O)Nc1cccc2c1cnn2C(CC(F)F)(C(=O)O)c1ccc(C(F)(F)F)cc1]

Methyl 4,4-difluoro-2-(4-(methylsulfonamido)-1H-indazol-1-yl)-2-(4-(trifluoromethyl)phenyl)butanoate (300 mg, 0.61 mmol) from Example 14 in step B in MeOH (5 mL) was added LiOH (128 mg, 3.05 mmol) and H₂O (1 mL) at rt. The reaction mixture was stirred at rt overnight, then the pH was adjusted to 4. The aqueous layer was extracted with ethyl acetate (10 mL×3) and the combined organics were washed with brine (10 mL), dried over sodium sulfate and concentrated in vacuo to give target compound, which was used for the next step without further purification. LC/MS (m/z): 478.2 [M+1].

Step B: 4,4-difluoro-2-(4-(methylsulfonamido)-1H-indazol-1-yl)-2-(4-(trifluoromethyl)phenyl) butanamide (Enantiomer B)

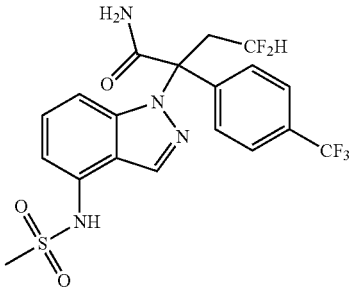

To a solution of 4,4-difluoro-2-(4-(methylsulfonamido)-1H-indazol-1-yl)-2-(4-(trifluoromethyl)phenyl)butanoic acid (240 mg, 0.50 mmol) in DMF (2 mL) was added DIPEA (129 mg, 1 mmol), HATU (380 mg, 1 mmol) and NH₄Cl (535 mg, 10.0 mmol). The reaction mixture was stirred at rt overnight, then diluted with saturated NaCl solution (10 mL). The aqueous layer was extracted with ethyl acetate (10 mL×3) and the combined organic layers were washed with brine (10 mL), dried over sodium sulfate and concentrated in vacuo. The crude oil was purified by Prep-HPLC (Mobile phase: acetonitrile/water (10 mM NH₄HCO₃)) to give the target compound. LC/MS (m/z): 477.2 [M+1]. Enantiomer B: $^1$H NMR (400 MHz, CDCl₃) δ 7.40-7.35 (m, 5H), 7.20-7.18 (m, 2H), 7.06-7.02 (m, 1H), 6.79-6.78 (d, J=3.6 Hz, 1H), 6.63-6.62 (d, J=4.4 Hz, 1H), 5.58-5.57 (m, 3H), 3.30-3.08 (m, 2H), 3.04 (s, 3H).

Example 17

4,4-difluoro-2-(4-(methylsulfonamido)-1H-indazol-1-yl)-2-(4-(trifluoromethyl)phenyl) butanamide (Enantiomer A) (Compound 46)

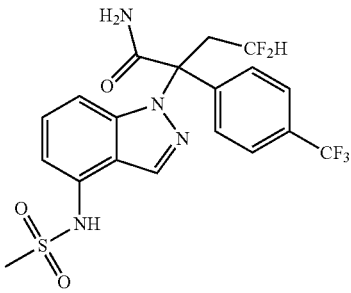

Using the procedures described in Example 14 Steps A~B and Example 16 Steps A~B, but starting with enantiomer B from Example 10 Step A in Step A of Example 14, Compound 46 of Table 9 was prepared. Enantiomer B: $^1$H NMR (400 MHz, CDCl₃) δ 7.40-7.35 (m, 4H), 7.26 (m, 1H), 7.27-7.26 (d, J=4 Hz, 1H), 7.20-7.18 (d, J=5.6 Hz, 1H), 7.05-7.02 (m, 1H), 6.80-6.79 (s, 1H), 6.63-6.62 (d, J=6.4 Hz, 1H), 5.94 (s, 1H), 5.82-5.60 (m, 2H), 3.29-3.13 (m, 2H), 3.05 (s, 3H).

TABLE 10

| Compound Number | IP (nM) | Structure | IUPAC Name | Exact Mass [M + H]+ |
|---|---|---|---|---|
| 45 | 274 | 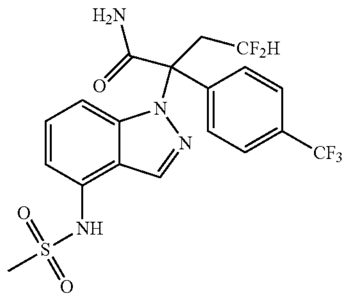 [SMILES: CS(=O)(=O)Nc1cccc2c1cnn2C(CC(F)F)(C(N)=O)c1ccc(C(F)(F)F)cc1] | 4,4-difluoro-2-(4-(methylsulfonamido)-1H-indazol-1-yl)-2-(4-(trifluoromethyl)phenyl)butanamide (Enantiomer B) | 477.0 |
| 46 | 76 | 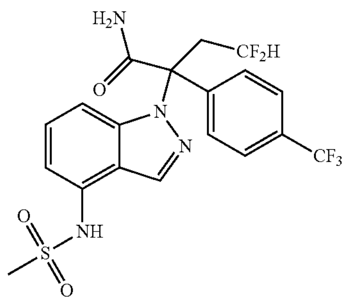 [SMILES: CS(=O)(=O)Nc1cccc2c1cnn2C(CC(F)F)(C(N)=O)c1ccc(C(F)(F)F)cc1] | 4,4-difluoro-2-(4-(methylsulfonamido)-1H-indazol-1-yl)-2-(4-(trifluoromethyl)phenyl)butanamide (Enantiomer A) | 477.0 |

Compound 46 exhibited good metabolic stability in liver microsome and hepatocytes of multiple animal species. Additionally, Compound 46 exhibited a good PK profile in rats. The PK profile for Compound 46 is shown below:

| Cl (mL/min/kg) | $t_{1/2}$ (hours) | AUCN po (µM · h · kg/mg) | % F |
|---|---|---|---|
| 6.2 | 4.2 | 1.9 | 31 |

Below is the metabolic stability for Compound 46:

| | Human | Rat | Dog | Rhesus Monkey |
|---|---|---|---|---|
| Liver Microsome Stability ($t_{1/2}$) | 138 mins | 97 mins | 135 mins | 92 mins |
| Hepatocyte Stability ($t_{1/2}$) | >90 mins | >90 mins | >90 mins | >90 mins |

Example 18

N-(1-(1,1-difluoro-2-hydroxy-3-(4-(trifluoromethyl)phenyl)pentan-3-yl)-1H-indazol-4-yl)methanesulfonamide (Diastereomer A and B)

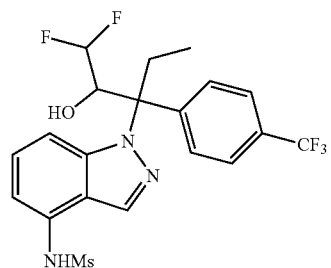

Step A: tert-butyl 1-(1-hydroxy-2-(4-(trifluoromethyl)phenyl)butan-2-yl)-1H-indazol-4-ylcarbamate

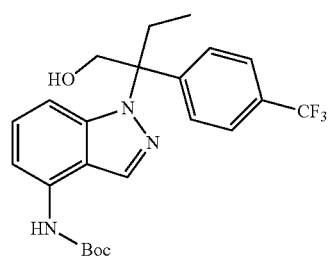 [SMILES: CCC(CO)(c1ccc(C(F)(F)F)cc1)n1ncc2c(NC(=O)OC(C)(C)C)cccc21]

To a solution of methyl 2-(4-(tert-butoxycarbonylamino)-1H-indazol-1-yl)-2-(4-(trifluoromethyl)phenyl)butanoate (Intermeidate IA, enantiomer A) (200 mg, 0.42 mmol) in THF (5 mL) was added LiBH$_4$ (0.63 mL, 1.25 mmol, 2M in THF) at rt. The reaction mixture was stirred at rt for 2 h, then quenched with saturated NH$_4$Cl solution (20 mL). The aqueous layer was extracted with ethyl acetate (10 mL×3) and the organic phase was washed with brine (10 mL), dried over sodium sulfate, filtered and concentrated in vacuo to give the title compound, which was used in the next step without further purification. LC/MS (m/z): 450.2 [M+1].

Step B: tert-butyl 1-(1-oxo-2-(4-(trifluoromethyl)phenyl)butan-2-yl)-1H-indazol-4-ylcarbamate

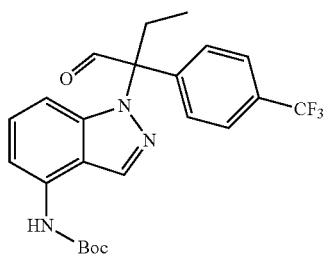 [SMILES: CCC(C=O)(c1ccc(C(F)(F)F)cc1)n1ncc2c(NC(=O)OC(C)(C)C)cccc21]

To a solution of tert-butyl 1-(1-hydroxy-2-(4-(trifluoromethyl)phenyl)butan-2-yl)-1H-indazol-4-ylcarbamate from Step A above (300 mg, 0.67 mmol) in DCM (4 mL) was added Dess-Martin periodinane (310 mg, 0.73 mmol) at rt. The reaction mixture was stirred at rt for 2 h, then diluted with saturated NH$_4$Cl solution (40 mL) was added. The aqueous layer was extracted with ethyl acetate (20 mL×3) and washed with brine (10 mL), dried over sodium sulfate and concentrated in vacuo. The crude oil was purified by column chrotomagraphy (petroleum ether/ethyl acetate=20/1, v/v) to give the target product. LC/MS (m/z): 448.1 [M+1].

Step C: tert-butyl 1-(1-(diethoxyphosphoryl)-1,1-difluoro-2-hydroxy-3-(4-(trifluoromethyl) phenyl) pentan-3-yl)-1H-indazol-4-ylcarbamate

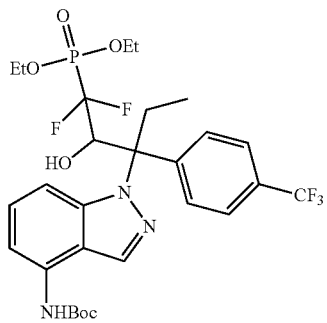 [SMILES: CCOP(=O)(OCC)C(F)(F)C(O)C(CC)(c1ccc(C(F)(F)F)cc1)n1ncc2c(NC(=O)OC(C)(C)C)cccc21]

To a solution of diethyl difluoromethylphosphonate (550 mg, 2.9 mmol) in anhydrous THF (2 mL) was added LDA (2.2 mL, 4.4 mmol, 2M in heptane/THF/ethylbenzene) at −78° C. After stirring at −78° C. for 0.5 h, a solution of tert-butyl 1-(1-oxo-2-(4-(trifluoromethyl)phenyl)butan-2-yl)-1H-indazol-4-ylcarbamate from Step B above (500 mg, 1.1 mmol) in THF (2 mL) was added to the mixture. The resulting mixture was gradually warmed to rt for 2 h and quenched with H$_2$O (10 mL). The aqueous layer was extracted with ethyl acetate (10 mL×3) and the organic phase was washed with brine (10 mL), dried over sodium sulfate, filtered and concentrated in vacuo to give the title compound, which was used in the next step without further purification. LC/MS (m/z): 636.1 [M+1].

Step D: diethyl 3-(4-amino-1H-indazol-1-yl)-1,1-difluoro-2-hydroxy-3-(4-(trifluoromethyl) phenyl) pentylphosphonate

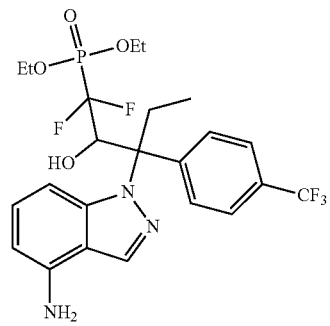 [SMILES: CCOP(=O)(OCC)C(F)(F)C(O)C(CC)(c1ccc(C(F)(F)F)cc1)n1ncc2c(N)cccc21]

To a solution of tert-butyl 1-(1-(diethoxyphosphoryl)-1,1-difluoro-2-hydroxy-3-(4-(trifluoromethyl)phenyl)pentan-3-yl)-1H-indazol-4-ylcarbamate from Step C above (450 mg, 0.71 mmol) in MeOH (2 mL) was added 4N HCl/MeOH (2 mL) at rt. After stirring at rt for 2 h, the mixture was quenched with saturated NaHCO$_3$ solution (10 mL). The aqueous layer was extracted with ethyl acetate (10 mL×3) and the organic phase was washed with brine (10 mL), dried over sodium sulfate, filtered and concentrated in vacuo to give the title compound, which was used in the next step without further purification. LC/MS (m/z): 536.1 [M+1].

Step E: diethyl 1,1-difluoro-2-hydroxy-3-(4-(methylsulfonamido)-1H-indazol-1-yl)-3-(4-(trifluoromethyl)phenyl)pentylphosphonate

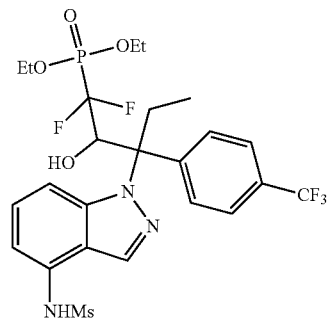

To a solution of diethyl 3-(4-amino-1H-indazol-1-yl)-1,1-difluoro-2-hydroxy-3-(4-(trifluoromethyl)phenyl)pentylphosphonate from Step D above (370 mg, 0.69 mmol) in DCM (5 mL) was added NMM (151 mg, 1.4 mmol) and MsCl (171 mg, 1.5 mmol) at rt. The reaction mixture was stirred at rt for 2 h, then diluted with saturated NH$_4$Cl solution (10 mL). The aqueous layer was extracted with ethyl acetate (10 mL×3) and the organic layer was washed with brine (10 mL), dried over sodium sulfate, filtered and concentrated in vacuo to give the title compound, which was used in the next step without further purification. LC/MS (m/z): 614.3 [M+1].

Step F: N-(1-(1,1-difluoro-2-hydroxy-3-(4-(trifluoromethyl)phenyl)pentan-3-yl)-1H-indazol-4-yl)methanesulfonamide (diastereomer A and B)

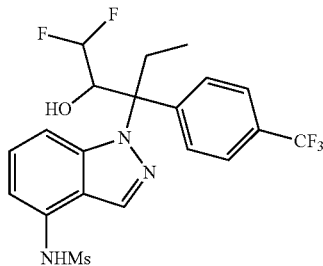

To a solution of diethyl 1,1-difluoro-2-hydroxy-3-(4-(methylsulfonamido)-1H-indazol-1-yl)-3-(4-(trifluoromethyl)phenyl)pentylphosphonate from Step E above (50 mg, 0.0815 mmol) in MeOH (5 mL) was added Na (18 mg, 0.78 mmol) at rt. After stirring at rt for 2 h, the reaction was quenched with saturated NH₄Cl solution (10 mL), and extracted with ethyl acetate (15 mL×3). The organic layers were washed with brine (10 mL), dried over sodium sulfate, filtered and concentrated in vacuo. The crude product was purified by PREP-HPLC (CH₃CN/H₂O (10 mM NH₄HCO₃)) to give the diastereomer A (Rt (LCMS: NH₄HCO₃)=1.91 min) and diastereomer B (Rt (LCMS: NH₄HCO₃)=1.94 min). LC/MS (m/z): 478.2 [M+1].

Diastereomer A: $^1$H NMR (400 MHz, CDCl₃) δ 8.29 (s, 1H), 7.65-7.63 (d, J=8.4 Hz, 2H), 7.34-7.32 (d, J=8.0, 2H), 7.15-7.08 (m, 2H), 6.31-6.29 (d, J=8.8, 1H), 5.91-5.63 (t, 1H), 5.08-5.02 (m, 1H), 3.13 (s, 3H), 2.95-2.90 (m, 1H), 2.62-2.56 (m, 1H), 1.25 (m, 1H), 0.65-0.61 (t, 3H).

Diastereomer B: $^1$H NMR (400 MHz, DMSO) δ 8.34 (s, 1H), 7.64-7.62 (d, J=8.4 Hz, 3H), 7.46-7.45 (d, J=7.6, 2H), 7.16-7.14 (d, J=7.2, 1H), 7.09-7.05 (m, 1H), 6.21-6.19 (d, J=8.4, 1H), 5.25-5.11 (m, 2H), 4.75 (s, 1H), 3.15 (s, 3H), 2.84-2.80 (m, 1H), 2.58-2.55 (m, 1H), 0.54-0.51 (t, 3H).

Using the procedures similar to those described in Example 18 and substitute ethanesulfonyl chloride for MsCl in Step E, Compounds 49 and 50 in Table 11 were prepared. Using procedures similar to those described for Compounds 47-50 and starting with the appropriate fluoroindazole intermediate, Compounds 51-54 in Table 11 were prepared.

TABLE 11

| Compound Number | IP (nM) | Structure | IUPAC Name | Exact Mass [M + H]+ |
|---|---|---|---|---|
| 47 | 11 | 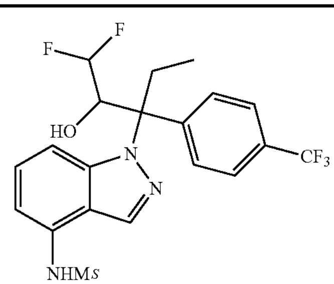 | N-(1-(1,1-difluoro-2-hydroxy-3-(4-(trifluoromethyl)phenyl)pentan-3-yl)-1H-indazol-4-yl)methanesulfonamide (Diastereomer A) | 478.2 |
| 48 | 6 | 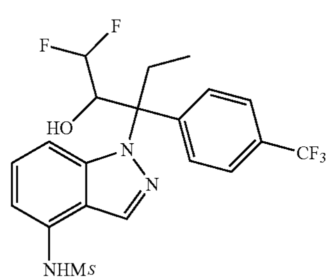 | N-(1-(1,1-difluoro-2-hydroxy-3-(4-(trifluoromethyl)phenyl)pentan-3-yl)-1H-indazol-4-yl)methanesulfonamide (Diastereomer B) | 478.2 |
| 49 | 7 | 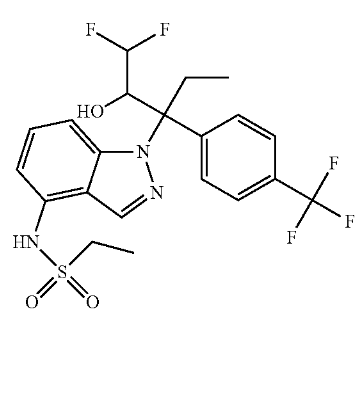 [SMILES: CCC(c1ccc(C(F)(F)F)cc1)(C(O)C(F)F)n1ncc2c(NS(=O)(=O)CC)cccc21] | N-(1-(1,1-difluoro-2-hydroxy-3-(4-(trifluoromethyl)phenyl)pentan-3-yl)-1H-indazol-4-yl)ethanesulfonamide (Diastereomer A) | 492.1 |

TABLE 11-continued

| Compound Number | IP (nM) | Structure | IUPAC Name | Exact Mass [M + H]+ |
|---|---|---|---|---|
| 50 | 4 | 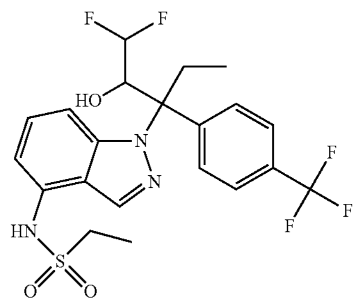 [SMILES: CCC(c1ccc(C(F)(F)F)cc1)(C(O)C(F)F)n1ncc2c(NS(=O)(=O)CC)cccc21] | N-(1-(1,1-difluoro-2-hydroxy-3-(4-(trifluoromethyl)phenyl)pentan-3-yl)-1H-indazol-4-yl)ethanesulfonamide (Diastereomer B) | 492.1 |
| 51 | 13 | 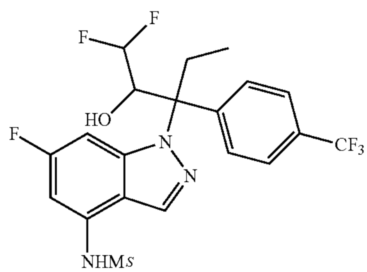 | N-(1-(1,1-difluoro-2-hydroxy-3-(4-(trifluoromethyl)phenyl)pentan-3-yl)-6-fluoro-1H-indazol-4-yl)methanesulfonamide (diastereomer A) | 496.1 |
| 52 | 28 | 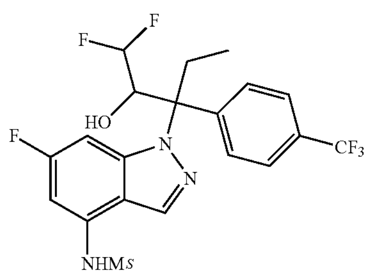 | N-(1-(1,1-difluoro-2-hydroxy-3-(4-(trifluoromethyl)phenyl)pentan-3-yl)-6-fluoro-1H-indazol-4-l)methanesulfonamide (diastereomer B) | 496.1 |
| 53 | 11 | 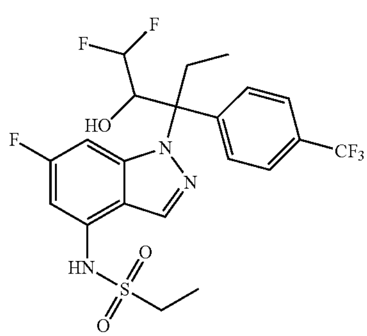 [SMILES: CCC(c1ccc(C(F)(F)F)cc1)(C(O)C(F)F)n1ncc2c(NS(=O)(=O)CC)cc(F)cc21] | N-(1-(1,1-difluoro-2-hydroxy-3-(4-(trifluoromethyl)phenyl)pentan-3-yl)-6-fluoro-1H-indazol-4-yl)ethanesulfonamide (diastereomer A) | 510.1 |
| 54 | 12 | 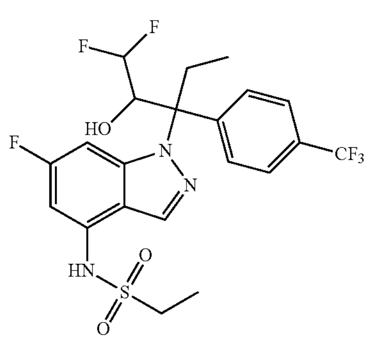 [SMILES: CCC(c1ccc(C(F)(F)F)cc1)(C(O)C(F)F)n1ncc2c(NS(=O)(=O)CC)cc(F)cc21] | N-(1-(1,1-difluoro-2-hydroxy-3-(4-(trifluoromethyl)phenyl)pentan-3-yl)-6-fluoro-1H-indazol-4-yl)ethanesulfonamide (diastereomer B) | 510.1 |

Compound 47 exhibited good metabolic stability in liver microsome and hepatocytes of multiple animal species. Additionally, Compound 47 exhibited a good PK profile in rats. The PK profile for Compound 47 is shown below:

| Cl (mL/min/kg) | $t_{1/2}$ (hours) | AUCN po ($\mu$M · h · kg/mg) | % F |
|---|---|---|---|
| 3.8 | 9.9 | 8.9 | 77 |

Below is the metabolic stability for Compound 47:

| | Human | Rat | Dog | Rhesus Monkey |
|---|---|---|---|---|
| Liver Microsome Stability ($t_{1/2}$) | 62 mins | 154 mins | 162 mins | 42 mins |
| Hepatocyte Stability ($t_{1/2}$) | >90 mins | >90 mins | >90 mins | >90 mins |

Using procedures similar to those described for Compounds 35-42 in Table 8, the following compounds in Table 12 were prepared

TABLE 12

| Compound Number | IP (nM) | Structure | IUPAC Name | Exact Mass [M + H]+ |
|---|---|---|---|---|
| 55 | 18 | 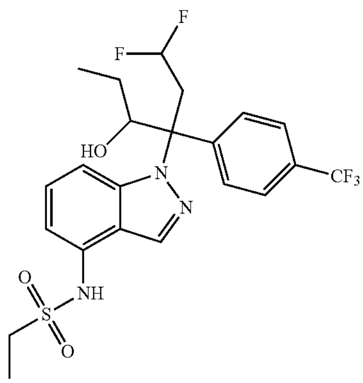 [SMILES: CCC(O)C(CC(F)F)(c1ccc(C(F)(F)F)cc1)n1ncc2c(NS(=O)(=O)CC)cccc21] | N-(1-(1,1-difluoro-4-hydroxy-3-(4-(trifluoromethyl)phenyl)hexan-3-yl)-1H-indazol-4-yl)ethanesulfonamide (Diastereomer C) | 506.1 |
| 56 | 10 | 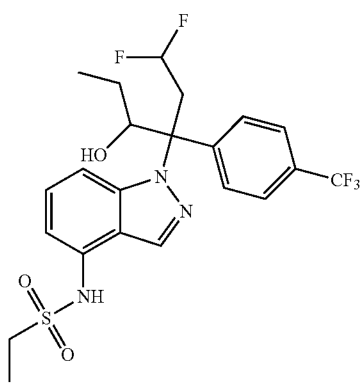 [SMILES: CCC(O)C(CC(F)F)(c1ccc(C(F)(F)F)cc1)n1ncc2c(NS(=O)(=O)CC)cccc21] | N-(1-(1,1-difluoro-4-hydroxy-3-(4-(trifluoromethyl)phenyl)hexan-3-yl)-1H-indazol-4-yl)ethanesulfonamide (Diastereomer D) | 506.1 |
| 57 | 43 | 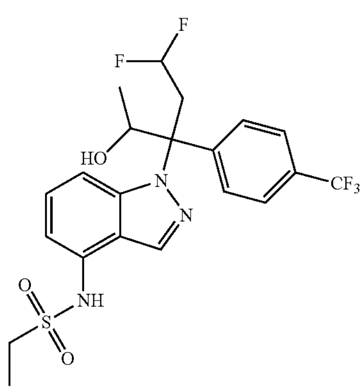 [SMILES: CCS(=O)(=O)Nc1cccc2c1cnn2C(CC(F)F)(c1ccc(C(F)(F)F)cc1)C(C)O] | N-(1-(1,1-difluoro-4-hydroxy-3-(4-(trifluoromethyl)phenyl)pentan-3-yl)-1H-indazol-4-yl)ethanesulfonamide (Diastereomer C) | 492.1 |

TABLE 12-continued

| Compound Number | IP (nM) | Structure | IUPAC Name | Exact Mass [M + H]+ |
|---|---|---|---|---|
| 58 | 38 | 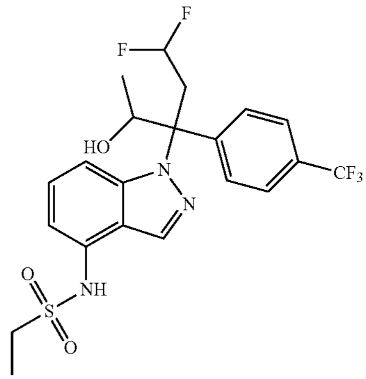 [SMILES: CCS(=O)(=O)Nc1cccc2c1cnn2C(CC(F)F)(c1ccc(C(F)(F)F)cc1)C(C)O] | N-(1-(1,1-difluoro-4-hydroxy-3-(4-(trifluoromethyl)phenyl)pentan-3-yl)-1H-indazol-4-yl)ethanesulfonamide (Diastereomer D) | 492.1 |

Individual diastereomers or enantiomers of the above racemic compounds can be obtained by using standard separation techniques, such as those described in the above Examples, with the appropriate columns and conditions.

Biological Assay

The activity of the compounds of the present invention regarding mineralocorticoid receptor antagonism can be evaluated using the following assay.

Assessment of MR Potency in HMR NH Pro Assay

The human MR NH Pro assay is a commercially available PathHunter™ Protein:Protein interaction assay (DiscoveRx; http://www.discoverx.com/nhrs/prod-nhrs.php) that measures the ability of compounds to antagonize full-length human Mineralocorticoid Receptor (MR) binding to a coactivator peptide. PathHunter™ CHO-K1 cells that overexpress human MR (Cat #93-0456C2, Lot No: 09B0913) were cultured in growth media (F12K w/Glutamine and phenol red (Gibco 11765-047) supplemented with 10% HI FBS (Gibco 16000); 0.25 mg/ml Hygromycin in PBS (Invitrogen 10687-010, 50 mg/ml); 100 I.U./mL and 100 µg/mL Pen/Strep (Gibco 15140-122); 0.6 mg/mL Geneticin (Gibco 10131-027).

Compounds were assessed for MR antagonist activity by incubating the cells with a titrating dose of compound in F12K w/Glutamine and phenol red culture media (Invitrogen 11765-047) supplemented with 1% Charcoal/Dextran Treated FBS (Hyclone #SH30068.01) and aldosterone (0.3 nM to about 1 nM) for 6 hours at 37° C. Cells were then treated with DiscoveRx detection reagent for 1 hour at rt and read using an Envision luminescence plate reader. % activity was measured relative to cells treated with aldosterone alone and $IC_{50}$ and IP values were calculated using ADA software. (The IP value, which is the inflection point of the non-linear regression curve, and is based on the slope, the minimum and the maximum points of the curve. The IP value is equal to the IC50 value when the slope is 1 and the minimum is 0 and the maximum is 100.)

1. Growth Media:
F12K w/Glutamine and phenol red (Gibco 11765-047)
10% HI FBS (Gibco 16000)
0.25 mg/ml Hygromycin in PBS (Invitrogen 10687-010, 50 mg/ml)
100 I.U./mL and 100 µg/mL Pen/Strep (Gibco 15140-122)
0.6 mg/mL Geneticin (Gibco 10131, 50 mg/ml)

2. Assay Media:
F12K w/Glutamine and phenol red (Invitrogen 11765-047)
1% Charcoal/Dextran Treated FBS (Hyclone #SH30068.01)

3. 3× PathHunter Detection Reagents (Cat#93-0001) (need ~6 ml/plate). 19× PathHunter Cell Assay Buffer
5× Emerald II
1× Galacton Star 4. Control Agonist: Aldosterone: Sigma cat# A9477
Stock solution was prepared at 10 µM in DMSO and stored at −20° C. for assay, dilute in assay media to 1.8 or 6 nM (6× of final concentration=about 0.3 nM to about 1.0 nM)

5. Cell line: PathHunter CHO-K1 MR cells Cat #93-0456C2, Lot No: 09B0913, from operation liquid nitrogen stock.

6. Control Antagonist: Spironolactone: Sigma #S-3378 and Eplerenone Sigma #107724-20-9 (10 mM stock concentration also prepared in DMSO and stored at −20° C.).

Methods:
Assay Set Up and Calculations:
1. Cells are grown in F12+FBS+Hygromycin+pen/strep+Genetin
2. Cells are collected with 0.05% trypsin and the cell suspension is spun and resuspended in a volume of F12+ 1.5% CD-FBS and counted.
3. The cells concentration was adjusted to 4×10⁵ cells/mL.
4. Cells were (25 µL/well) added to the wells of a 384 well plate.
5. The plate was then incubated at 37° C. over night in a humidified incubator with 5% $CO_2$.
6. Test compounds were titrated starting at 4.4 mM, 10-point titration in 1:3 dilution.
7. Aldosterone was diluted in assay media to 1.8 nM or 6 nM from 10 µM stock (final concentration to be about 0.3 nM to about 1.0 nM)

Protocol for 384 well plate format: 6 hr treatment:
1. 10K exponentially growing cells/well (25 µL) were resuspended in assay media and plated into each well using the Multidrop (Thermo Electron) (use white wall, clear bottom assay plates (Costar #3570) and incubated overnight at 37° C., 5% $CO_2$.
2. 0.25 µL 120× test compound (final DMSO concentration should be <1%) was added to each well n=2, 10 point titrations starting at 36.7 µM final concentration.

3. 5 µL of 6× agonist (final aldosterone concentration should be about 0.3 nM to about 1.0 nM) was added to all wells (using the PlateMate Plus.; (ThermoFisher) (except those wells in columns 23 and 24)

4. 5 µL of assay media was added to all wells in column 23 and 24.

5. Cells were then incubated for 6 hrs at 37° C., 5% $CO_2$.

6. 15 µL 3× DiscoveRx detection reagent was then added to to each well.

7. Plates were incubated for 1 hour at room temperature in the dark.

8. Plates were read on Envision (PerkinElmer) luminesence plate reader and analyzed using ADA.

As seen in the Examples above, representative compounds of the instant invention were tested in the above assay and had IP values less than about 2000 nM.

What is claimed is:

1. A compound selected from

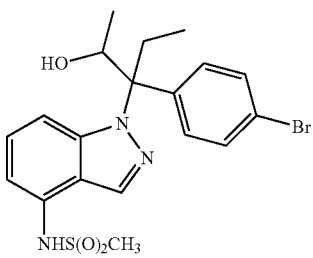

N-(1-(3-(4-bromophenyl)-2-hydroxypentan-3-yl)-1H-indazol-4-yl) methansulfonamide,

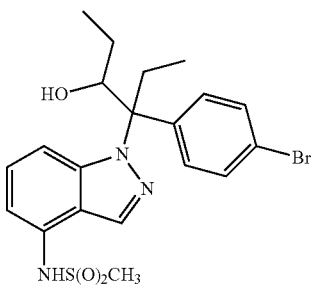

N-(1-(3-(4-bromophenyl)-4-hydroxyhexan-3-yl)-1H-indazol-4-yl)methansulfonamide,

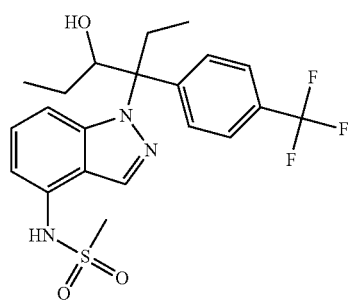

N-(1-(4-hydroxy-3-(4-(trifluoromethyl)phenyl)hexan-3-yl)-1H-indazol-4-yl)methansulfonamide,

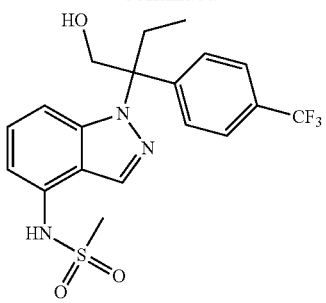

N-(1-(1-hydroxy-2-(4-(trifluoromethyl)phenyl)butan-2-yl)-1H-indazol-4-yl)methansulfonamide,

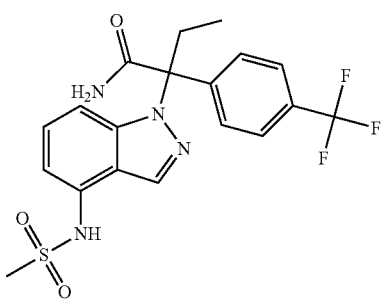

2-(4-(methylsulfonamido)-1H-indazol-1-yl)-2-(4-(trifluoromethyl) phenyl) butanamide,

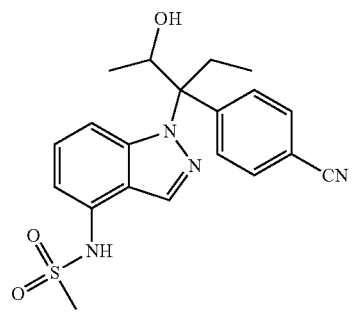

N-(1-(3-(4-cyanophenyl)-2-hydroxypentan-3-yl)-1H-indazol-4-yl)methanesulfonamide,

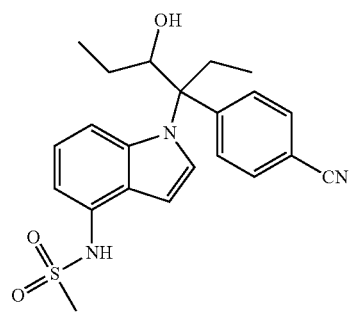

N-(1-(3-(4-cyano)-4-hydroxyhexan-3-yl)-1H-indazol-4-yl)methanesulfonamide,

-continued

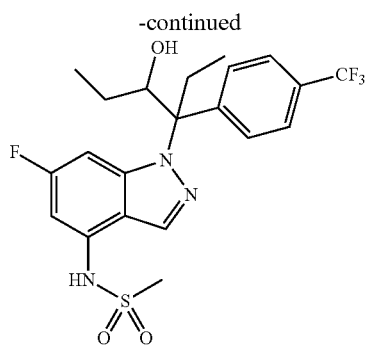

N-(6-fluoro-1-(4-hydroxy-3-(4-(trifluoromethyl)phenyl)hexan-3-yl)-1H-indazol-4-yl)methansulfonamide,

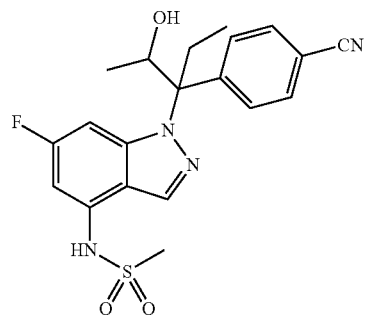

N-(1-(3-(4-cyanophenyl)-2-hydroxypentan-3-yl)-6-fluoro-1H-indazol-4-yl)methanesulfonamide,

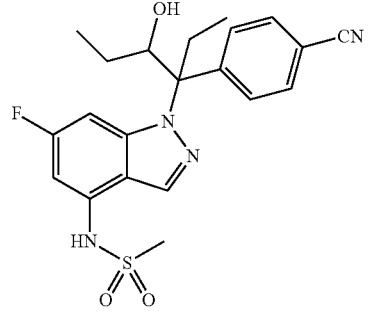

N-(1-(3-(4-cyanophenyl)-4-hydroxyhexan-3-yl)-6-fluoro-1H-indazol-4-yl)methanesulfonamide,

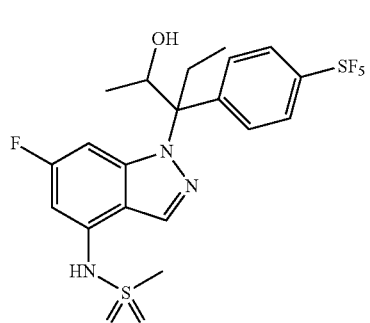

N-(6-fluoro-1-{2-hydroxy-3-[4-(pentafluoro-$\lambda^6$-sulfanyl)phenyl]pentan-3-yl}-1H-indazol-4-yl)methanesulfonamide, -continued

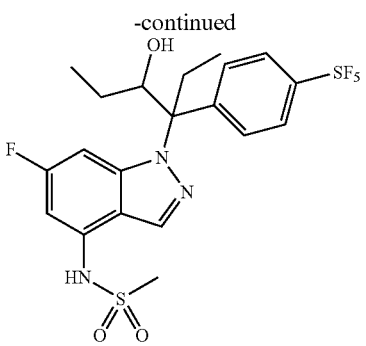

N-(6-fluoro-1-{4-hydroxy-3-[4-(pentafluoro-$\lambda^6$-sulfanyl)phenyl]hexan-3-yl}-1H-indazol-4-yl)methanesulfonamide,

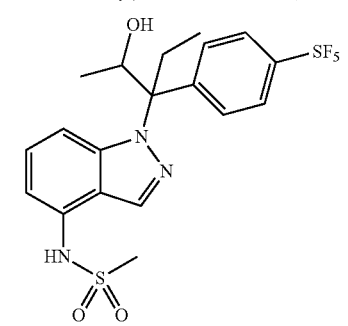

N-(1-{2-hydroxy-3-[4-(pentafluoro-$\lambda^6$-sulfanyl)phenyl]pentan-3-yl}-1H-indazol-4-yl)methanesulfonamide,

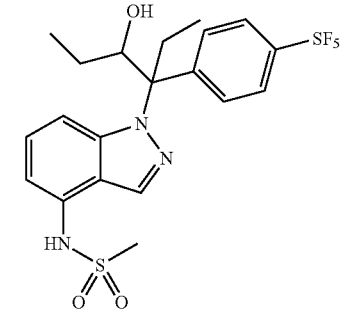

N-(1-{4-hydroxy-3-[4-(pentafluoro-$\lambda^6$-sulfanyl)phenyl]hexan-3-yl}-1H-indazol-4-yl)methanesulfonamide,

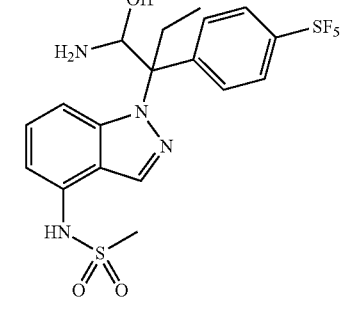

2-{4-[(methylsulfonyl)amino]-1H-indazol-1-yl}-2-[4-(pentafluoro-$\lambda^6$-sulfanyl)phenyl]butanamide, -continued

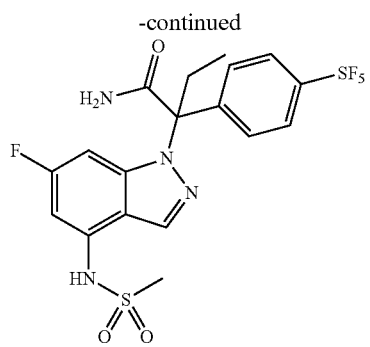

2-{6-fluoro-4-
[(methylsulfonyl)amino]-1H-
indazol-1-yl}-2-[4-(pentafluoro-
λ⁶-sulfanyl)phenyl]butanamide,

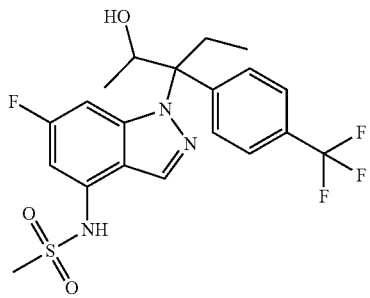

N-(6-fluoro-1-(2-hydroxy-3-(4-
(trifluoromethyl)phenyl)pentan-3-
yl)-1H-indazol-4-
yl)methanesulfonamide,

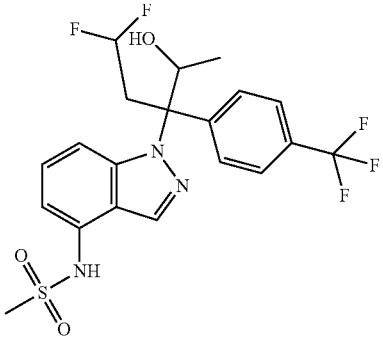

N-(1-(1,1-difluoro-4-hydroxy-3-
(4-(trifluoromethyl)phenyl)pentan-
3-yl)-1H-indazol-4-
yl)methanesulfonamide,

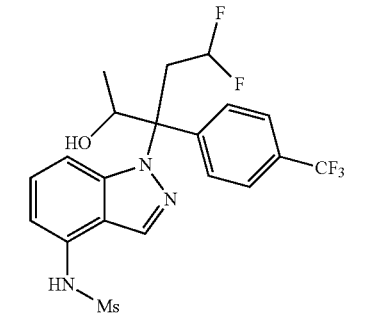

N-(1-(1,1-difluoro-4-hydroxy-3-
(4-(trifluoromethyl)phenyl)
pentan-3-yl)-1H-indazol-4-
yl)methanesulfonamide, -continued

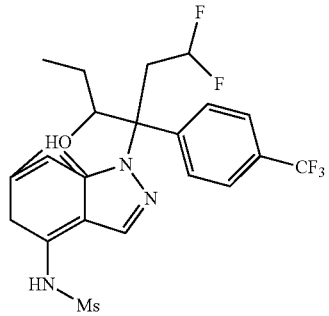

N-(1-(1,1-difluoro-4-hydroxy-3-
(4-(trifluoromethyl)phenyl)hexan-
3-yl)-1H-indazol-4-
yl)methanesulfonamide,

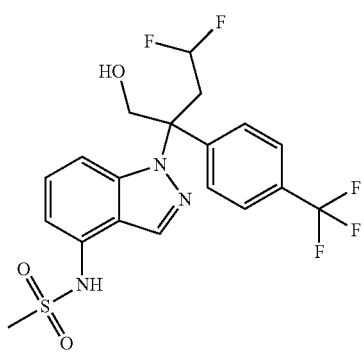

N-(1-(4,4-difluoro-1-hydroxy-2-
(4-(trifluoromethyl)phenyl)butan-
2-yl)-1H-indazol-4-
yl)methanesulfonamide,

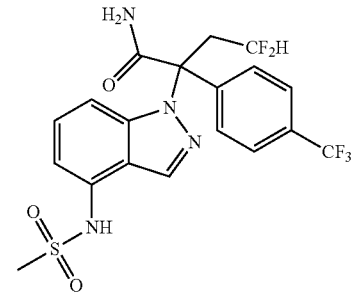

4,4-difluoro-2-(4-
(methylsulfonamido)-1H-indazol-
1-yl)-2-(4-(trifluoromethyl)phenyl)
butanamide,

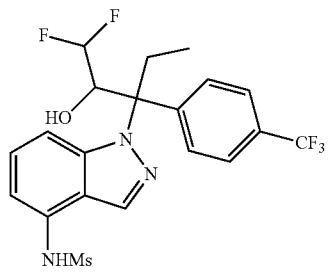

N-(1-(1,1-difluoro-2-hydroxy-3-
(4-(trifluoromethyl)phenyl)
pentan-3-yl)-1H-indazol-4-
yl)methanesulfonamide, -continued

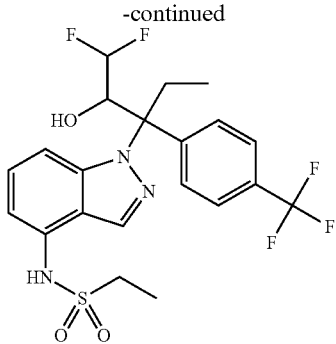

N-(1-(1,1-difluoro-2-hydroxy-3-
(4-(trifluoromethyl)phenyl)
pentan-3-yl)-1H-indazol-4-
yl)ethanesulfonamide,

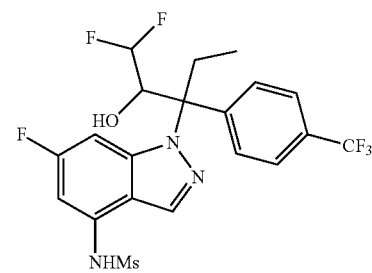

N-(1-(1,1-difluoro-2-hydroxy-3-
(4-(trifluoromethyl)phenyl)
pentan-3-yl)-6-fluoro-1H-indazol-
4-yl) methanesulfonamide,

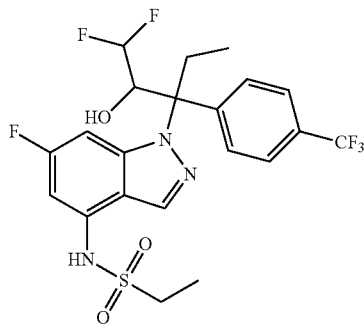

N-(1-(1,1-difluoro-2-hydroxy-3-
(4-(trifluoromethyl)phenyl)
pentan-3-yl)-6-fluoro-1H-indazol-
4-yl)ethanesulfonamide, -continued

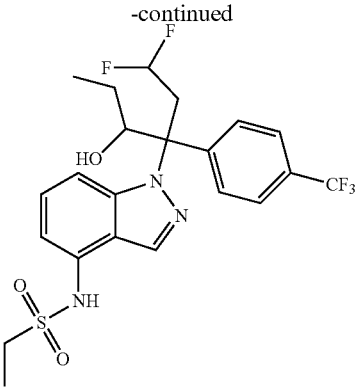

N-(1-(1,1-difluoro-4-hydroxy-3-
(4-(trifluoromethyl)phenyl) hexan-
3-yl)-1H-indazol-4-
yl)ethanesulfonamide, or a pharmaceutically acceptable salt thereof.

2. The compound of claim 1 selected from

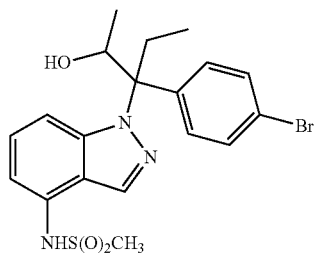

N-(1-(3-(4-bromophenyl)-2-
hydroxypentan-3-yl)-1H-indazol-
4-yl) methansulfonamide,

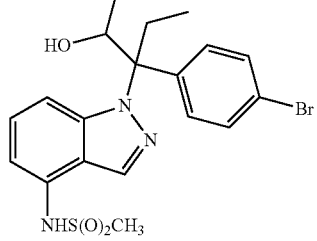

N-(1-(3-(4-bromophenyl)-4-
hydroxyhexan-3-yl)-1H-indazol-4-
yl)methansulfonamide,

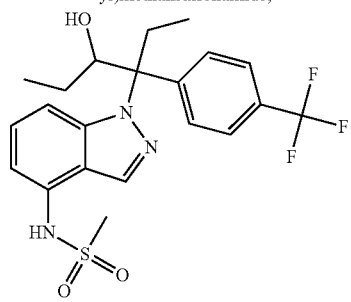

N-(1-(4-hydroxy-3-(4-
(trifluoromethyl)phenyl)hexan-3-
yl)-1H-indazol-4-
yl)methansulfonamide, or -continued

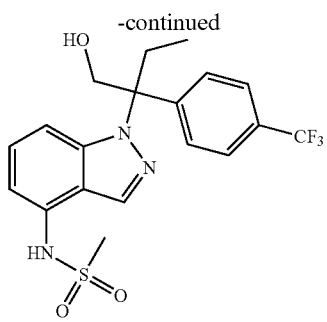

N-(1-(1-hydroxy-2-(4-(trifluoromethyl)phenyl)butan-2-yl)-1H-indazol-4-yl)methansulfonamide,

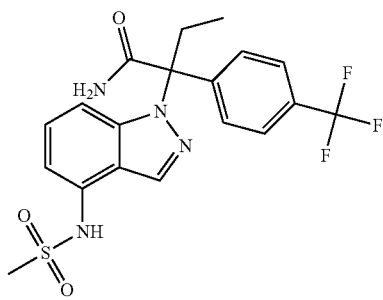

2-(4-(methylsulfonamido)-1H-indazol-1-yl)-2-(4-(trifluoromethyl) phenyl)butanamide, -continued

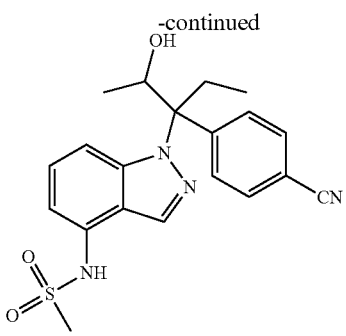

N-(1-(3-(4-cyanophenyl)-2-hydroxypentan-3-yl)-1H-indazol-4-yl)methanesulfonamide,

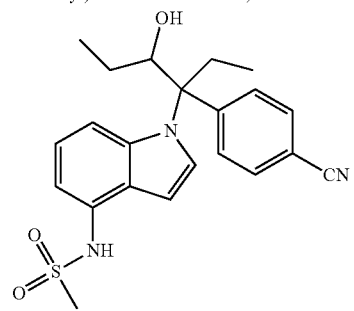

N-(1-(3-(4-cyano)-4-hydroxyhexan-3-yl)-1H-indazol-4-yl)methanesulfonamide, or a pharmaceutically acceptable salt thereof.

3. The compound of claim 1 selected from

| Compound No. | Structure | Name |
|---|---|---|
| 1 | 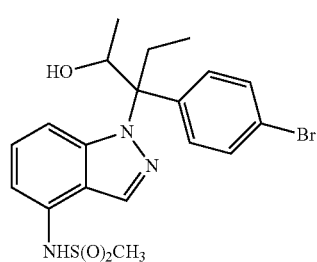 | N-(1-(3-(4-bromophenyl)-2-hydroxypentan-3-yl)-1H-indazol-4-yl)methanesulfonamide (diastereomer C), |
| 2 | 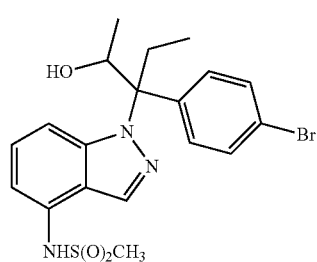 | N-(1-(3-(4-bromophenyl)-2-hydroxypentan-3-yl)-1H-indazol-4-yl)methanesulfonamide (diastereomer D), |

| Compound No. | Structure | Name |
|---|---|---|
| 3 | 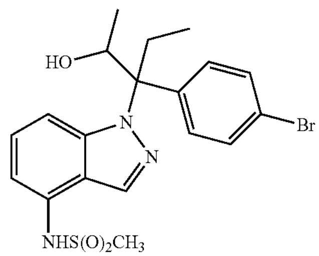 | N-(1-(3-(4-bromophenyl)-2-hydroxypentan-3-yl)-1H-indazol-4-yl)methanesulfonamide (diastereomer A), |
| 4 | 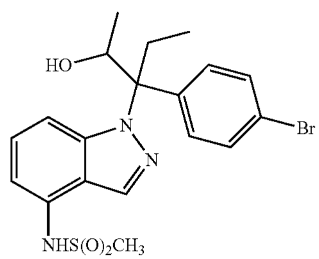 | N-(1-(3-(4-bromophenyl)-2-hydroxypentan-3-yl)-1H-indazol-4-yl)methanesulfonamide (diastereomer B), |
| 5 | 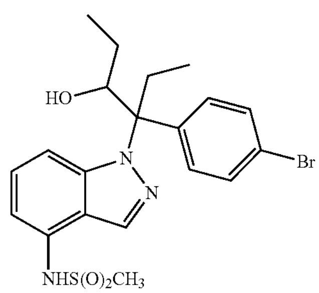 | N-(1-(3-(4-bromophenyl)-4-hydroxyhexan-3-yl)-1H-indazol-4-yl(methanesulfonamide (diastereomer C), |
| 6 | 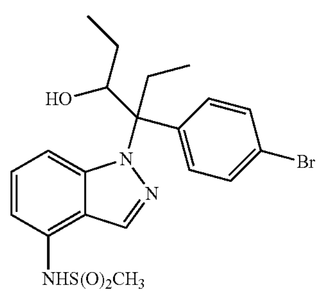 | N-(1-(3-(4-bromophenyl)-4-hydroxyhexan-3-yl)-1H-indazol-4-yl)methanesulfonamide (diastereomer D), |
| 7 | 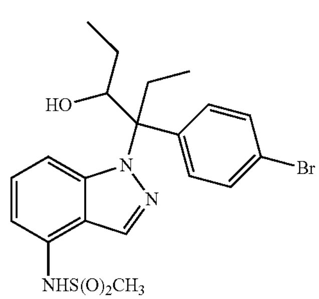 | N-(1-(3-(4-bromophenyl)-4-hydroxyhexan-3-yl)-1H-indazol-4-yl)methanesulfonamide (diastereomer A), |

| Compound No. | Structure | Name |
|---|---|---|
| 8 | 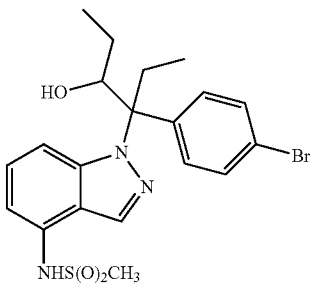 | N-(1-(3-(4-bromophenyl)-4-hydroxyhexan-3-yl)-1H-indazol-4-yl)methanesulfonamide (diastereomer B), |
| 9 | 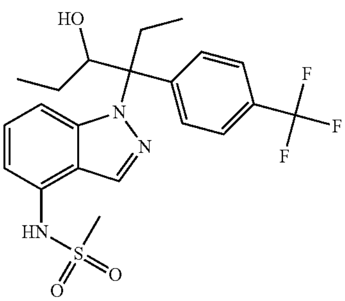 [SMILES: CCC(O)C(CC)(c1ccc(C(F)(F)F)cc1)n1ncc2c(NS(C)(=O)=O)cccc21] | N-(1-(4-hydroxy-3-(4-(trifluoromethyl)phenyl)hexan-3-yl)-1H-indazol-4-yl)methanesulfonamide (diastereomer A), |
| 10 | 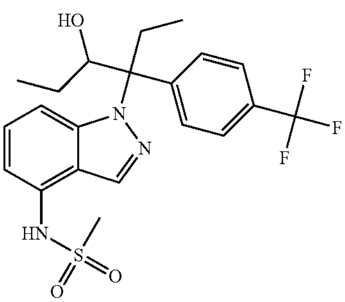 [SMILES: CCC(O)C(CC)(c1ccc(C(F)(F)F)cc1)n1ncc2c(NS(C)(=O)=O)cccc21] | N-(1-(4-hydroxy-3-(4-(trifluoromethyl)phenyl)hexan-3-yl)-1H-indazol-4-yl)methanesulfonamide (diastereomer B), |
| 11 | 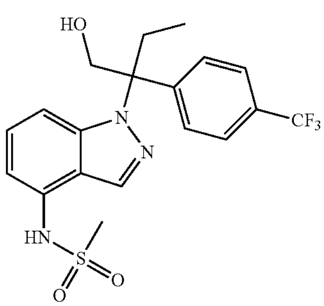 [SMILES: CCC(CO)(c1ccc(C(F)(F)F)cc1)n1ncc2c(NS(C)(=O)=O)cccc21] | N-(1-(1-hydroxy-2-(4-(trifluoromethyl)phenyl)butan-2-yl)-1H-indazol-4-yl)methanesulfonamide (enantiomer A), |
| 12 | 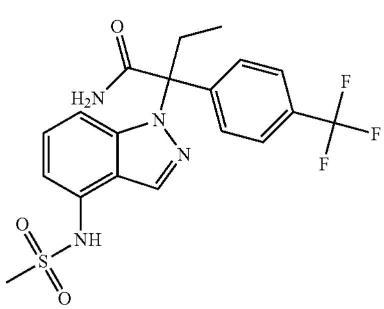 | 2-(4-(methylsulfonamido)-1H-imdazol-1-yl)-2-(4-(trifluoromethyl)phenyl)butanamide (enantiomer A), |

-continued

| Compound No. | Structure | Name |
|---|---|---|
| 13 | 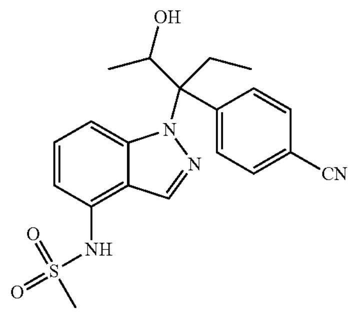 [SMILES: CCC(c1ccc(C#N)cc1)(C(C)O)n1ncc2c(NS(C)(=O)=O)cccc21] | N-(1-(3-(4-cyanophenyl)-2-hydroxypentan-3-yl)-1H-indazol-4-yl)methanesulfonamide (diastereomer A), or |
| 14 | | N-(1-(3-(4-cyano)-4-hydroxyhexan-3-yl)-1H-indol-4-yl)methanesulfonamide (diastereomer C), | or a pharmaceutically acceptable salt thereof.

4. The compound according to claim 1, selected from

| Compound No. | Structure | Name |
|---|---|---|
| 17 | 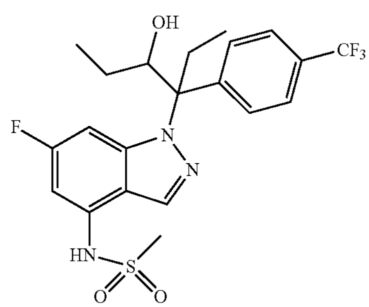 [SMILES: CCC(O)C(CC)(c1ccc(C(F)(F)F)cc1)n1ncc2c(NS(C)(=O)=O)cc(F)cc21] | N-(6-fluoro-1-(4-hydroxy-3-(4-(trifluoromethyl)phenyl)hexan-3-yl)-1H-indazol-4-yl)methanesulfonamide (Diastereomer A), |
| 18 | 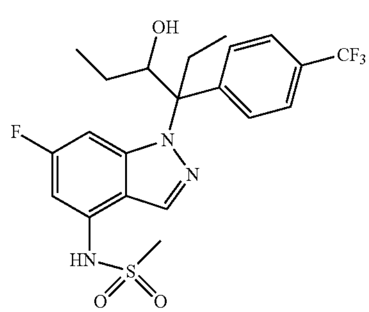 [SMILES: CCC(O)C(CC)(c1ccc(C(F)(F)F)cc1)n1ncc2c(NS(C)(=O)=O)cc(F)cc21] | N-(6-fluoro-1-(4-hydroxy-3-(4-(trifluoromethyl)phenyl)hexan-3-yl)-1H-indazol-4-yl)methanesulfonamide (Diastereomer B), |

| Compound No. | Structure | Name |
|---|---|---|
| 19 | 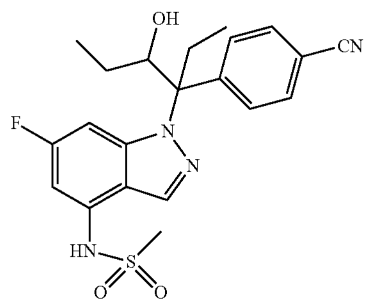 [SMILES: CCC(O)C(CC)(c1ccc(C#N)cc1)n1ncc2c(NS(C)(=O)=O)cc(F)cc21] | N-(1-(3-(4-cyanophenyl)-2-hydroxypentan-3-yl)-6-fluoro-1H-indazol-4-yl)methanesulfonamide (Diastereomer A), |
| 20 | 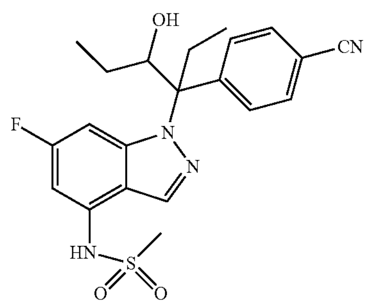 [SMILES: CCC(O)C(CC)(c1ccc(C#N)cc1)n1ncc2c(NS(C)(=O)=O)cc(F)cc21] | N-(1-(3-(4-cyanophenyl)-4-hydroxyhexan-3-yl)-6-fluoro-1H-indazol-4-yl)methanesulfonamide (Diastereomer B), |
| 21 | 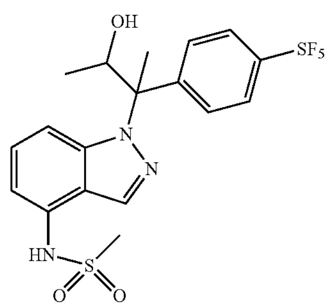 | N-(1-{2-hydroxy-3-[4-(pentafluoro-$\lambda^6$-sulfanyl)phenyl]pentan-3-yl}-1H-indazol-4-yl)methanesulfonamide (Diasteromer A), |
| 22 | 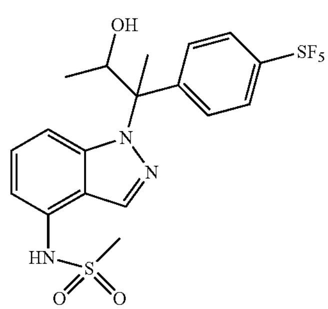 | N-(1-{2-hydroxy-3-[4-(pentafluoro-$\lambda^6$-sulfanyl)phenyl]pentan-3-yl}-1H-indazol-4-yl)methanesulfonamide (Diasteromer B), |
| 23 | 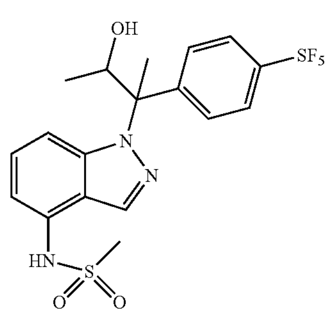 | N-(1-{2-hydroxy-3-[4-(pentafluoro-$\lambda^6$-sulfanyl)phenyl]pentan-3-yl}-1H-indazol-4-yl)methanesulfonamide (Diasteromer C), |

-continued

| Compound No. | Structure | Name |
|---|---|---|
| 24 | 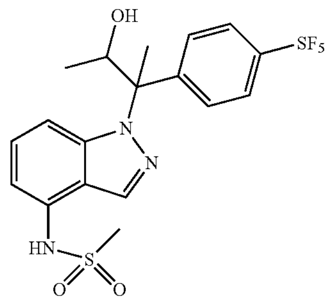 | N-(1-{2-hydroxy-3-[4-(pentafluoro-$\lambda^6$-sulfanyl)phenyl]pentan-3-yl}-1H-indazol-4-yl)methanesulfonamide (Diasteromer D), |
| 25 | 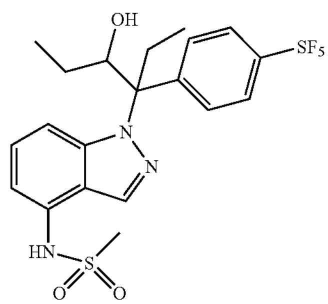 | N-(1-{4-hydroxy-3-[4-(pentafluoro-$\lambda^6$-sulfanyl)phenyl]hexan-3-yl}-1H-indazol-4-yl)methanesulfonamide (Diastereomers A and B), |
| 26 | 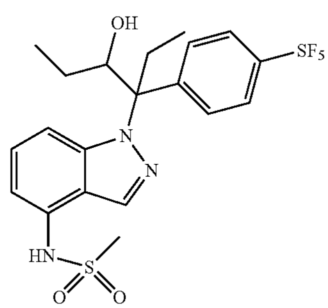 | N-(1-{4-hydroxy-3-[4-(pentafluoro-$\lambda^6$-sulfanyl)phenyl]hexan-3-yl}-1H-indazol-4-yl)methanesulfonamide (Diastereomers A and B), or |
| 27 | | 2-{4-[(methylsulfonyl)amino]-1H-indazol-1-yl}-2-[4-(pentafluoro-$\lambda^6$-sulfanyl)phenyl]butanamide (racemic), | or a pharmaceutically acceptable salt thereof.

5. The compound of claim 1 selected from

| 31 | N-(6-fluoro-1-(2-hydroxy-3-(4-(trifluoromethyl)phenyl)pentan-3-yl)-1H-indazol-4-yl)methanesulfonamide (diastereomer A), |
| 32 | N-(6-fluoro-1-(2-hydroxy-3-(4-(trifluoromethyl)phenyl)pentan-3-yl)-1H-indazol-4-yl)methanesulfonamide (diastereomer B), |
| 33 | N-(6-fluoro-1-(2-hydroxy-3-(4-(trifluoromethyl)phenyl)pentan-3-yl)-1H-indazol-4-yl)methanesulfonamide (diastereomer C), or |
| 34 | N-(6-fluoro-1-(2-hydroxy-3-(4-(trifluoromethyl)phenyl)pentan-3-yl)-1H-indazol-4-yl)methanesulfonamide (diastereomer D), | or a pharmaceutically acceptable salt thereof.

6. A compound of claim 1 selected from

| Compound No. | Structure | Name |
|---|---|---|
| 35 | | N-(1-(1,1-difluoro-4-hydroxy-3-(4-(trifluoromethyl)phenyl)pentan-3-yl)-1H-indazol-4-yl)methanesulfonamide (Diastereomer C), |
| 36 | | N-(1-(1,1-difluoro-4-hydroxy-3-(4-(trifluoromethyl)phenyl)pentan-3-yl)-1H-indazol-4-yl)methanesulfonamide (Diastereomer D), |
| 37 | | N-(1-(1,1-difluoro-4-hydroxy-3-(4-(trifluoromethyl)phenyl)pentan-3-yl)-1H-indazol-4-yl)methanesulfonamide (Diastereomer A), |
| 38 | 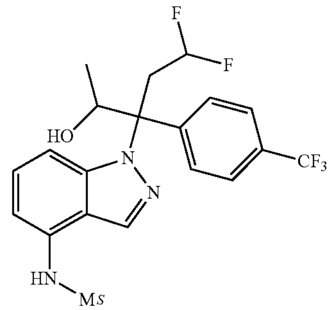 | N-(1-(1,1-difluoro-4-hydroxy-3-(4-(trifluoromethyl)phenyl)pentan-3-yl)-1H-indazol-4-yl)methanesulfonamide (Diastereomer B), |
| 39 | 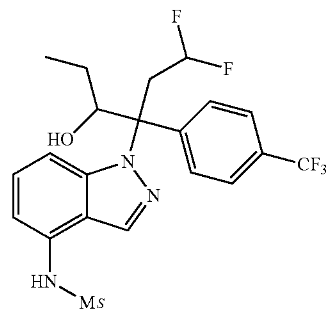 | N-(1-(1,1-difluoro-4-hydroxy-3-(4-(trifluoromethyl)phenyl)hexan-3-yl)-1H-indazol-4-yl)methanesulfonamide (Diastereomer C), |
| 40 | 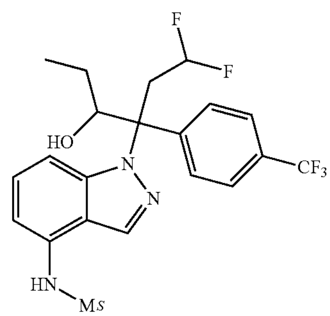 | N-(1-(1,1-difluoro-4-hydroxy-3-(4-(trifluoromethyl)phenyl)hexan-3-yl)-1H-indazol-4-yl)methanesulfonamide (Diastereomer D), |
| 41 | 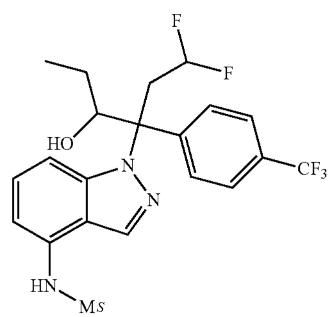 | N-(1-(1,1-difluoro-4-hydroxy-3-(4-(trifluoromethyl)phenyl)hexan-3-yl)-1H-indazol-4-yl)methanesulfonamide (Diastereomer A), or |
| | | N-(1-(1,1-difluoro-4-hydroxy-3-(4-(trifluoromethyl)phenyl)hexan-3-yl)-1H-indazol-4-yl)methanesulfonamide (Diastereomer B), | or a pharmaceutically acceptable salt thereof.

7. A compound according to claim 1, selected from

| Compound No. | Structure | Name |
|---|---|---|
| 43 | 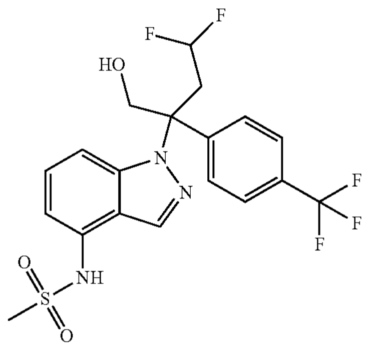 [SMILES: CS(=O)(=O)Nc1cccc2c1cnn2C(CO)(CC(F)F)c1ccc(C(F)(F)F)cc1] | N-(1-(4,4-difluoro-1-hydroxy-2-(4-(trifluoromethyl)phenyl)butan-2-yl)-1H-indazol-4-yl)methanesulfonamide (Enantiomer A), |
| 44 | 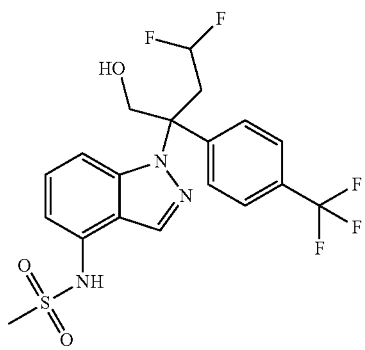 [SMILES: CS(=O)(=O)Nc1cccc2c1cnn2C(CO)(CC(F)F)c1ccc(C(F)(F)F)cc1] | N-(1-(4,4-difluoro-1-hydroxy-2-(4-(trifluoromethyl)phenyl)butan-2-yl)-1H-indazol-4-yl)methanesulfonamide (Enantiomer B), |
| 45 | 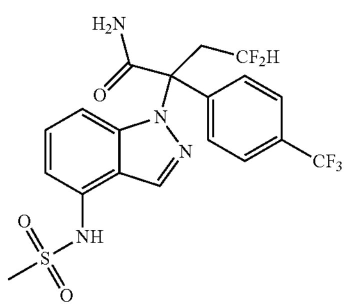 [SMILES: CS(=O)(=O)Nc1cccc2c1cnn2C(CC(F)F)(C(N)=O)c1ccc(C(F)(F)F)cc1] | 4,4-difluoro-2-(4-(methylsulfonamido)-1H-indazol-1-yl)-2-(4-(trifluoromethyl)phenyl)butanamide (Enantiomer A), or |
| 46 | | 4,4-difluoro-2-(4-(methylsulfonamido)-1H-indazol-1-yl)-2-(4-(trifluoromethyl)phenyl)butanamide (Enantiomer B), | or a pharmaceutically acceptable salt thereof.

8. A compound according to claim 1, selected from

| Compound Number | Structure | Name |
|---|---|---|
| 47 | 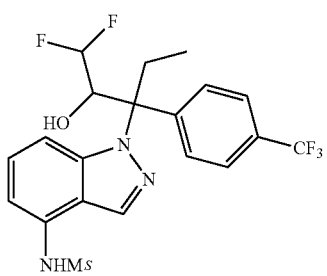 | N-(1-(1,1-difluoro-2-hydroxy-3-(4-(trifluoromethyl)phenyl)pentan-3-yl)-1H-indazol-4-yl)methanesulfonamide (Diastereomer A), |
| 48 | 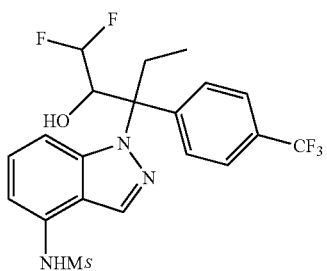 | N-(1-(1,1-difluoro-2-hydroxy-3-(4-(trifluoromethyl)phenyl)pentan-3-yl)-1H-indazol-4-yl)methanesulfonamide (Diastereomer B), |
| 49 | 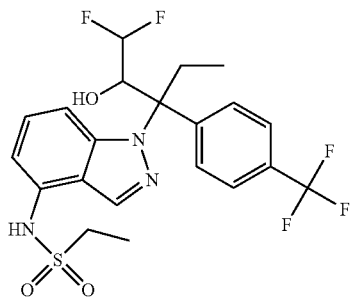 [SMILES: CCC(c1ccc(C(F)(F)F)cc1)(C(O)C(F)F)n1ncc2c(NS(=O)(=O)CC)cccc21] | N-(1-(1,1-difluoro-2-hydroxy-3-(4-(trifluoromethyl)phenyl)pentan-3-yl)-1H-indazol-4-yl)ethanesulfonamide (Diastereomer A), |
| 50 | 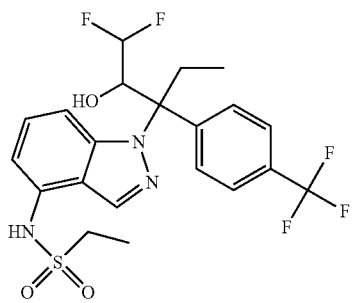 [SMILES: CCC(c1ccc(C(F)(F)F)cc1)(C(O)C(F)F)n1ncc2c(NS(=O)(=O)CC)cccc21] | N-(1-(1,1-difluoro-2-hydroxy-3-(4-(trifluoromethyl)phenyl)pentan-3-yl)-1H-indazol-4-yl)ethanesulfonamide (Diastereomer B), |
| 51 | 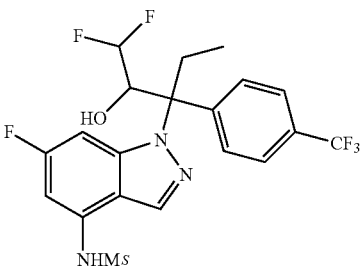 | N-(1-(1,1-difluoro-2-hydroxy-3-(4-(trifluoromethyl)phenyl)pentan-3-yl)-6-fluoro-1H-indazol-4-yl)methanesulfonamide (diastereomer A), |

-continued

| Compound Number | Structure | Name |
|---|---|---|
| 52 | 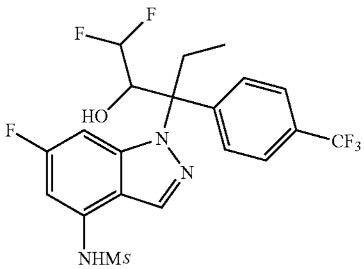 | N-(1-(1,1-difluoro-2-hydroxy-3-(4-(trifluoromethyl)phenyl)pentan-3-yl)-6-fluoro-1H-indazol-4-1)methanesulfonamide (diastereomer B), |
| 53 | 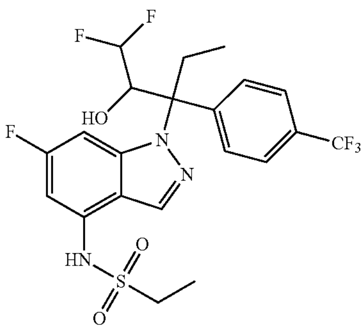 [SMILES: CCC(c1ccc(C(F)(F)F)cc1)(C(O)C(F)F)n1ncc2c(NS(=O)(=O)CC)cc(F)cc21] | N-(1-(1,1-difluoro-2-hydroxy-3-(4-(trifluoromethyl)phenyl)pentan-3-yl)-6-fluoro-1H-indazol-4-yl)ethanesulfonamide (diastereomer A), or |
| 54 | | N-(1-(1,1-difluoro-2-hydroxy-3-(4-(trifluoromethyl)phenyl)pentan-3-yl)-6-fluoro-1H-indazol-4-yl)ethanesulfonamide (diastereomer B), | or a pharmaceutically acceptable salt thereof.

9. A compound of claim 1 selected from

| Compound Number | Structure | Name |
|---|---|---|
| 55 | 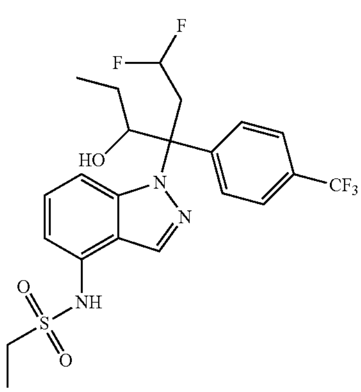 [SMILES: CCC(O)C(CC(F)F)(c1ccc(C(F)(F)F)cc1)n1ncc2c(NS(=O)(=O)CC)cccc21] | N-(1-(1,1-difluoro-4-hydroxy-3-(4-(trifluoromethyl)phenyl)hexan-3-yl)-1H-indazol-4-yl)ethanesulfonamide (Diastereomer C), |

| Compound Number | Structure | Name |
|---|---|---|
| 56 | 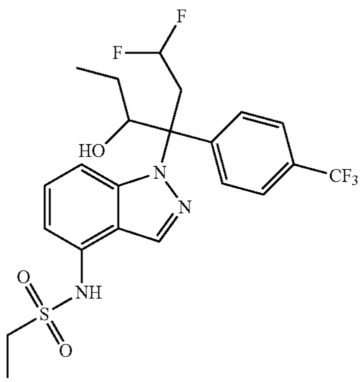 [SMILES: CCC(O)C(CC(F)F)(c1ccc(C(F)(F)F)cc1)n1ncc2c(NS(=O)(=O)CC)cccc21] | N-(1-(1,1-difluoro-4-hydroxy-3-(4-(trifluoromethyl)phenyl)hexan-3-yl)-1H-indazol-4-yl)ethanesulfonamide (Diastereomer D), |
| 57 | 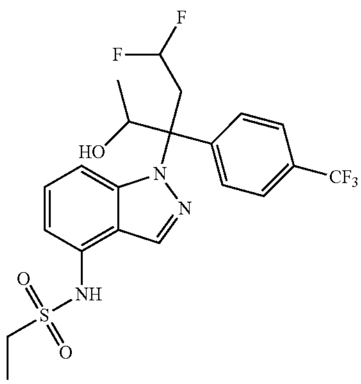 [SMILES: CCS(=O)(=O)Nc1cccc2c1cnn2C(CC(F)F)(c1ccc(C(F)(F)F)cc1)C(C)O] | N-(1-(1,1-difluoro-4-hydroxy-3-(4-(trifluoromethyl)phenyl)pentan-3-yl)-1H-indazol-4-yl)ethanesulfonamide (Diastereomer C), or |
| 58 | | N-(1-(1,1-difluoro-4-hydroxy-3-(4-(trifluoromethyl)phenyl)pentan-3-yl)-1H-indazol-4-yl)ethanesulfonamide (Diastereomer D), | or a pharmaceutically acceptable salt thereof.

10. The compound of claim 1 selected from
N-(1-(3-(4-bromophenyl)-2-hydroxypentan-3-yl)-1H-indazol-4-yl) methanesulfonamide (diastereomer D);
N-(1-(4-hydroxy-3-(4-(trifluoromethyl)phenyl)hexan-3-yl)-1H-indazol-4-yl)methanesulfonamide (diastereomer A);
N-(6-fluoro-1-(2-hydroxy-3-(4-(trifluoromethyl)phenyl) pentan-3-yl)-1H-indazol-4-yl)methanesulfonamide (diastereomer A);
N-(1-(1,1-difluoro-2-hydroxy-3-(4-(trifluoromethyl)phenyl) pentan-3-yl)-1H-indazol-4-yl)methanesulfonamide (Diastereomer A);
N-(1-(1,1-difluoro-4-hydroxy-3-(4-(trifluoromethyl)phenyl) pentan-3-yl)-1H-indazol-4-yl)methanesulfonamide (Diastereomer C); or
4,4-difluoro-2-(4-(methylsulfonamido)-1H-indazol-1-yl)-2-(4-(trifluoromethyl)phenyl) butanamide (Enantiomer A);

or a pharmaceutically acceptable salt thereof.

11. A pharmaceutical composition comprised of the compound of claim 1 or a pharmaceutically acceptable salt thereof, and a pharmaceutically acceptable carrier.

12. The pharmaceutical composition of claim 11 further comprises a second pharmaceutically active agent.

13. A method of treating heart failure, hypertension, or atherosclerosis in a human patient in need of, comprising administering a therapeutically effective amount of a compound of claim 1, or a pharmaceutically acceptable salt thereof.

14. A method of treating a physiological or pathologic disease, selected from Conn's Syndrome, heart failure, primary and secondary hyperaldosteronism, hypertension (isolated systolic and combined systolic/diastolic), arrhythmias, myocardial fibrosis, myocardial infarction, Bartter's Syndrome, atherosclerosis, retinopathy, choriretinopathy, obstructive sleep apnea, psychoses, memory disturbances, depression, and bipolar disorder, comprising administering to a patient a therapeutically effective amount of a compound of claim 1 or a pharmaceutically acceptable salt thereof.

* * * * *